US012605537B2

(12) United States Patent
Abrams et al.

(10) Patent No.: US 12,605,537 B2
(45) Date of Patent: Apr. 21, 2026

(54) IMPLANTABLE MEDICAL DEVICE FOR USE WITH OR HAVING RECORDING ELECTRODE

(71) Applicant: Biogen MA Inc., Cambridge, MA (US)

(72) Inventors: Daniel J. Abrams, Denver, CO (US); Matias Maturana, Melbourne (AU); Ross Thomas, Melbourne (AU); Christopher Smith, Melbourne (AU)

(73) Assignee: Biogen MA Inc., Cambridge, MA (US)

( * ) Notice: Subject to any disclaimer, the term of this patent is extended or adjusted under 35 U.S.C. 154(b) by 339 days.

(21) Appl. No.: 18/108,414

(22) Filed: Feb. 10, 2023

(65) Prior Publication Data

US 2023/0277840 A1 Sep. 7, 2023

Related U.S. Application Data

(60) Provisional application No. 63/310,288, filed on Feb. 15, 2022.

(51) Int. Cl.
| | |
|---|---|
| *A61N 1/05* | (2006.01) |
| *A61B 5/00* | (2006.01) |
| *A61B 5/291* | (2021.01) |
| *A61B 5/293* | (2021.01) |

(52) U.S. Cl.
CPC ............ *A61N 1/0539* (2013.01); *A61B 5/293* (2021.01); *A61B 5/6864* (2013.01); *A61B 5/6868* (2013.01)

(58) Field of Classification Search
CPC ......... A61B 5/29; A61B 5/293; A61B 5/6864; A61B 5/6868; A61N 1/0539
See application file for complete search history.

(56) References Cited

U.S. PATENT DOCUMENTS

| | | | |
|---|---|---|---|
| 1,456,469 | A | 5/1923 | Schwidetzky |
| 2,609,818 | A | 9/1952 | Parrine |
| 3,040,743 | A | 6/1962 | Knut |
| 3,506,006 | A | 4/1970 | Lange, Jr. |
| 3,563,373 | A | 2/1971 | Paulson |
| 3,640,269 | A | 2/1972 | Delgado |
| 3,892,237 | A | 7/1975 | Steiner |

(Continued)

FOREIGN PATENT DOCUMENTS

| | | |
|---|---|---|
| CA | 3098311 A1 | 11/2019 |
| DE | 3127882 A1 | 2/1983 |

(Continued)

OTHER PUBLICATIONS

International Patent Application No. PCT/US2023/012940, filed Feb. 13, 2023; International Preliminary Report on Patentability issued Apr. 2, 2024; 10 pages.

(Continued)

*Primary Examiner* — Eun Hwa Kim
(74) *Attorney, Agent, or Firm* — Finnegan, Henderson, Farabow, Garrett & Dunner, LLP

(57) ABSTRACT

A burr hole device is configured to receive a catheter and a cable of a sheath. The sheath is configured to receive a portion of the catheter and has an electrode. When the catheter and sheath are implanted with the burr hole device, the catheter and electrode of the sheath are implanted in a brain. Systems and apparatuses may include the burr hole device and/or a cranial port device, the catheter, and the sheath.

8 Claims, 26 Drawing Sheets

(56)            References Cited

U.S. PATENT DOCUMENTS

| | | | |
|---|---|---|---|
| 4,281,666 A | 8/1981 | Cosman | |
| 4,281,667 A | 8/1981 | Cosman | |
| 4,464,168 A | 8/1984 | Redmond et al. | |
| 4,500,311 A | 2/1985 | Redmond et al. | |
| 4,583,968 A | 4/1986 | Mahurkar | |
| 4,677,985 A | 7/1987 | Bro et al. | |
| 4,723,556 A | 2/1988 | Sussman | |
| 4,732,850 A | 3/1988 | Brown et al. | |
| 4,767,410 A | 8/1988 | Moden et al. | |
| 4,779,763 A | 10/1988 | Klawitter | |
| 4,861,335 A | 8/1989 | Reynolds | |
| 4,883,101 A | 11/1989 | Strong | |
| 4,904,241 A | 2/1990 | Bark | |
| 4,946,778 A | 8/1990 | Ladner et al. | |
| 4,958,622 A | 9/1990 | Selenke | |
| 5,067,948 A | 11/1991 | Haber et al. | |
| 5,197,951 A | 3/1993 | Mahurkar | |
| 5,225,539 A | 7/1993 | Winter | |
| 5,334,163 A | 8/1994 | Sinnett | |
| 5,377,864 A | 1/1995 | Blechl et al. | |
| 5,522,807 A | 6/1996 | Luther | |
| 5,648,237 A | 7/1997 | Carter | |
| 5,704,352 A | 1/1998 | Tremblay et al. | |
| 5,720,720 A | 2/1998 | Laske et al. | |
| 5,736,137 A | 4/1998 | Anderson et al. | |
| 5,810,789 A | 9/1998 | Powers et al. | |
| 5,823,961 A | 10/1998 | Fields et al. | |
| 5,897,528 A | 4/1999 | Schultz | |
| 5,902,331 A | 5/1999 | Bonner et al. | |
| 6,001,806 A | 12/1999 | Hilbert et al. | |
| 6,006,124 A * | 12/1999 | Fischell | A61N 1/0534 |
| | | | 607/116 |
| 6,013,051 A | 1/2000 | Nelson | |
| 6,018,036 A | 1/2000 | Mosmann et al. | |
| 6,086,555 A | 7/2000 | Eliasen et al. | |
| 6,113,578 A | 9/2000 | Brown | |
| 6,248,080 B1 | 6/2001 | Miesel et al. | |
| 6,248,126 B1 | 6/2001 | Lesser et al. | |
| 6,293,922 B1 | 9/2001 | Haase | |
| 6,324,433 B1 | 11/2001 | Errico | |
| 6,451,977 B1 | 9/2002 | De Sauvage et al. | |
| 6,458,943 B1 | 10/2002 | Byrne | |
| 6,475,987 B1 | 11/2002 | Shu | |
| 6,482,185 B1 | 11/2002 | Hartmann | |
| 6,562,023 B1 | 5/2003 | Marrs et al. | |
| 6,573,099 B2 | 6/2003 | Graham | |
| 6,595,979 B1 | 7/2003 | Epstein et al. | |
| 6,632,927 B2 | 10/2003 | Adair et al. | |
| 6,720,138 B2 | 4/2004 | Sharma et al. | |
| 6,753,139 B1 | 6/2004 | Baulcombe et al. | |
| 7,056,704 B2 | 6/2006 | Tuschl et al. | |
| 7,083,785 B2 | 8/2006 | Browning et al. | |
| 7,112,421 B2 | 9/2006 | Ambrose et al. | |
| 7,161,488 B2 | 1/2007 | Frasch | |
| 7,195,616 B2 | 3/2007 | Diller et al. | |
| 7,359,765 B2 | 4/2008 | Varvarelis et al. | |
| 7,371,388 B1 | 5/2008 | Ruben et al. | |
| 7,618,409 B2 | 11/2009 | Hochman | |
| 7,670,327 B2 | 3/2010 | Kucharczyk et al. | |
| 7,883,502 B2 | 2/2011 | Powers et al. | |
| 7,917,222 B1 | 3/2011 | Osorio et al. | |
| 7,922,695 B2 | 4/2011 | Wiegel et al. | |
| 8,066,681 B1 | 11/2011 | Hall et al. | |
| 8,277,425 B2 | 10/2012 | Girard et al. | |
| 8,409,133 B2 | 4/2013 | Pesach et al. | |
| 8,556,866 B2 | 10/2013 | Krulevitch et al. | |
| 8,744,544 B2 | 6/2014 | Najafi et al. | |
| 8,808,234 B2 | 8/2014 | Vogelbaum et al. | |
| 8,827,964 B2 | 9/2014 | Boyd et al. | |
| 8,979,822 B2 | 3/2015 | Vogelbaum et al. | |
| 9,913,960 B2 | 3/2018 | Blanchard et al. | |
| 10,506,988 B2 | 12/2019 | Karoly et al. | |
| 10,716,921 B2 | 7/2020 | Purdy | |
| 10,967,172 B1 | 4/2021 | Shire et al. | |
| 11,504,516 B2 | 11/2022 | Otto | |
| 11,534,592 B2 | 12/2022 | Singh et al. | |
| 12,097,029 B1 | 9/2024 | Shanechi | |
| 2002/0004643 A1 | 1/2002 | Carmel et al. | |
| 2002/0052563 A1 | 5/2002 | Penn et al. | |
| 2002/0086356 A1 | 7/2002 | Tuschl et al. | |
| 2003/0012783 A1 | 1/2003 | Kindsvogel | |
| 2003/0069623 A1 | 4/2003 | Stypulkowski | |
| 2003/0097051 A1 | 5/2003 | Kolberg et al. | |
| 2003/0108923 A1 | 6/2003 | Tuschl et al. | |
| 2003/0135148 A1 | 7/2003 | Dextradeur et al. | |
| 2003/0204075 A9 | 10/2003 | Wang | |
| 2003/0216714 A1 | 11/2003 | Gill | |
| 2003/0228691 A1 | 12/2003 | Lewis et al. | |
| 2004/0002677 A1 | 1/2004 | Gentsler | |
| 2004/0053411 A1 | 3/2004 | Cullen et al. | |
| 2004/0069044 A1 | 4/2004 | Lavi et al. | |
| 2004/0073196 A1 | 4/2004 | Adams et al. | |
| 2004/0082984 A1 | 4/2004 | Osorio et al. | |
| 2004/0086884 A1 | 5/2004 | Beach et al. | |
| 2004/0102412 A1 | 5/2004 | Broschat et al. | |
| 2004/0106566 A1 | 6/2004 | Lin et al. | |
| 2004/0112411 A1 | 6/2004 | Boykin et al. | |
| 2004/0152112 A1 | 8/2004 | Croce et al. | |
| 2004/0171037 A1 | 9/2004 | Li et al. | |
| 2004/0171983 A1 | 9/2004 | Sparks et al. | |
| 2004/0175732 A1 | 9/2004 | Rana | |
| 2004/0210951 A1 | 10/2004 | Baulcombe et al. | |
| 2004/0215162 A1 | 10/2004 | Putz | |
| 2004/0221337 A1 | 11/2004 | Baulcombe et al. | |
| 2004/0229266 A1 | 11/2004 | Tuschl et al. | |
| 2004/0253604 A1 | 12/2004 | Lin et al. | |
| 2004/0259247 A1 | 12/2004 | Tuschl et al. | |
| 2004/0259248 A1 | 12/2004 | Tuschl et al. | |
| 2004/0268441 A1 | 12/2004 | Vance et al. | |
| 2005/0004219 A1 | 1/2005 | Hildebrand et al. | |
| 2005/0026278 A1 | 2/2005 | Tuschl et al. | |
| 2005/0037988 A1 | 2/2005 | Zamore et al. | |
| 2005/0038371 A1 | 2/2005 | Reich et al. | |
| 2005/0059005 A1 | 3/2005 | Tuschl et al. | |
| 2005/0059011 A1 | 3/2005 | Sin et al. | |
| 2005/0070458 A1 | 3/2005 | John | |
| 2005/0074788 A1 | 4/2005 | Dahlberg et al. | |
| 2005/0075492 A1 | 4/2005 | Chen et al. | |
| 2005/0079614 A1 | 4/2005 | Reinhart et al. | |
| 2005/0137578 A1 | 6/2005 | Heruth et al. | |
| 2005/0163775 A1 | 7/2005 | Chan et al. | |
| 2005/0209332 A1 | 9/2005 | Kuppuswamy et al. | |
| 2005/0228315 A1 | 10/2005 | Ayad | |
| 2005/0245906 A1 | 11/2005 | Makower et al. | |
| 2006/0004317 A1 | 1/2006 | Mauge et al. | |
| 2006/0067933 A1 | 3/2006 | Gross et al. | |
| 2006/0073146 A1 | 4/2006 | Ashkenazi et al. | |
| 2006/0079834 A1 | 4/2006 | Tennican et al. | |
| 2006/0084055 A1 | 4/2006 | Gaiger et al. | |
| 2006/0122677 A1 | 6/2006 | Vardiman | |
| 2006/0160889 A1 | 7/2006 | Veeneman et al. | |
| 2006/0286093 A1 | 12/2006 | Gross et al. | |
| 2007/0073228 A1 | 3/2007 | Mernoe et al. | |
| 2007/0078438 A1 | 4/2007 | Okada | |
| 2007/0083063 A1 | 4/2007 | Nelson et al. | |
| 2007/0086979 A1 | 4/2007 | Chevrier et al. | |
| 2007/0123758 A1 | 5/2007 | Miesel et al. | |
| 2007/0185017 A1 | 8/2007 | Aggarwal et al. | |
| 2007/0197957 A1 | 8/2007 | Hunter et al. | |
| 2007/0255237 A1 | 11/2007 | Lobl et al. | |
| 2007/0260375 A1 | 11/2007 | Hilton | |
| 2008/0027346 A1 | 1/2008 | Litt et al. | |
| 2008/0039774 A1 | 2/2008 | Zawacki et al. | |
| 2008/0058476 A1 | 3/2008 | Whiteker et al. | |
| 2008/0132980 A1 | 6/2008 | Gerber | |
| 2008/0147006 A1 | 6/2008 | Brunnberg et al. | |
| 2008/0262374 A1 | 10/2008 | Gerber et al. | |
| 2009/0030480 A1 | 1/2009 | Durand et al. | |
| 2009/0069267 A1 | 3/2009 | Abrams et al. | |
| 2009/0069742 A1 | 3/2009 | Larsen | |
| 2009/0112327 A1 | 4/2009 | Lane et al. | |
| 2009/0131850 A1 | 5/2009 | Geiger | |
| 2009/0131857 A1 | 5/2009 | Geiger | |
| 2009/0137944 A1 | 5/2009 | Haarala et al. | |

(56) References Cited

U.S. PATENT DOCUMENTS

| | | |
|---|---|---|
| 2009/0203983 A1 | 8/2009 | Carlton et al. |
| 2009/0228066 A1 | 9/2009 | Hirata et al. |
| 2010/0036477 A1 | 2/2010 | Bronson et al. |
| 2010/0089167 A1 | 4/2010 | Trieu et al. |
| 2010/0145162 A1 | 6/2010 | Devauchelle et al. |
| 2010/0145176 A1 | 6/2010 | Himes |
| 2010/0158869 A1 | 6/2010 | Kaemmerer |
| 2010/0168532 A1 | 7/2010 | Waziri et al. |
| 2010/0210958 A1 | 8/2010 | Manwaring et al. |
| 2010/0241088 A1 | 9/2010 | Ranalletta et al. |
| 2010/0280335 A1 | 11/2010 | Carlson et al. |
| 2010/0286585 A1 | 11/2010 | Dimauro et al. |
| 2010/0305492 A1 | 12/2010 | Lad et al. |
| 2011/0009821 A1 | 1/2011 | Jespersen et al. |
| 2011/0009933 A1 | 1/2011 | Barker |
| 2011/0033463 A1 | 2/2011 | Thakker et al. |
| 2011/0066072 A1 | 3/2011 | Kawoos et al. |
| 2011/0092921 A1 | 4/2011 | Beling et al. |
| 2011/0172633 A1 | 7/2011 | Ali et al. |
| 2011/0201944 A1 | 8/2011 | Higgins et al. |
| 2011/0257596 A1 | 10/2011 | Gaudet |
| 2011/0264033 A1 | 10/2011 | Jensen et al. |
| 2011/0270095 A1 | 11/2011 | Bukhman |
| 2011/0270230 A1 | 11/2011 | Sage et al. |
| 2011/0275930 A1 | 11/2011 | Jho et al. |
| 2012/0015336 A1 | 1/2012 | Mach |
| 2012/0087869 A1 | 4/2012 | Thakker et al. |
| 2012/0245529 A1 | 9/2012 | Hummen et al. |
| 2012/0290225 A1 | 11/2012 | Julian et al. |
| 2012/0296271 A1 | 11/2012 | Yomtov et al. |
| 2012/0296404 A1 | 11/2012 | Carpentier et al. |
| 2012/0302959 A1 | 11/2012 | Fielder et al. |
| 2012/0310140 A1 | 12/2012 | Kramer et al. |
| 2013/0204229 A1 | 8/2013 | Olson et al. |
| 2013/0253266 A1 | 9/2013 | Dextradeur et al. |
| 2013/0267928 A1 | 10/2013 | Imran et al. |
| 2013/0324945 A1 | 12/2013 | Sabin |
| 2014/0012209 A1 | 1/2014 | Sansoucy |
| 2014/0074060 A1 | 3/2014 | Imran |
| 2014/0081347 A1 | 3/2014 | Nelson et al. |
| 2014/0148780 A1 | 5/2014 | Putz |
| 2014/0194825 A1 | 7/2014 | Nielsen et al. |
| 2014/0207074 A1 | 7/2014 | Nielsen |
| 2014/0236259 A1 | 8/2014 | Colantonio |
| 2014/0249410 A1 | 9/2014 | Uber, III et al. |
| 2014/0257168 A1 | 9/2014 | Gill |
| 2014/0276416 A1 | 9/2014 | Nelson et al. |
| 2015/0038901 A1 | 2/2015 | Lampropoulos et al. |
| 2015/0202373 A1 | 7/2015 | Creaturo |
| 2015/0209505 A1 | 7/2015 | Hanson et al. |
| 2015/0230724 A1 | 8/2015 | Waziri et al. |
| 2015/0238685 A1 | 8/2015 | Elias et al. |
| 2015/0297874 A1 | 10/2015 | East et al. |
| 2015/0306302 A1 | 10/2015 | Marsden et al. |
| 2015/0367067 A1 | 12/2015 | Minaie et al. |
| 2016/0122282 A1 | 5/2016 | Kandula |
| 2016/0213312 A1 | 7/2016 | Singh et al. |
| 2016/0374901 A9 | 12/2016 | Rodriguez et al. |
| 2017/0007621 A1 | 1/2017 | Wotton et al. |
| 2017/0173267 A1 | 6/2017 | Ashmead et al. |
| 2017/0325685 A1 | 11/2017 | Shachar et al. |
| 2017/0365101 A1 | 12/2017 | Samec et al. |
| 2018/0028746 A1 | 2/2018 | Abrams et al. |
| 2018/0028824 A1 | 2/2018 | Pivonka et al. |
| 2018/0104459 A1 | 4/2018 | Anand et al. |
| 2018/0107798 A1 | 4/2018 | Hu |
| 2018/0107998 A1 | 4/2018 | Pederson |
| 2018/0140810 A1 | 5/2018 | Cataltepe |
| 2018/0193562 A1 | 7/2018 | Gibson et al. |
| 2018/0263752 A1 | 9/2018 | Pinchuk et al. |
| 2019/0030322 A1* | 1/2019 | Schulte ............... A61N 1/0539 |
| 2019/0082990 A1 | 3/2019 | Poltorak |
| 2019/0105019 A1 | 4/2019 | Pagoulatos et al. |
| 2019/0151239 A1 | 5/2019 | Abrams et al. |
| 2019/0167964 A1 | 6/2019 | Lewis et al. |
| 2019/0218334 A1 | 7/2019 | Delaney, Jr. et al. |
| 2019/0246989 A1 | 8/2019 | Genov et al. |
| 2019/0282802 A1 | 9/2019 | Malinowski |
| 2019/0321106 A1 | 10/2019 | Bergman et al. |
| 2019/0351209 A1 | 11/2019 | Butziger et al. |
| 2020/0061337 A1 | 2/2020 | Singh et al. |
| 2020/0069254 A1 | 3/2020 | Lange et al. |
| 2020/0086538 A1 | 3/2020 | Funaoka |
| 2020/0170542 A1 | 6/2020 | Waziri et al. |
| 2020/0338325 A1 | 10/2020 | Shachar et al. |
| 2020/0375492 A1 | 12/2020 | Govari |
| 2021/0077714 A1 | 3/2021 | Bodner |
| 2021/0100990 A1 | 4/2021 | Yoo et al. |
| 2021/0205623 A1 | 7/2021 | Peterson et al. |
| 2021/0252266 A1 | 8/2021 | Otto |
| 2021/0260280 A1 | 8/2021 | Gordon et al. |
| 2021/0327029 A1 | 10/2021 | Chen et al. |
| 2021/0338992 A1 | 11/2021 | Bertrand |
| 2021/0386982 A1 | 12/2021 | Lad et al. |
| 2021/0397970 A1 | 12/2021 | Cherian et al. |
| 2022/0016338 A1 | 1/2022 | Abrams et al. |
| 2022/0016402 A1 | 1/2022 | Abrams et al. |
| 2022/0016404 A1 | 1/2022 | Abrams et al. |
| 2022/0022800 A1 | 1/2022 | Abrams et al. |
| 2022/0249190 A1 | 8/2022 | Kelly et al. |
| 2022/0331567 A1 | 10/2022 | Abrams |
| 2023/0148923 A1 | 5/2023 | Abrams et al. |
| 2023/0200707 A1 | 6/2023 | Abrams et al. |
| 2023/0277840 A1 | 9/2023 | Abrams et al. |
| 2024/0021313 A1 | 1/2024 | Alkaitis et al. |

FOREIGN PATENT DOCUMENTS

| | | |
|---|---|---|
| DE | 102013002763 A1 | 8/2014 |
| EP | 0904119 A1 | 3/1999 |
| EP | 0995460 A2 | 4/2000 |
| EP | 1281758 A2 | 2/2003 |
| EP | 1391219 A2 | 2/2004 |
| EP | 1391219 A3 | 5/2004 |
| EP | 1798243 A2 | 6/2007 |
| EP | 3028727 A1 | 6/2016 |
| JP | 2004533997 A | 11/2004 |
| JP | 2007309746 A | 11/2007 |
| KR | 102054445 B1 | 12/2019 |
| WO | 9406690 A1 | 3/1994 |
| WO | 9427587 A2 | 12/1994 |
| WO | 96033761 A1 | 10/1996 |
| WO | 0040716 A2 | 7/2000 |
| WO | 0068378 A1 | 11/2000 |
| WO | 0160397 A1 | 8/2001 |
| WO | 0168836 A2 | 9/2001 |
| WO | 0175164 A2 | 10/2001 |
| WO | 0244321 A2 | 6/2002 |
| WO | 02066516 A2 | 8/2002 |
| WO | 02094185 A2 | 11/2002 |
| WO | 03013582 A1 | 2/2003 |
| WO | 03029459 A2 | 4/2003 |
| WO | 03062401 A2 | 7/2003 |
| WO | 03070884 A2 | 8/2003 |
| WO | 03070903 A2 | 8/2003 |
| WO | 03070918 A2 | 8/2003 |
| WO | 03072713 A2 | 9/2003 |
| WO | 03074566 A2 | 9/2003 |
| WO | 03074654 A2 | 9/2003 |
| WO | 2004009779 A2 | 1/2004 |
| WO | 2004031412 A2 | 4/2004 |
| WO | 2004039956 A2 | 5/2004 |
| WO | 2004057017 A2 | 7/2004 |
| WO | 2004066183 A2 | 8/2004 |
| WO | 2004072248 A2 | 8/2004 |
| WO | 2004111191 A2 | 12/2004 |
| WO | 2004112411 A1 | 12/2004 |
| WO | 2005000351 A2 | 1/2005 |
| WO | 2005012523 A1 | 2/2005 |
| WO | 2005017111 A2 | 2/2005 |
| WO | 2005019453 A2 | 3/2005 |
| WO | 2005023986 A2 | 3/2005 |
| WO | WO-2005023200 A2 * | 3/2005 | ............... A61F 7/12 |
| WO | 2005033271 A2 | 4/2005 |

(56)                    References Cited

FOREIGN PATENT DOCUMENTS

| WO | 2005035769 A2 | 4/2005 |
|---|---|---|
| WO | 2005041859 A2 | 5/2005 |
| WO | 2005042705 A2 | 5/2005 |
| WO | 2006068867 A1 | 6/2006 |
| WO | 2007019618 A1 | 2/2007 |
| WO | 2007070538 A2 | 6/2007 |
| WO | 2008112017 A2 | 9/2008 |
| WO | 2008115919 A2 | 9/2008 |
| WO | 2008141321 A1 | 11/2008 |
| WO | 2009014762 A1 | 1/2009 |
| WO | 2009024562 A1 | 2/2009 |
| WO | 2009151741 A1 | 12/2009 |
| WO | 2010056712 A1 | 5/2010 |
| WO | 2011097487 A2 | 8/2011 |
| WO | 2013004843 A1 | 1/2013 |
| WO | 2014064691 A2 | 5/2014 |
| WO | 2014159757 A2 | 10/2014 |
| WO | 2014188407 A1 | 11/2014 |
| WO | 2015001008 A1 | 1/2015 |
| WO | 2015197867 A1 | 12/2015 |
| WO | 2016140853 A1 | 9/2016 |
| WO | 2018023041 A1 | 2/2018 |
| WO | 2018038930 A1 | 3/2018 |
| WO | 2018153943 A1 | 8/2018 |
| WO | 2019084038 A1 | 5/2019 |
| WO | 2019136462 A1 | 7/2019 |
| WO | 2019211314 A1 | 11/2019 |
| WO | 2020160613 A1 | 8/2020 |
| WO | 2020248067 A1 | 12/2020 |
| WO | 2021150522 A1 | 7/2021 |
| WO | 2022015941 A1 | 1/2022 |
| WO | 2022020314 A1 | 1/2022 |

OTHER PUBLICATIONS

Gaudilliere et al., "RNA interference reveals a requirement for myocyte enhancer factor 2A in activity-dependent neuronal survival." Journal of Biological Chemistry 277.48 (2002): 46442-46446.

Ge et al., "Inhibition of influenza virus production in virus-infected mice by RNA interference." Proceedings of the National Academy of Sciences 101.23 (2004): 8676-8681.

Gebauer et al., "Molecular mechanisms of translational control." Nature reviews Molecular cell biology 5.10 (2004): 827-835.

Gernert et al., "Bypassing the blood-brain barrier: direct intracranial drug delivery in epilepsies." Pharmaceutics 12.12 (2020): 1-39.

Gershon D., "Microarrays go mainstream." Nature Methods 1.3 (2004): 263-270.

Geuze et al., "Reduced GABAA benzodiazepine receptor binding in veterans with post-traumatic stress disorder." Molecular psychiatry 13.1 (2008): 74-83.

Ghosal et al., "Prefrontal cortex GABAergic deficits and circuit dysfunction in the pathophysiology and treatment of chronic stress and depression." Current opinion in behavioral sciences 14 (2017): 1-8.

Ghosh et al., "Functional connectivity from the amygdala to the hippocampus grows stronger after stress." Journal of Neuroscience 33.17 (2013): 7234-7244.

Gibbs W., "The unseen genome: beyond DNA." Scientific American 289.6 (2003): 106-113.

Gibbs W., "The unseen genome: gems among the junk." Scientific American 289.5 (2003): 46-53.

Giordano et al., "RNAi triggered by symmetrically transcribed transgenes in Drosophila melanogaster." Genetics 160.2 (2002): 637-648.

Giraldez et al., "MicroRNAs regulate brain morphogenesis in zebrafish." Science 308.5723 (2005): 833-838.

Gitlin et al., "Poliovirus escape from RNA interference: short interfering RNA-target recognition and implications for therapeutic approaches." Journal of virology 79.2 (2005): 1027-1035.

Golden et al., "Short INTEGUMENTS1/SUSPENSOR1/CARPEL Factory, a Dicer homolog, is a maternal effect gene required for embryo development in Arabidopsis." Plant Physiology 130.2 (2002): 808-822.

Gooch et al., "Recognition of Duplex RNA by Helix-Threading Peptides." Journal of the American Chemical Society 126.34 (2004): 10603-10610.

Gottesman S., "Stealth regulation: biological circuits with small RNA switches." Genes & development 16.22 (2002): 2829-2842.

Grad et al., "Computational and experimental identification of C. elegans microRNAs." Molecular cell 11.5 (2003): 1253-1263.

Gradus et al., "Associations between stress disorders and cardiovascular disease events in the Danish population." BMJ open 5.12 (2015): 1-7.

Gradus et al., "Posttraumatic stress disorder and completed suicide." American journal of epidemiology 171.6 (2010): 721-727.

Gradus J., "Prevalence and prognosis of stress disorders: a review of the epidemiologic literature." Clinical epidemiology (2017): 251-260.

Gras et al., "BCMAp: an integral membrane protein in the Golgi apparatus of human mature B lymphocytes." International immunology 7.7 (1995): 1093-1106.

Gregory et al., "MicroRNA biogenesis and cancer." Cancer research 65.9 (2005): 3509-3512.

Gregory et al., "The Microprocessor complex mediates the genesis of microRNAs." Nature 432.7014 (2004): 235-240.

Grey et al., "Cognitive restructuring within reliving: A treatment for peritraumatic emotional "hotspots" in posttraumatic stress disorder." Behavioural and cognitive psychotherapy 30.1 (2002): 37-56.

Griffiths-Jones S., "The microRNA registry." Nucleic acids research 32 (2004): D109-D111.

Grisaru et al., "Structural roles of acetylcholinesterase variants in biology and pathology." European Journal of Biochemistry 264.3 (1999): 672-686.

Grishok et al., "Genes and mechanisms related to RNA interference regulate expression of the small temporal RNAs that control C. elegans developmental timing." Cell 106.1 (2001): 23-34.

Grosshans et al., "Micro-RNAs: small is plentiful." The Journal of cell biology 156.1 (2002): 17-22.

Großhans et al., "The temporal patterning microRNA let-7 regulates several transcription factors at the larval to adult transition in C. elegans." Developmental cell 8.3 (2005): 321-330.

Guarguaglini et al., "The forkhead-associated domain protein Cep170 interacts with Polo-like kinase 1 and serves as a marker for mature centrioles." Molecular biology of the cell 16.3 (2005): 1095-1107.

Gupta et al., "Directly labeled mRNA produces highly precise and unbiased differential gene expression data." Nucleic acids research 31.4 (2003): 1-6.

Gustafson et al., "ASRP: the Arabidopsis small RNA project database." Nucleic acids research 33 (2005): D637-D640.

Hake S., "MicroRNAs: a role in plant development." Current Biology 13.21 (2003): R851-R852.

Hall J., "Unravelling the general properties of siRNAs: strength in Nos. and lessons from the past." Nature Reviews Genetics 5.7 (2004): 552-557.

Hamann et al., "Amygdala activity related to enhanced memory for pleasant and aversive stimuli." Nature neuroscience 2.3 (1999): 289-293.

Hamilton et al., "Two classes of short interfering RNA in RNA silencing." The EMBO journal 21.17 (2002): 4671-4679.

Hammond et al., "An RNA-directed nuclease mediates post-transcriptional gene silencing in Drosophila cells." Nature 404.6775 (2000): 293-296.

Hammond et al., "Argonaute2, a link between genetic and biochemical analyses of RNAi." Science 293.5532 (2001): 1146-1150.

Han et al., "Relationship between small antisense RNAs and aberrant RNAs associated with sense transgene mediated gene silencing in tomato." The Plant Journal 29.4 (2002): 509-519.

Han et al., "The Arabidopsis double-stranded RNA-binding protein HYL1 plays a role in microRNA-mediated gene regulation." Proceedings of the National Academy of Sciences 101.4 (2004): 1093-1098.

(56)                    References Cited

OTHER PUBLICATIONS

Han et al., "The Drosha-DGCR8 complex in primary microRNA processing." Genes & development 18.24 (2004): 3016-3027.
Hannon G., "RNA interference." nature 418.6894 (2002): 244-251.
Hansen et al., "Global effects on gene expression in fission yeast by silencing and RNA interference machineries." Molecular and cellular biology 25.2 (2005): 590-601.
Hardy J., "Toward Alzheimer therapies based on genetic knowledge." Annu. Rev. Med. 55.1 (2004): 15-25.
Harlow et al., "Using Antibodies: A Laboratory Manual." Cold Spring Harbor Laboratory (1998) 1-3.
Harrell E., "Neuromarketing: What you need to know." Harvard Business Review 97.4 (2019): 64-70.
Harris et al., "Effects of benzodiazepine microinjection into the amygdala or periaqueductal gray on the expression of conditioned fear and hypoalgesia in rats." Behavioral neuroscience 109.2 (1995): 295-304.
Hartig et al., "Sequence-specific detection of MicroRNAs by signal-amplifying ribozymes." Journal of the American Chemical Society 126.3 (2004): 722-723.
Hatzoglou et al., "TNF receptor family member BCMA (B cell maturation) associates with TNF receptor-associated factor (TRAF) 1, TRAF2, and TRAF3 and activates NF-KB, elk-1, c-Jun N-terminal kinase, and p38 mitogen-activated protein kinase." The Journal of Immunology 165.3 (2000): 1322-1330.
Hayase T., "Putative epigenetic involvement of the endocannabinoid system in anxiety-and depression-related behaviors caused by nicotine as a stressor." PLoS One 11.7 (2016): 1-21.
Novak et al., "Expression of Bcma, Taci, and BAFF-R in multiple myeloma: a mechanism for growth and survival." Blood 103.2 (2004): 689-694.
Novak et al., "Expression of BLyS and its receptors in B-cell non-Hodgkin lymphoma: correlation with disease activity and patient outcome." Blood 104.8 (2004): 2247-2253.
Novina et al., "siRNA-directed inhibition of HIV-1 infection." Nature medicine 8.7 (2002): 681-686.
Novina et al., "The rnai revolution." Nature 430.6996 (2004): 161-164.
O'Connor et al., "BCMA is essential for the survival of long-lived bone marrow plasma cells." The Journal of experimental medicine 199.1 (2004): 91-98.
O'Loghlen et al., "Suppression of human Mnk1 by small interfering RNA increases the eukaryotic initiation factor 4F activity in HEK293T cells." FEBS letters 578.1-2 (2004): 31-35.
O'Toole et al., "Stability of 3' double nucleotide overhangs that model the 3' ends of siRNA." Rna 11.4 (2005): 512-516.
Ogita et al., "Application of RNAi to confirm theobromine as the major intermediate for caffeine biosynthesis in coffee plants with potential for construction of decaffeinated varieties." Plant molecular biology 54.6 (2004): 931-941.
Ohler et al., "Patterns of flanking sequence conservation and a characteristic upstream motif for microRNA gene identification." Rna 10.9 (2004): 1309-1322.
Ohno et al., "BACE1 deficiency rescues memory deficits and cholinergic dysfunction in a mouse model of Alzheimer's disease." Neuron 41.1 (2004): 27-33.
Okamura et al., "Distinct roles for Argonaute proteins in small RNA-directed RNA cleavage pathways." Genes & development 18.14 (2004): 1655-1666.
Okazaki et al., "FANTOM Consortium; RIKEN Genome Exploration Research Group Phase I & II Team. Analysis of the mouse transcriptome based on functional annotation of 60,770 full-length cDNAs." (2002): 563-573.
Olsen et al., "The lin-4 regulatory RNA controls developmental timing in Caenorhabditis elegans by blocking LIN-14 protein synthesis after the initiation of translation." Developmental biology 216.2 (1999): 671-680.
Omoto et al., "HIV-1 nef suppression by virally encoded microRNA." Retrovirology 1.1 (2004): 1-12.

Omoto et al., "Regulation of human immunodeficiency virus 1 transcription by nef microRNA." Journal of General Virology 86.3 (2005): 751-755.
Onishi et al., "Withdrawn: Molecular evolution of a microRNA cluster in the PWS/AS region among mammals." (2005): 1-1.
Opdyke et al., "GadY, a small-RNA regulator of acid response genes in Escherichia coli." Journal of bacteriology 186.20 (2004): 6698-6705.
Orban et al., "Decay of mRNAs targeted by RISC requires XRN1, the Ski complex, and the exosome." Rna 11.4 (2005): 459-469.
Ostberg et al., "The etiological agent of Lyme disease, Borrelia burgdorferi, appears to contain only a few small RNA molecules." Journal of bacteriology 186.24 (2004): 8472-8477.
Osuch et al., "Regional cerebral blood flow correlated with flashback intensity in patients with posttraumatic stress disorder." Biological psychiatry 50.4 (2001): 246-253.
Ota et al., "Complete sequencing and characterization of 21,243 full-length human cDNAs." Nature genetics 36.1 (2004): 40-45.
Ota et al., "Identification and characterization of a novel gene, C13orf25, as a target for 13q31-q32 amplification in malignant lymphoma." Cancer research 64.9 (2004): 3087-3095.
Otte et al., "Valproate monotherapy in the treatment of civilian patients with non-combat-related posttraumatic stress disorder: an open-label study." Journal of clinical psychopharmacology 24.1 (2004): 106-108.
Overhoff et al., "Local RNA target structure influences siRNA efficacy: a systematic global analysis." Journal of molecular biology 348.4 (2005): 871-881.
Paddison et al., "Short hairpin RNAs (shRNAs) induce sequence-specific silencing in mammalian cells." Genes & development 16.8 (2002): 948-958.
Paddison et al., "Stable suppression of gene expression by RNAi in mammalian cells." Proceedings of the National Academy of Sciences 99.3 (2002): 1443-1448.
Padlan et al., "Structure of an antibody-antigen complex: crystal structure of the HyHEL-10 Fab-lysozyme complex." Proceedings of the National Academy of Sciences 86. 15 (1989): 5938-5942.
Palatnik et al., "Control of leaf morphogenesis by microRNAs." Nature 425.6955 (2003): 257-263.
Panagioti et al., "Post-traumatic stress disorder and suicidal behavior: A narrative review." Clinical psychology review 29.6 (2009): 471-482.
Pang et al., "RNAdb-a comprehensive mammalian noncoding RNA database." Nucleic acids research 33.suppl_1 (2005): D125-D130.
Parizotto et al., "In vivo investigation of the transcription, processing, endonucleolytic activity, and functional relevance of the spatial distribution of a plant miRNA." Genes & development 18.18 (2004): 2237-2242.
Park et al., "Carpel Factory, a Dicer homolog, and HEN1, a novel protein, act in microRNA metabolism in Arabidopsis thaliana." Current biology 12.17 (2002): 1484-1495.
Parker et al., "Sequence and transcription of Raji Epstein-Barr virus DNA spanning the B95-8 deletion region." Virology 179.1 (1990): 339-346.
Pasquinelli et al., "Conservation of the sequence and temporal expression of let-7 heterochronic regulatory RNA." Nature 408. 6808 (2000): 86-89.
Pasquinelli et al., "Control of developmental timing by microRNAs and their targets." Annual review of cell and developmental biology 18.1 (2002): 495-513.
Pasquinelli et al., "MicroRNAs: a developing story." Current opinion in genetics & development 15.2 (2005): 200-205.
Pasquinelli, A. "MicroRNAs: deviants no longer." TRENDS in Genetics 18.4 (2002): 171-173.
Paykel, E. "Achieving gains beyond response." Acta Psychiatrica Scandinavica 106 (2002): 12-17.
Pearson et al., "Creation of "humanized" mice to study human immunity." Current protocols in immunology 81.1 (2008): 15-21.
Perumal et al., "Inhibitory circuits in the basolateral amygdala in aversive learning and memory." Frontiers in Neural Circuits 15 (2021): 633235.
Pfeffer et al., "Identification of microRNAs of the herpesvirus family." Nature methods 2.4 (2005): 269-276.

(56)  References Cited

OTHER PUBLICATIONS

Pfeffer et al., "Identification of virus-encoded microRNAs." Science 304.5671 (2004): 734-736.
Piccin et al., "Efficient and heritable functional knock-out of an adult phenotype in Drosophila using a GAL4-driven hairpin RNA incorporating a heterologous spacer." Nucleic acids research 29.12 (2001): 1-5.
Pillai et al., "Tethering of human Ago proteins to mRNA mimics the miRNA-mediated repression of protein synthesis." Rna 10.10 (2004): 1518-1525.
Pissiota et al., "Neurofunctional correlates of posttraumatic stress disorder: a PET symptom provocation study." European archives of psychiatry and clinical neuroscience 252.2 (2002): 68-75.
Pitt et al., "P granules in the germ cells of Caenorhabditis elegans adults are associated with clusters of nuclear pores and contain RNA." Developmental biology 219.2 (2000): 315-333.
Pocivavsek et al., "Fluctuations in endogenous kynurenic acid control hippocampal glutamate and memory." Neuropsychopharmacology 36.11 (2011): 2357-2367.
Pomerantz et al., "Two pathways to NF-KB." Molecular cell 10.4 (2002): 693-695.
Pomerantz R., "RNA interference meets HIV-1: will silence be golden." Nature Medicine 8.7 (2002): 659-660.
Ponniah et al., "Empirically supported psychological treatments for adult acute stress disorder and posttraumatic stress disorder: a review." Depression and anxiety 26.12 (2009): 1086-1109.
He et al., ""siRNAs and miRNAs": A meeting report on RNA silencing." RNA (2004): 1165-1173.
He et al., "Lymphoma B cells evade apoptosis through the TNF family members BAFF/BLyS and APRIL." The Journal of Immunology 172.5 (2004): 3268-3279.
He et al., "MicroRNAs: small RNAs with a big role in gene regulation." Nature reviews genetics 5.7 (2004): 522-531.
Heetebrij et al., "Platinum (II)-Based Coordination Compounds as Nucleic Acid Labeling Reagents: Synthesis, Reactivity, and Applications in Hybridization Assays." Chembiochem 4.7 (2003): 573-583.
Hemming et al., "The stepped wedge cluster randomised trial: rationale, design, analysis, and reporting." Bmj 350 (2015): 1-7.
Henigsberg et al., "Neuroimaging research in posttraumatic stress disorder-Focus on amygdala, hippocampus and prefrontal cortex." Progress in Neuro-Psychopharmacology and Biological Psychiatry 90 (2019): 37-42.
Hershberg et al., "A survey of small RNA-encoding genes in Escherichia coli." Nucleic acids research 31.7 (2003): 1813-1820.
Hertzberg et al., "A preliminary study of lamotrigine for the treatment of posttraumatic stress disorder." Biological psychiatry 45.9 (1999): 1226-1229.
Hipfner et al., "The bantam gene regulates Drosophila growth." Genetics 161.4 (2002): 1527-1537.
Hobert O., "Common logic of transcription factor and microRNA action." Trends in biochemical sciences 29.9 (2004): 462-468.
Hobert O., "MicroRNAs: all gone and then what." Current Biology 15.10 (2005): R387-R389.
Hofacker et al., "Prediction of locally stable RNA secondary structures for genome-wide surveys." Bioinformatics 20.2 (2004): 186-190.
Holt et al., "Domain antibodies: proteins for therapy." Trends in biotechnology 21.11 (2003): 484-490.
Holway et al., "Systematic, RNA-interference-mediated identification of mus-101 modifier genes in Caenorhabditis elegans." Genetics 169.3 (2005): 1451-1460.
Hooper et al., "The search for a-secretase and its potential as a therapeutic approach to Alzheimer's disease." Current medicinal chemistry 9.11 (2002): 1107-1119.
Houbaviy et al., "Embryonic stem cell-specific MicroRNAs." Developmental cell 5.2 (2003): 351-358.
Howard et al., "Efficient stimulation of site-specific ribosome frameshifting by antisense oligonucleotides." Rna 10.10 (2004): 1653-1661.

Huang et al., "CPEC induces erythroid differentiation of human myeloid leukemia K562 cells through CTP depletion and p38 MAP kinase." Leukemia 18.11 (2004): 1857-1863.
Huang et al., "Homeostatic cell-cycle control by BLyS: Induction of cell-cycle entry but not G1/S transition in opposition to p18INK4c and p27Kip1." Proceedings of the National Academy of Sciences 101.51 (2004): 17789-17794.
Hughes et al., "Functional neuroimaging studies of post-traumatic stress disorder." Expert review of neurotherapeutics 11.2 (2011): 275-285.
Huhn et al., "Efficacy of pharmacotherapy and psychotherapy for adult psychiatric disorders: a systematic overview of meta-analyses." JAMA psychiatry 71.6 (2014): 706-715.
Human herpesvirus 4 complete wild type genome, XP002500227. Retrieved from EBI Database accession No. AJ507799 (2002).
Huppi et al., "Defining and assaying RNAi in mammalian cells." Molecular cell 17.1 (2005): 1-10.
Huse et al., "Generation of a large combinatorial library of the immunoglobulin repertoire in phage lambda." Science 246.4935 (1989): 1275-1281.
Huttenhofer et al., "RNomics: identification and function of small, non-messenger RNAs." Current opinion in chemical biology 6.6 (2002): 835-843.
Hutvagner et al., "A cellular function for the RNA-interference enzyme Dicer in the maturation of the let-7 small temporal RNA." Science 293.5531 (2001): 834-838.
Hutvagner et al., "A microRNA in a multiple-turnover RNAi enzyme complex." Science 297.5589 (2002): 2056-2060.
Hutvagner et al., "RNAi: nature abhors a double-strand." Current opinion in genetics & development 12.2 (2002): 225-232.
Hutvagner et al., "Sequence-specific inhibition of small RNA function." PLOS biology 2.4 (2004): 465-475.
Hydrocephalus and Shunts, Ausmed. com, Retrieved from the Internet: <URL: https://www.ausmed.com/cpd/articles/hydrocephalus-and-shunts> (2023): 1-6.
International Preliminary Report on Patentability in PCT/US2016/019523, mailed Sep. 5, 2017, 12 pages.
International Preliminary Report on Patentability in PCT/US2017/013881, mailed Jul. 24, 2018, 6 pages.
International Preliminary Report on Patentability in PCT/US2018/014387, mailed Jul. 23, 2019, 8 pages.
International Preliminary Report on Patentability in PCT/US2019/068592, mailed Jun. 16, 2021, 9 pages.
International Preliminary Report on Patentability in PCT/US2021/042315, mailed Oct. 4, 2022, 6 pages.
International Preliminary Report on Patentability in PCT/US2021/042351, mailed Oct. 28, 2022, 11 pages.
International Preliminary Report on Patentability in PCT/US2022/054049, mailed Jan. 24, 2024, 7 pages.
International Preliminary Report on Patentability in PCT/US2023/021974, mailed Nov. 7, 2024, 9 pages.
International Preliminary Report on Patentability in PCT/US2023/036432, mailed Apr. 29, 2025, 9 pages.
International Search Report and Written Opinion in PCT/US2016/019523, mailed Jun. 30, 2016, 15 pages.
International Search Report and Written Opinion in PCT/US2017/013881, mailed May 3, 2017, 9 pages.
International Search Report and Written Opinion in PCT/US2017/044452, mailed Nov. 2, 2017, 15 pages.
International Search Report and Written Opinion in PCT/US2018/014387, mailed Apr. 9, 2018, 11 pages.
International Search Report and Written Opinion in PCT/US2019/068592, mailed Apr. 24, 2020, 12 pages.
International Search Report and Written Opinion in PCT/US2021/041763, mailed Nov. 15, 2021, 15 pages.
International Search Report and Written Opinion in PCT/US2021/041766, mailed Nov. 25, 2021, 14 pages.
International Search Report and Written Opinion in PCT/US2021/041772, mailed Nov. 17, 2021, 14 pages.
International Search Report and Written Opinion in PCT/US2021/042315, mailed Oct. 8, 2021, 10 pages.
International Search Report and Written Opinion in PCT/US2021/042351, mailed Oct. 25, 2021, 13 pages.

(56) References Cited

OTHER PUBLICATIONS

International Search Report and Written Opinion in PCT/US2022/047860, mailed Feb. 17, 2023, 8 pages.

Max et al., "The lifetime cost of injury." Inquiry (1990): 332-343.

McCaffrey et al., "RNA interference in adult mice." Nature 418. 6893 (2002): 38-39.

McHale et al., "MicroRNA-directed cleavage of Nicotiana sylvestris PHAVOLUTA mRNA regulates the vascular cambium and structure of apical meristems." The Plant Cell 16.7 (2004): 1730-1740.

McManus et al., "Gene silencing using micro-RNA designed hairpins." Rna 8.6 (2002): 842-850.

McManus, M. "MicroRNAs and cancer." Seminars in cancer biology. vol. 13. No. 4. Academic Press (2003): 253-258.

Mehta et al., "EEG abnormalities in children with speech and language impairment." Journal of Clinical and Diagnostic Research: JCDR 9.7 (2015): CC04-CC07.

Meister et al., "Human Argonaute2 mediates RNA cleavage targeted by miRNAs and siRNAs." Molecular cell 15.2 (2004): 185-197.

Meister et al., "Mechanisms of gene silencing by double-stranded RNA." Nature 431.7006 (2004): 343-349.

Meister et al., "Sequence-specific inhibition of microRNA-and siRNA-induced RNA silencing." Rna 10.3 (2004): 544-550.

Merkle et al., "Biological significance of a human enterovirus B-specific RNA element in the 3' nontranslated region." Journal of virology 76.19 (2002): 9900-9909.

Meshorer et al., "Alternative splicing and neuritic mRNA translocation under long-term neuronal hypersensitivity." Science 295. 5554 (2002): 508-512.

Mette et al., "Transcriptional silencing and promoter methylation triggered by double-stranded RNA." The EMBO journal (2000): 5194-5201.

Metzler et al., "High expression of precursor microRNA-155/BIC RNA in children with Burkitt lymphoma." Genes, Chromosomes and Cancer 39.2 (2004): 167-169.

Meyerhoff et al., "Cortical gamma-aminobutyric acid and glutamate in posttraumatic stress disorder and their relationships to self-reported sleep quality." Sleep 37.5 (2014): 893-900.

Michael et al., "Reduced accumulation of specific microRNAs in colorectal neoplasia." Molecular cancer research 1.12 (2003): 882-891.

Milligan et al., "Turnover of primary transcripts is a major step in the regulation of mouse H19 gene expression." EMBO reports (2002): 774-779.

Miska et al., "Microarray analysis of microRNA expression in the developing mammalian brain." Genome biology 5.9 (2004): 1-13.

Mithoefer et al., "Durability of improvement in post-traumatic stress disorder symptoms and absence of harmful effects or drug dependency after 3, 4-methylenedioxymethamphetamine-assisted psychotherapy: a prospective long-term follow-up study." Journal of psychopharmacology 27.1 (2013): 28-39.

Mithoefer et al., "The safety and efficacy of+3, 4-methylenedioxymethamphetamine-assisted psychotherapy in subjects with chronic, treatment-resistant posttraumatic stress disorder: the first randomized controlled pilot study." Journal of psychopharmacology 25.4 (2011): 439-452.

Mlotshwa et al., "RNA silencing and the mobile silencing signal." The Plant Cell 14.suppl_1 (2002): S289-S301.

Mochizuki et al., "Analysis of a piwi-related gene implicates small RNAs in genome rearrangement in Tetrahymena." Cell 110.6 (2002): 689-699.

Modarres et al., "Strong correlation of novel sleep electroencephalography coherence markers with diagnosis and severity of posttraumatic stress disorder." Scientific reports 9.1 (2019): 1-10.

Mollinari et al., "Ablation of PRC1 by small interfering RNA demonstrates that cytokinetic abscission requires a central spindle bundle in mammalian cells, whereas completion of furrowing does not." Molecular biology of the cell 16.3 (2005): 1043-1055.

Moore et al., "Psychometric properties of the penn computerized neurocognitive battery." Neuropsychology 29.2 (2015): 235-246.

Morel et al., "Fertile hypomorphic ARGONAUTE (ago1) mutants impaired in post-transcriptional gene silencing and virus resistance." The Plant Cell 14.3 (2002): 629-639.

Morey et al., "Amygdala volume changes in posttraumatic stress disorder in a large case-controlled veterans group." Archives of general psychiatry 69.11 (2012): 1169-1178.

Morris et al., "Small interfering RNA-induced transcriptional gene silencing in human cells." Science 305.5688 (2004): 1289-1292.

Moss et al., "Conservation of the heterochronic regulator Lin-28, its developmental expression and microRNA complementary sites." Developmental biology 258.2 (2003): 432-442.

Moss et al., "The cold shock domain protein LIN-28 controls developmental timing in C. elegans and is regulated by the lin-4 RNA." Cell 88.5 (1997): 637-646.

Moss, E. "MicroRNAs: hidden in the genome." Current Biology 12.4 (2002): R138-R140.

Moss, E. "Rna interference: it's a small RNA world." Current Biology 11.19 (2001): R772-R775.

Mourelatos et al., "miRNPs: a novel class of ribonucleoproteins containing numerous microRNAs." Genes & development 16.6 (2002): 720-728.

Mourrain et al., "Arabidopsis SGS2 and SGS3 genes are required for posttranscriptional gene silencing and natural virus resistance." Cell 101.5 (2000): 533-542.

Muller et al., "The GAD65 knock out mouse-a model for GABAergic processes in fear-and stress-induced psychopathology." Genes, Brain and Behavior 14.1 (2015): 37-45.

Murchison et al., "miRNAs on the move: miRNA biogenesis and the RNAi machinery." Current opinion in cell biology 16.3 (2004): 223-229.

Nagy et al., "Anti-anxiety action op diazepam after intraamygdaloid application in the rat." Neuropharmacology 18.6 (1979): 573-576.

Nakahara et al., "Expanding roles for miRNAs and siRNAs in cell regulation." Current opinion in cell biology 16.2 (2004): 127-133.

Neilson et al., "Herpesviruses throw a curve ball: new insights into microRNA biogenesis and evolution." Nature Methods 2.4 (2005): 252-254.

Nelson et al., "Microarray-based, high-throughput gene expression profiling of microRNAs." Nature methods 1.2 (2004): 155-161.

Nelson et al., "miRNP: mRNA association in polyribosomes in a human neuronal cell line." Rna 10.3 (2004): 387-394.

Nelson et al., "The microRNA world: small is mighty." Trends in biochemical sciences 28.10 (2003): 534-540.

Neugebauer, R. "Reliability of seizure diaries in adult epileptic patients." Neuroepidemiology 8.5 (1989): 228-233.

Ngo et al., "Double-stranded RNA induces mRNA degradation in Trypanosoma brucei." Proceedings of the National Academy of Sciences 95.25 (1998): 14687-14692.

Nicholson et al., "Molecular characterization of a mouse cDNA encoding Dicer, a ribonuclease III ortholog involved in RNA interference." Mammalian Genome 13.2 (2002): 67-73.

Nijholt et al., "Stress-induced alternative splicing of acetylcholinesterase results in enhanced fear memory and long-term potentiation." Molecular psychiatry 9.2 (2004): 174-183.

Nikitin et al., "Protein synthesis inhibitor administration before a reminder caused recovery from amnesia induced by memory reconsolidation impairment with NMDA glutamate receptor antagonist." Brain Research Bulletin 171 (2021): 44-55.

Nilsson et al., "Enhanced detection and distinction of RNA by enzymatic probe ligation." Nature biotechnology 18.7 (2000): 791-793.

Nilsson et al., "Making ends meet in genetic analysis using padlock probes." Human mutation 19.4 (2002): 410-415.

Nishitsuji et al., "Expression of small hairpin RNA by lentivirus-based vector confers efficient and stable gene-suppression of HIV-1 on human cells including primary non-dividing cells." Microbes and infection 6.1 (2004): 76-85.

Noguchi et al., "Regulation of gene expression by sodium valproate in epithelial-to-mesenchymal transition." Lung 193.5 (2015): 691-700.

(56)         References Cited

OTHER PUBLICATIONS

Boutet et al., "Arabidopsis HEN1: a genetic link between endogenous miRNA controlling development and siRNA controlling transgene silencing and virus resistance." Current Biology 13.10 (2003): 843-848.

Boutla et al., "Developmental defects by antisense-mediated inactivation of micro-RNAs 2 and 13 in Drosophila and the identification of putative target genes." Nucleic acids research 31.17 (2003): 4973-4980.

Boutla et al., "Induction of RNA interference in Caenorhabditis elegans by RNAs derived from plants exhibiting posttranscriptional gene silencing." Nucleic Acids Research 30.7 (2002): 1688-1694.

Bowman J., "Class III HD-Zip gene regulation, the golden fleece of ARGONAUTE activity." Bioessays 26.9 (2004): 938-942.

Bracht et al., "Trans-splicing and polyadenylation of let-7 microRNA primary transcripts." Rna 10.10 (2004): 1586-1594.

Bradley et al., "A multidimensional meta-analysis of psychotherapy for PTSD." American journal of Psychiatry 162.2 (2005): 214-227.

Brady et al., "Comorbidity of psychiatric disorders and posttraumatic stress disorder." Journal of clinical psychiatry 61 (2000): 22-32.

Brady et al., "Efficacy and safety of sertraline treatment of posttraumatic stress disorder: a randomized controlled trial." Jama 283.14 (2000): 1837-1844.

Brady et al., "Valproate treatment of comorbid panic disorder and affective disorders in two alcoholic patients." Journal of clinical psychopharmacology 14.1 (1994): 81-82.

Brandenberger et al., "Transcriptome characterization elucidates signaling networks that control human ES cell growth and differentiation." Nature biotechnology 22.6 (2004): 707-716.

Brantl S., "Antisense-RNA regulation and RNA interference." Biochimica et Biophysica Acta (BBA)-Gene Structure and Expression 1575.1-3 (2002): 15-25.

Brehm et al., "Parameters for establishing humanized mouse models to study human immunity: analysis of human hematopoietic stem cell engraftment in three immunodeficient strains of mice bearing the IL2rynull mutation." Clinical immunology 135.1 (2010): 84-98.

Bremner et al., "Chronic PTSD in Vietnam combat veterans: course of illness and substance abuse." The American journal of psychiatry 153.3 (1996): 369-375.

Bremner et al., "Decreased benzodiazepine receptor binding in prefrontal cortex in combat-related posttraumatic stress disorder." American Journal of Psychiatry 157.7 (2000): 1120-1126.

Bremner et al., "MRI and PET study of deficits in hippocampal structure and function in women with childhood sexual abuse and posttraumatic stress disorder." American journal of psychiatry 160.5 (2003): 924-932.

Bremner et al., "Neural correlates of declarative memory for emotionally valenced words in women with posttraumatic stress disorder related to early childhood sexual abuse." Biological psychiatry 53.10 (2003): 879-889.

Bremner et al., "Positron emission tomographic imaging of neural correlates of a fear acquisition and extinction paradigm in women with childhood sexual-abuse-related post-traumatic stress disorder." Psychological medicine 35.6 (2005): 791-806.

Bremner J., "Alterations in brain structure and function associated with post-traumatic stress disorder." Seminars in clinical neuropsychiatry 4.4 (1999):249-255.

Bremner J., "Neuroimaging in posttraumatic stress disorder and other stress-related disorders." Neuroimaging Clinics of North America 17.4 (2007): 523-538.

Brennecke et al., "bantam encodes a developmentally regulated microRNA that controls cell proliferation and regulates the proapoptotic gene hid in Drosophila." Cell 113.1 (2003): 25-36.

Brennecke et al., "Principles of microRNA-target recognition." PLoS biology 3.3 (2005): 1-15.

Brenner et al., "Gene expression analysis by massively parallel signature sequencing (MPSS) on microbead arrays." Nature biotechnology 18.6 (2000): 630-634.

Brezinsky et al., "A simple method for enriching populations of transfected CHO cells for cells of higher specific productivity." Journal of immunological methods 277.1-2 (2003): 141-155.

Bridge et al., "Induction of an interferon response by RNAi vectors in mammalian cells." Nature genetics 34.3 (2003): 263-264.

Brill et al., "Chronic valproic acid treatment triggers increased neuropeptide y expression and signaling in rat nucleus reticularis thalami." Journal of Neuroscience 26.25 (2006): 6813-6822.

Brooks et al., "Long-term survival after traumatic brain injury part II: Life expectancy." Archives of physical medicine and rehabilitation 96.6 (2015): 1000-1005.

Brown et al., "A computational view of microRNAs and their targets." Drug Discovery Today 10.8 (2005): 595-601.

Brown et al., "Neural systems for cognitive and emotional processing in posttraumatic stress disorder." Frontiers in psychology 3 (2012): 1-14.

Brown et al., "The stepped wedge trial design: a systematic review." BMC medical research methodology 6.1 (2006): 1-9.

Bryant R., "Post-traumatic stress disorder: a state-of-the-art review of evidence and challenges." World psychiatry 18.3 (2019): 259-269.

Bucherelli et al., "Aversive memory reactivation engages in the amygdala only some neurotransmitters involved in consolidation." Learning & Memory 13.4 (2006): 426-430.

Buck et al., "Design strategies and performance of custom DNA sequencing primers." Biotechniques 27.3 (1999): 528-536.

Cai et al., "Human microRNAs are processed from capped, polyadenylated transcripts that can also function as mRNAs." Rna 10.12 (2004): 1957-1966.

Cai et al., "Kaposi's sarcoma-associated herpesvirus expresses an array of viral microRNAs in latently infected cells." Proceedings of the National Academy of Sciences 102.15 (2005): 5570-5575.

Calin et al., "Frequent deletions and down-regulation of micro-RNA genes miR15 and miR 16 at 13q14 in chronic lymphocytic leukemia." Proceedings of the national academy of sciences 99.24 (2002): 15524-15529.

Calin et al., "Human microRNA genes are frequently located at fragile sites and genomic regions involved in cancers." Proceedings of the National Academy of Sciences 101.9 (2004): 2999-3004.

Calin et al., "MicroRNA profiling reveals distinct signatures in B cell chronic lymphocytic leukemias." Proceedings of the National Academy of Sciences 101.32 (2004): 11755-11760.

Cao et al., "Role of the DRM and CMT3 methyltransferases in RNA-directed DNA methylation." Current biology 13.24 (2003): 2212-2217.

Carbothane@ 134 HG - Product Data Sheet, Carboline.com, Retrieved from the Internet: <URL:https://msds.carboline.com/servlet/FeedFile/1/prod/0859/PDS%3A%7BPC%3A0859%3BMID%3A1%3BLID%3A1%7D/Carbothane_134_HG_PDS.pdf> (2023): 1-4.

Carmell et al., "Germline transmission of RNAi in mice." Nature structural biology 10.2 (2003): 91-92.

Carmell et al., "RNase III enzymes and the initiation of gene silencing." Nature structural & molecular biology 11.3 (2004): 214-218.

Carmell et al., "The Argonaute family: tentacles that reach into RNAi, developmental control, stem cell maintenance, and tumorigenesis." Genes & development 16.21 (2002): 2733-2742.

Carmichael G., "Antisense starts making more sense." Nature biotechnology 21.4 (2003): 371-372.

Carrington et al., "Role of microRNAs in plant and animal development." Science 301.5631 (2003): 336-338.

Carter et al., "A computational approach to identify genes for functional RNAs in genomic sequences." Nucleic acids research 29.19 (2001): 3928-3938.

Carthew R., "Making and breaking with nucleases and small RNAs." Nature Structural & Molecular Biology 10.10 (2003): 776-777.

Casaca-Carreira et al., "Transependymal cerebrospinal fluid flow: opportunity for drug delivery." Molecular neurobiology 55.4 (2018): 2780-2788.

Casset et al., "A peptide mimetic of an anti-CD4 monoclonal antibody by rational design." Biochemical and biophysical research communications 307.1 (2003): 198-205.

(56)         References Cited

OTHER PUBLICATIONS

Catalanotto et al., "Involvement of small RNAs and role of the qde genes in the gene silencing pathway in Neurospora." Genes & development 16.7 (2002): 790-795.

Caudy et al., "A micrococcal nuclease homologue in RNAi effector complexes." Nature 425.6956 (2003): 411-414.

U.S. Appl. No. 63/223,629, filed Jul. 20, 2021, 26 pages.

U.S. Appl. No. 63/280,367, filed Nov. 17, 2021, 54 pages.

U.S. Appl. No. 63/294,611, filed Dec. 29, 2021, 38 pages.

U.S. Appl. No. 63/310,288, filed Feb. 15, 2022, 55 pages.

Uchida et al., "A novel role of the mammalian GSPT/eRF3 associating with poly (A)-binding protein in Cap/Poly (A)-dependent translation." Journal of Biological Chemistry 277.52 (2002): 50286-50292.

Ullman et al., "Psychosocial correlates of PTSD symptom severity in sexual assault survivors." Journal of traumatic stress 20.5 (2007): 821-831.

Vaiva et al., "Low posttrauma GABA plasma levels as a predictive factor in the development of acute posttraumatic stress disorder." Biological psychiatry 55.3 (2004): 250-254.

Vaiva et al., "Relationship between posttrauma GABA plasma levels and PTSD at 1-year follow-up." American Journal of Psychiatry 163.8 (2006): 1446-1448.

Vajdos et al., "Comprehensive functional maps of the antigen-binding site of an anti-ErbB2 antibody obtained with shotgun scanning mutagenesis." Journal of molecular biology 320.2 (2002): 415-428.

Valoczi et al., "Sensitive and specific detection of microRNAs by northern blot analysis using LNA-modified oligonucleotide probes." Nucleic acids research 32.22 (2004): e175-e175.

Van Hilten et al., "Intrathecal baclofen for the treatment of dystonia in patients with reflex sympathetic dystrophy." New England Journal of Medicine 343.9 (2000): 625-630.

Vance et al., "RNA silencing in plants—defense and counterdefense." science 292.5525 (2001): 2277-2280.

Varker et al., "Efficacy of psychoactive drugs for the treatment of posttraumatic stress disorder: a systematic review of MDMA, ketamine, LSD and psilocybin." Journal of Psychoactive Drugs 53.1 (2021): 85-95.

Vaucheret et al., "Post-transcriptional gene silencing in plants." Journal of cell science 114.17 (2001): 3083-3091.

Vaucheret et al., "The action of ARGONAUTE1 in the miRNA pathway and its regulation by the miRNA pathway are crucial for plant development." Genes & development 18.10 (2004): 1187-1197.

Vaucheret et al., "Transcriptional gene silencing in plants: targets, inducers and regulators." TRENDS in Genetics 17.1 (2001): 29-35.

Vella et al., "Architecture of a validated microRNA:: target interaction." Chemistry & biology 11.12 (2004): 1619-1623.

Vella et al., "The C. elegans microRNA let-7 binds to imperfect let-7 complementary sites from the lin-41 3' UTR." Genes & development 18.2 (2004): 132-137.

Verbitsky et al., "Rodent models of post-traumatic stress disorder: behavioral assessment." Translational psychiatry 10.1 (2020): 1-28.

Verma et al., "Modified oligonucleotides: synthesis and strategy for users." Annual review of biochemistry 67.1 (1998): 99-134.

Vermeulen et al., "The contributions of dsRNA structure to Dicer specificity and efficiency." Rna 11.5 (2005): 674-682.

Villareal et al., "Efficacy of quetiapine monotherapy in posttraumatic stress disorder: a randomized, placebo-controlled trial." American Journal of Psychiatry 173.12 (2016): 1205-1212.

Villareal et al., "Reduced hippocampal vol. and total white matter vol. in posttraumatic stress disorder." Biological psychiatry 52.2 (2002): 119-125.

Voinnet et al., "A viral movement protein prevents spread of the gene silencing signal in Nicotiana benthamiana." Cell 103.1 (2000): 157-167.

Voinnet, O. "Induction and suppression of RNA silencing: insights from viral infections." Nature Reviews Genetics 6.3 (2005): 206-220.

Voinnet, O. "Rna silencing: small RNAs as ubiquitous regulators of gene expression." Current opinion in plant biology 5.5 (2002): 444-451.

Volpe et al., "Regulation of heterochromatic silencing and histone H3 lysine-9 methylation by RNAi." Science 297.5588 (2002): 1833-1837.

Vuillemenot et al., "Nonclinical evaluation of CNS-administered TPP1 enzyme replacement in canine CLN2 neuronal ceroid lipofuscinosis." Molecular genetics and metabolism 114.2 (2015): 281-293.

Walters et al., "RNAi-induced down-regulation of FLT3 expression in AML cell lines increases sensitivity to MLN518." Blood 105.7 (2005): 2952-2954.

Walters, J. "The relationship between post traumatic stress disorder (PTSD) symptoms and career outcomes of army enlisted servicemembers." The Pardee RAND Graduate School (2014): 1-189.

Wang et al., "An attempt to identify reproducible high-density EEG markers of PTSD during sleep." Sleep 43.1 (2020): 1-12.

Wang et al., "Identification of 20 microRNAs from Oryza sativa." Nucleic Acids Research 32.5 (2004): 1688-1695.

Wang et al., "Inter-channel phase differences during sleep spindles are altered in Veterans with PTSD." NeuroImage: Clinical 28 (2020): 102390.

Wang et al., "Prediction and identification of Arabidopsis thaliana microRNAs and their mRNA targets." Genome biology 5.9 (2004): 1-15.

Wang et al., "Tumor necrosis factor a-dependent drug resistance to purine and pyrimidine analogues in human colon tumor cells mediated through IKK." Journal of Biological Chemistry 280.9 (2005): 7634-7644.

Wang et al., "Viral discovery and sequence recovery using DNA microarrays." PLoS biology 1.2 (2003): 257-260.

Watanabe et al., "Stage-specific expression of microRNAs during Xenopus development." FEBS letters 579.2 (2005): 318-324.

Waterhouse et al., "Virus resistance and gene silencing in plants can be induced by simultaneous expression of sense and antisense RNA." Proceedings of the National Academy of Sciences 95.23 (1998): 13959-13964.

Weathers et al., "The Clinician-Administered PTSD Scale for DSM-5 (CAPS-5): Development and initial psychometric evaluation in military veterans." Psychological assessment 30.3 (2018): 383-395.

Weber et al., "Quorum-sensing-based toolbox for regulatable transgene and siRNA expression in mammalian cells." Biotechnology progress 21.1 (2005): 178-185.

Weber, M. "New human and mouse microRNA genes found by homology search." The FEBS journal 272.1 (2005): 59-73.

Wei et al., "TTK/hMps1 participates in the regulation of DNA damage checkpoint response by phosphorylating CHK2 on threonine 68." Journal of Biological Chemistry 280.9 (2005): 7748-7757.

Wen et al., "Deep convolution neural network and autoencoders-based unsupervised feature learning of EEG signals." IEEE Access 6 (2018): 25399-25410.

Wesemann et al., "Clinical accuracy and safety using the SynchroMed II intrathecal drug infusion pump." Regional Anesthesia & Pain Medicine 39.4 (2014): 341-346.

Wesley et al., "Construct design for efficient, effective and high-throughput gene silencing in plants." The Plant Journal 27.6 (2001): 581-590.

Westhof et al., "From RNAi to epigenomes: how RNA rules the world." Chembiochem 6.2 (2005): 441-443.

White et al., "Antibody-targeted immunotherapy for treatment of malignancy." Annual review of medicine 52.1 (2001): 125-145.

Wideman et al., "Involvement of classical neurotransmitter systems in memory reconsolidation: Focus on destabilization." Neurobiology of learning and memory 156 (2018): 68-79.

Wienholds et al., "The microRNA-producing enzyme Dicer1 is essential for zebrafish development." Nature genetics 35.3 (2003): 217-218.

Wightman et al., "Posttranscriptional regulation of the heterochronic gene lin-14 by lin-4 mediates temporal pattern formation in C. elegans." Cell 75.5 (1993): 855-862.

(56) References Cited

OTHER PUBLICATIONS

Straud et al., "Examining military population and trauma type as moderators of treatment outcome for first-line psychotherapies for PTSD: A meta-analysis." Journal of anxiety disorders 67 (2019): 1-26.
Stremlau et al., "The cytoplasmic body component TRIM5a restricts HIV-1 infection in Old World monkeys." Nature 427.6977 (2004): 848-853.
Sugiyama et al., "RNA-dependent RNA polymerase is an essential component of a self-enforcing loop coupling heterochromatin assembly to siRNA production." Proceedings of the National Academy of Sciences 102.1 (2005): 152-157.
Suh et al., "Human embryonic stem cells express a unique set of microRNAs." Developmental biology 270.2 (2004): 488-498.
Sumimoto et al., "Gene therapy for human small-cell lung carcinoma by inactivation of Skp-2 with virally mediated RNA interference." Gene therapy 12.1 (2005): 95-100.
Sun et al., "Development of a micro-array to detect human and mouse microRNAs and characterization of expression in human organs." Nucleic acids research 32.22 (2004): e188-e188.
Sunkar et al., "Novel and stress-regulated microRNAs and other small RNAs from Arabidopsis." The Plant Cell 16.8 (2004): 2001-2019.
Sussman et al., "Neuroanatomical features in soldiers with post-traumatic stress disorder." BMC neuroscience 17.1 (2016): 1-11.
Suzuma et al., "Identification and characterization of novel small RNAs in the aspS-yrvM intergenic region of the Bacillus subtilis genome." Microbiology 148.8 (2002): 2591-2598.
Svennerholm et al., "Alzheimer disease-effect of continuous intracerebroventricular treatment with GM1 ganglioside and a systematic activation programme." Dementia and geriatric cognitive disorders 14.3 (2002): 128-136.
Swagerman et al., "The Computerized Neurocognitive Battery: Validation, aging effects, and heritability across cognitive domains." Neuropsychology 30.1 (2016): 53-64.
SYGNUS® Implantable Connector System, Balseal.com, Retrieved from the Internet: <URL: https://www.balseal.com/contact/sygnus/> (2024): 1-13.
Szymanski et al., "Noncoding RNA transcripts." Journal of applied genetics 44.1 (2003): 1-20.
Tabara et al., "The dsRNA binding protein RDE-4 interacts with RDE-1, DCR-1, and a DExH-box helicase to direct RNAi in C. elegans." Cell 109.7 (2002): 861-871.
Tabara et al., "The rde-1 gene, RNA interference, and transposon silencing in C. elegans." Cell 99.2 (1999): 123-132.
Takamizawa et al., "Reduced expression of the let-7 microRNAs in human lung cancers in association with shortened postoperative survival." Cancer research 64.11 (2004): 3753-3756.
Tan et al., "RNAi, a new therapeutic strategy against viral infection." Cell research 14.6 (2004): 460-466.
Tang et al., "A biochemical framework for RNA silencing in plants." Genes & development 17.1 (2003): 49-63.
Tang, G. "siRNA and miRNA: an insight into RISCs." Trends in biochemical sciences 30.2 (2005): 106-114.
Tanno et al., "Silencing of endogenous IGFBP-5 by micro RNA interference affects proliferation, apoptosis and differentiation of neuroblastoma cells." Cell Death & Differentiation 12.3 (2005): 213-223.
Tanzer et al., "Evolution of microRNAs located within Hox gene clusters." Journal of Experimental Zoology Part B: Molecular and Developmental Evolution 304.1 (2005): 75-85.
Tanzer et al., "Molecular evolution of a microRNA cluster." Journal of molecular biology 339.2 (2004): 327-335.
Taylor et al., "The potential of RNA interference as a tool in the management of viral hepatitis." Journal of hepatology 42.1 (2005): 139-144.
Teixeira et al., "Multiple numerical chromosome aberrations in cancer: what are their causes and what are their consequences." Seminars in cancer biology. Vol. 15. No. 1. Academic Press (2005): 3-12.

Teixeira et al., "Processing bodies require RNA for assembly and contain nontranslating mRNAs." Rna 11.4 (2005): 371-382.
Thiagarajan, T. "EEG and FMRI Papers by the Numbers," Sapien Labs, Retrieved from the Internet: <URL: https://sapienlabs.org/lab-talk/500000-human-neuroscience-papers/> (2016): 1-7.
Thomas et al., "Size constraints for targeting post-transcriptional gene silencing and for RNA-directed methylation in Nicotiana benthamiana using a potato virus X vector." The Plant Journal 25.4 (2001): 417-425.
Thomson et al., "A custom microarray platform for analysis of microRNA gene expression." Nature methods 1.1 (2004): 47-53.
Thurman et al., "Traumatic brain injury in the United States: a public health perspective." The Journal of head trauma rehabilitation 14.6 (1999): 602-615.
Tijsterman et al., "Dicers at RISC: the mechanism of RNAi." Cell 117.1 (2004): 1-3.
Tomari et al., "A protein sensor for siRNA asymmetry." Science 306.5700 (2004): 1377-1380.
Tomari et al., "MicroRNA biogenesis: drosha can't cut it without a partner." Current Biology 15.2 (2005): R61-R64.
Tomari et al., "Perspective: machines for RNAi." Genes & development 19.5 (2005): 517-529.
Tops et al., "RDE-2 interacts with MUT-7 to mediate RNA interference in Caenorhabditis elegans." Nucleic acids research 33.1 (2005): 347-355.
Trainor, P. "Developmental Biology Is "Cruzing"." Developmental Cell 7.4 (2004): 481-486.
Trivedi et al., "The Inventory of Depressive Symptomatology, Clinician Rating (IDS-C) and Self-Report (IDS-SR), and the Quick Inventory of Depressive Symptomatology, Clinician Rating (QIDS-C) and Self-Report (QIDS-SR) in public sector patients with mood disorders: a psychometric evaluation." Psychological medicine 34.1 (2004): 73-82.
Trousselard et al., "Is plasma GABA level a biomarker of post-traumatic stress disorder (PTSD) severity? A preliminary study." Psychiatry research 241 (2016): 273-279.
Tucker et al., "Efficacy and safety of topiramate monotherapy in civilian posttraumatic stress disorder: a randomized, double-blind, placebo-controlled study." Journal of Clinical Psychiatry 68.2 (2007): 201-206.
Turner et al., "Review of recent methodological developments in group-randomized trials: part 1—design." American journal of public health 107.6 (2017): 907-915.
Turner et al., "Review of recent methodological developments in group-randomized trials: part 2—analysis." American journal of public health 107.7 (2017): 1078-1086.
Tuschl et al., "Targeted mRNA degradation by double-stranded RNA in vitro." Genes & development 13.24 (1999): 3191-3197.
Tuschl, T. "RNA sets the standard." Nature 421.6920 (2003): 220-221.
U.S. Appl. No. 17/380,415, filed Jul. 20, 2021, 71 pages.
U.S. Appl. No. 17/380,694, filed Jul. 20, 2021, 37 pages.
U.S. Appl. No. 17/868,321, filed Jul. 19, 2022, 24 pages.
U.S. Appl. No. 63/052,284, filed Jul. 15, 2020, 67 pages.
U.S. Appl. No. 63/053,864, filed Jul. 20, 2020, 39 pages.
U.S. Appl. No. 63/054,522, filed Jul. 21, 2020, 24 pages.
U.S. Appl. No. 63/166,705, filed Mar. 26, 2021, 21 pages.
U.S. Appl. No. 63/172,313, filed Apr. 8, 2021, 28 pages.
Shi et al., "Selection and characterization of RNA interference-deficient trypanosomes impaired in target mRNA degradation." Eukaryotic Cell 3.6 (2004): 1445-1453.
Shi, Y. "Mammalian RNAi for the masses." TRENDS in Genetics 19.1 (2003): 9-12.
Shim et al., "Machine-learning-based classification between post-traumatic stress disorder and major depressive disorder using P300 features." NeuroImage: Clinical 24 (2019): 1-8.
Shin et al., "Amygdala, medial prefrontal cortex, and hippocampal function in PTSD." Annals of the New York Academy of Sciences 1071.1 (2006): 67-79.
Shin et al., "Hippocampal function in posttraumatic stress disorder." Hippocampus 14.3 (2004): 292-300.

(56)     References Cited

OTHER PUBLICATIONS

Shin et al., "Regional cerebral blood flow in the amygdala and medial prefrontalcortex during traumatic imagery in male and female vietnam veterans with ptsd." Archives of general psychiatry 61.2 (2004): 168-176.

Shin et al., "Resting metabolic activity in the cingulate cortex and vulnerability to posttraumatic stress disorder." Archives of general psychiatry 66.10 (2009): 1099-1107.

Shin et al., "The neurocircuitry of fear, stress, and anxiety disorders." Neuropsychopharmacology 35.1 (2010): 169-191.

Shin et al., "Transcriptional and post-transcriptional regulation of the PKCd gene by etoposide in L1210 murine leukemia cells: implication of PKCd autoregulation." Journal of molecular biology 340.4 (2004): 681-693.

Shiner et al., "A retrospective comparative effectiveness study of medications for posttraumatic stress disorder in routine practice." The Journal of clinical psychiatry 79.5 (2018): 1-20.

Shiner et al., "Anticonvulsant medication use in veterans with posttraumatic stress disorder." The Journal of clinical psychiatry 78.5 (2017): e545-e552.

Shivakumar et al., "Targeting B-lymphocyte stimulator/B-cell activating factor and a proliferation-inducing ligand in hematologic malignancies." Clinical Lymphoma and Myeloma 7.2 (2006): 106-108.

Sigova et al., "A single Argonaute protein mediates both transcriptional and posttranscriptional silencing in Schizosaccharomyces pombe." Genes & development 18.19 (2004): 2359-2367.

Sijen et al., "Post-transcriptional gene-silencing: RNAs on the attack or on the defense." Bioessays 22.6 (2000): 520-531.

Silhavy et al., "A viral protein suppresses RNA silencing and binds silencing-generated, 21-to 25-nucleotide double-stranded RNAs." The EMBO journal (2002): 1-11.

Silvestri et al., "Rotavirus replication: plus-sense templates for double-stranded RNA synthesis are made in viroplasms." Journal of virology 78.14 (2004): 7763-7774.

Simmonds et al., "Detection of genome-scale ordered RNA structure (GORS) in genomes of positive-stranded RNA viruses: Implications for virus evolution and host persistence." Rna 10.9 (2004): 1337-1351.

Sims et al., "Identification and characterization of circulating human transitional B cells." Blood 105.11 (2005): 4390-4398.

Siolas et al., "Synthetic shRNAs as potent RNAi triggers." Nature biotechnology 23.2 (2005): 227-231.

Slack et al., "The lin-41 RBCC gene acts in the C. elegans heterochronic pathway between the let-7 regulatory RNA and the LIN-29 transcription factor." Molecular cell 5.4 (2000): 659-669.

Sledz et al., "Activation of the interferon system by short-interfering RNAs." Nature cell biology 5.9 (2003): 834-839.

Smale S., "The establishment and maintenance of lymphocyte identity through gene silencing." Nature immunology 4.7 (2003): 607-615.

Smalheiser et al., "A population-based statistical approach identifies parameters characteristic of human microRNA-mRNA interactions." BMC bioinformatics 5.1 (2004): 1-8.

Smalheiser, N. "Est analyses predict the existence of a population of chimeric microRNA precursor-mRNA transcripts expressed in normal human and mouse tissues." Genome biology 4.7 (2003): 1-3.

Smallridge R., "A small fortune." Nature Reviews Molecular Cell Biology 2.12 (2001): 867-867.

Smirnova et al., "Regulation of miRNA expression during neural cell specification." European Journal of Neuroscience 21.6 (2005): 1469-1477.

Smith et al., "Intrathecal drug delivery." Pain physician 11.2S (2008): S89-S104.

Smith et al., "The early detection of prostate carcinoma with prostate specific antigen: the Washington University experience." Cancer: Interdisciplinary International Journal of The American Cancer Society 80.9 (1997): 1852-1856.

Smith et al., "Total silencing by intron-spliced hairpin RNAs." Nature 407.6802 (2000): 319-320.

Soldan et al., "La Crosse virus nonstructural protein NSs counteracts the effects of short interfering RNA." Journal of virology 79.1 (2005): 234-244.

Song et al., "Crystal structure of Argonaute and its implications for RISC slicer activity." science 305.5689 (2004): 1434-1437.

Sontheimer et al., "Argonaute journeys into the heart of RISC." Science 305.5689 (2004): 1409-1410.

Sosin et al., "Trends in death associated with traumatic brain injury, 1979 through 1992: success and failure." Jama 273.22 (1995): 1778-1780.

Souret et al., "AtXRN4 degrades mRNA in Arabidopsis and its substrates include selected miRNA targets." Molecular cell 15.2 (2004): 173-183.

Soutschek et al., "Therapeutic silencing of an endogenous gene by systemic administration of modified siRNAs." Nature 432.7014 (2004): 173-178.

Spira et al., "Generation of mutant monoclonal antibodies." Methods of Hybridoma Formation. Totowa, NJ: Humana Press (1987): 379-397.

Spiridon et al., "A comparison of the in vitro and in vivo activities of IgG and F (ab') 2 fragments of a mixture of three monoclonal anti-Her-2 antibodies." Clinical Cancer Research 10.10 (2004): 3542-3551.

Spitzer et al., "Trauma, posttraumatic stress disorder, and physical illness: findings from the general population." Psychosomatic medicine 71.9 (2009): 1012-1017.

Stark et al., "Identification of Drosophila microRNA targets." PLoS biology 1.3 (2003): 397-409.

Staubli et al., "Facilitation of glutamate receptors enhances memory." Proceedings of the National Academy of Sciences 91.2 (1994): 777-781.

Steenkamp et al., "Psychotherapy for military-related Ptsd: A review of randomized clinical trials." Jama 314.5 (2015): 489-500.

Stein et al., "Genetic programming by the proteolytic fragments of the amyloid precursor protein: somewhere between confusion and clarity." Reviews in the neurosciences 14.4 (2003): 317-342.

Stein et al., "Ketamine for PTSD: well, isn't that special." American Journal of Psychiatry 178.2 (2021): 116-118.

Stein et al., "Randomized, placebo-controlled trial of the angiotensin receptor antagonist losartan for posttraumatic stress disorder." Biological Psychiatry 90.7 (2021): 473-481.

Steinman et al., "Transcriptional analysis of targets in multiple sclerosis." Nature Reviews Immunology 3.6 (2003): 483-492.

Stevens et al., "Episodic memory after trauma exposure: Medial temporal lobe function is positively related to re-experiencing and inversely related to negative affect symptoms." NeuroImage: Clinical 17 (2018): 650-658.

Stevenson M., "Dissecting HIV-1 through RNA interference." Nature Reviews Immunology 3.11 (2003): 851-858.

Stix G., "Hitting the genetic off switch." Scientific American 291.4 (2004): 98-101.

Storz et al., "Controlling mRNA stability and translation with small, noncoding RNAs." Current opinion in microbiology 7.2 (2004): 140-144.

Stoutjesdijk et al., "hpRNA-mediated targeting of the Arabidopsis FAD2 gene gives highly efficient and stable silencing." Plant physiology 129.4 (2002): 1723-1731.

Caudy et al., "Fragile X-related protein and VIG associate with the RNA interference machinery." Genes & development 16.19 (2002): 2491-2496.

Cawley et al., "Unbiased mapping of transcription factor binding sites along human chromosomes 21 and 22 points to widespread regulation of noncoding RNAs." Cell 116.4 (2004): 499-509.

Cerutti H., "RNA interference: traveling in the cell and gaining functions." TRENDS in Genetics 19.1 (2003): 39-46.

Chang et al., "MicroRNAs act sequentially and asymmetrically to control chemosensory laterality in the nematode." Nature 430.7001 (2004): 785-789.

Chang et al., "miR-122, a mammalian liver-specific microRNA, is processed from hor mRNA and maydownregulate the high affinity cationic amino acid transporter CAT-1." RNA biology 1.2 (2004): 106-113.

(56) References Cited

OTHER PUBLICATIONS

Chang et al., "Resistance of human hepatitis delta virus RNAs to dicer activity." Journal of virology 77.22 (2003): 11910-11917.
Chang P., "Encapsulation for somatic gene therapy." Annals of the New York Academy of Sciences 875.1 (1999): 146-158.
Chapman et al., "Viral RNA silencing suppressors inhibit the microRNA pathway at an intermediate step." Genes & development 18.10 (2004): 1179-1186.
Chapoval et al., "Anti-CD3 x anti-tumor F (ab') 2 bifunctional antibody activates and retargets tumor-infiltrating lymphocytes." Journal of immunology 155.3 (1995): 1296-1303.
Chattopadhyay et al., "Lack of impact of the loss of constitutive folate receptor a expression, achieved by RNA interference, on the activity of the new generation antifolate pemetrexed in Hela cells." Clinical cancer research 10.23 (2004): 7986-7993.
Chen et al., "A bioinformatics based approach to discover small RNA genes in the Escherichia coli genome." Biosystems 65.2-3 (2002): 157-177.
Chen et al., "A simple framework for contrastive learning of visual representations." International conference on machine learning (2020): 1-11.
Chen et al., "Automatic sleep stage classification based on subthalamic local field potentials." IEEE Transactions on Neural Systems and Rehabilitation Engineering 27.2 (2019): 118-128.
Chen et al., "Improved baselines with momentum contrastive learning." arXiv preprint arXiv:2003.04297 (2020): 1-3.
Chen et al., "MicC, a second small-RNA regulator of Omp protein expression in Escherichia coli." Journal of bacteriology 186.20 (2004): 6689-6697.
Chen et al., "MicroRNAs as regulators of mammalian hematopoiesis." Seminars in immunology 17 (2005): 155-165.
Chen et al., "MicroRNAs modulate hematopoietic lineage differentiation." science 303.5654 (2004): 83-86.
Chen et al., "Selection and analysis of an optimized anti-VEGF antibody: crystal structure of an affinity-matured Fab in complex with antigen." Journal of molecular biology 293.4 (1999): 865-881.
Chen et al., "Viral virulence protein suppresses RNA silencing-mediated defense but upregulates the role of microRNA in host gene expression." The Plant Cell 16.5 (2004): 1302-1313.
Chen T., "Advancing Self-Supervised and Semi-Supervised Learning with SimCLR," Blog.research.google, Retrieved from the Internet: <URL: https://research.google/blog/advancing-self-supervised-and-semi-supervised-learning-with-simclr/> (2020): 1-8.
Chen X., "A microRNA as a translational repressor of APETALA2 in Arabidopsis flower development." Science 303.5666 (2004): 2022-2025.
Cheng et al., "Antisense inhibition of human miRNAs and indications for an involvement of miRNA in cell growth and apoptosis." Nucleic acids research 33.4 (2005): 1290-1297.
Cheng et al., "Stem cells: from epigenetics to microRNAs." Neuron 46.3 (2005): 363-367.
Chesnut et al., "The role of secondary brain injury in determining outcome from severe head injury." Journal of Trauma and Acute Care Surgery 34.2 (1993): 216-222.
Chiu et al., "Hodgkin lymphoma cells express TACI and BCMA receptors and generate survival and proliferation signals in response to BAFF and APRIL." Blood 109.2 (2007): 729-739.
Cios K., "Deep Neural Networks—A Brief History." in: Gaweda et al., Advances in Data Analysis with Computational Intelligence Methods, vol. 378 (2018): 183-200.
Clark et al., "How does B cell depletion therapy work, and how can it be improved." Annals of the rheumatic diseases 64.suppl 4 (2005): iv77-iv80.
Clarke et al., "Computer-assisted EEG diagnostic review for idiopathic generalized epilepsy." Epilepsy & Behavior 121 (2021): 1-18.
Cobb et al., "Tracing microRNA patterns in mice." Nature genetics 36.10 (2004): 1033-1034.

Coburn et al., "Potent and specific inhibition of human immunodeficiency virus type 1 replication by RNA interference." Journal of virology 76.18 (2002): 9225-9231.
Coenen et al., "What work-related exposures are associated with post-traumatic stress disorder? A systematic review with meta-analysis." BMJ open 11.8 (2021): 1-12.
Cogoni et al., "Post-transcriptional gene silencing across kingdoms." Current opinion in genetics & development 10.6 (2000): 638-643.
Cohen et al., "Neuronal overexpression of 'readthrough' acetylcholinesterase is associated with antisense- suppressible behavioral impairments." Molecular psychiatry 7.8 (2002): 874-885.
Cohen J., "Statistical Power Analysis for the Behavioral Sciences." (Cover page, title page, and table of contents), 2nd Edition (1988): 1-8.
Colciaghi et al., "Platelet APP, Adam 10 and BACE alterations in the early stages of Alzheimer disease." Neurology 62.3 (2004): 498-501.
Cole et al., "Direct labeling of RNA with multiple biotins allows sensitive expression profiling of acute leukemia class predictor genes." Nucleic acids research 32.11 (2004): 1-9.
Collins et al., "Long subcutaneous tunnelling reduces infection rates in paediatric external ventricular drains." Child's Nervous System 30.10 (2014): 1671-1678.
Colsky et al., "FcR-Independent Antibody-Mediated Cellular Cytotoxicity." Journal of leukocyte biology 49.6 (1991): 548-555.
Conner et al., "Posttraumatic stress disorder and suicide in 5.9 million individuals receiving care in the veterans health administration health system." Journal of affective Disorders 166 (2014): 1-5.
Connolly et al., "Characterization of the relationship between intracranial pressure and electroencephalographic monitoring in burst-suppressed patients." Neurocritical care 22.2 (2015): 212-220.
Connor et al., "Fluoxetine in post-traumatic stress disorder: randomised, double-blind study." The British Journal of Psychiatry 175.1 (1999): 17-22.
Conrad C., "Chronic stress-induced hippocampal vulnerability: the glucocorticoid vulnerability hypothesis." Reviews in the Neurosciences 19.6 (2008): 395-412.
Conrad C., "What is the functional significance of chronic stress-induced CA3 dendritic retraction within the hippocampus." Behavioral and cognitive neuroscience reviews 5.1 (2006): 41-60.
Conway et al., "Chronic vagus nerve stimulation significantly improves quality of life in treatment-resistant major depression." The Journal of Clinical Psychiatry 79.5 (2018): 52-59.
Cook et al., "Anti-seizure therapy with a long-term, implanted intra-cerebroventricular delivery system for drug-resistant epilepsy: A first-in-man study." EClinicalMedicine 22 (2020): 1-9.
Cook et al., "Prediction of seizure likelihood with a long-term, implanted seizure advisory system in patients with drug-resistant epilepsy: a first-in-man study." The Lancet Neurology 12.6 (2013): 563-571.
Coquery et al., "Regulatory roles of the tumor necrosis factor receptor BCMA." Critical Review in Immunology 32.4 (2012): 287-305.
Coquery et al., "T follicular helper cells contribute to autoimmunity through the BCMA-BAFF axis (BA2P. 117)." The Journal of Immunology 192.Supplement_1 (2014): 45-4.
Courtney et al., "Links between traumatic brain injury and ballistic pressure waves originating in the thoracic cavity and extremities." Brain Injury 21.7 (2007): 657-662.
Courtois et al., "Clinical Practice Guideline for the Treatment of Posttraumatic Stress Disorder (PTSD) in Adults." adopted as APA Policy on Feb. 24, 2017, American Psychological Association, 139 pages.
Abbott A. L., "Heterochronic genes." Current Biology 13.21 (2003): R824-R825.
Abrahante et al., "The Caenorhabditis elegans hunchback-like gene lin-57/hbl-1 controls developmental time and is regulated by microRNAs." Developmental cell 4.5 (2003): 625-637.
Abrams D., "Feasibility of Delivery of Anti-Epilepsy Medications into the Cerebrospinal Fluid (10802)." Neuromodulation 19.3 (2015): e107.

(56)          References Cited

OTHER PUBLICATIONS

Achard et al., "Modulation of floral development by a gibberellin-regulated microRNA." Development 131.14 (2004): 3357-3365.

Adai et al., "Computational prediction of miRNAs in Arabidopsis thaliana." Genome research 15.1 (2005): 78-91.

Adamou et al., "Valproate in the treatment of PTSD: systematic review and meta analysis." Current medical research and opinion 23.6 (2007): 1285-1291.

Agrawal et al., "Role of Toll-like receptors in antisense and siRNA [corrected]." Nature biotechnology 22.12 (2004): 1533-1537.

Akaneya et al., "RNAi-induced gene silencing by local electroporation in targeting brain region." Journal of neurophysiology 93.1 (2005): 594-602.

Albott et al., "Efficacy, safety, and durability of repeated ketamine infusions for comorbid posttraumatic stress disorder and treatment-resistant depression." The Journal of clinical psychiatry 79.3 (2018): 17462.

Albright et al., "Intraventricular baclofen for dystonia: techniques and outcomes." Journal of Neurosurgery: Pediatrics 3.1 (2009): 11-14.

Albright L., "Technique for insertion of intraventricular baclofen catheters." Journal of Neurosurgery: Pediatrics 8.4 (2011): 394-395.

Alibu et al., "A doubly inducible system for RNA interference and rapid RNAi plasmid construction in Trypanosoma brucei." Molecular and biochemical parasitology 139.1 (2005): 75-82.

Allawi et al., "Quantitation of microRNAs using a modified Invader assay." Rna 10.7 (2004): 1153-1161.

Allen et al., "Evolution of microRNA genes by inverted duplication of target gene sequences in Arabidopsis thaliana." Nature genetics 36.12 (2004): 1282-1290.

Allinson et al., "ADAMs family members as amyloid precursor protein a-secretases." Journal of neuroscience research 74.3 (2003): 342-352.

Allshire R., "RNAi and heterochromatin—a hushed-up affair." Science 297.5588 (2002): 1818-1819.

Alonso et al., "Days out of role due to common physical and mental conditions: results from the WHO World Mental Health surveys." Molecular psychiatry 16.12 (2011): 1234-1246.

Alsford et al., "Multiplex analysis of RNA interference defects in Trypanosoma brucei." Molecular and biochemical parasitology 139.1 (2005): 1-8.

Altuvia et al., "Clustering and conservation patterns of human microRNAs." Nucleic acids research 33.8 (2005): 2697-2706.

Altuvia S., "Regulatory small RNAs: the key to coordinating global regulatory circuits." Journal of Bacteriology 186.20 (2004): 6679-6680.

Alzoubi et al., "Pentoxifylline prevents post-traumatic stress disorder induced memory impairment." Brain research bulletin 139 (2018): 263-268.

Alzoubi et al., "Prevention of memory impairment induced by post-traumatic stress disorder by cerebrolysin." Psychiatry Research 270 (2018): 430-437.

Ambinder et al., "Epstein-Barr virus genome B95-8." XP002500226. Retrieved from EBI Database accession No. ADN12161 (2004).

Ambros V., "A uniform system for microRNA annotation." Rna 9.3 (2003): 277-279.

Ambros V., "MicroRNA pathways in flies and worms: growth, death, fat, stress, and timing." Cell 113.6 (2003): 673-676.

Ambros V., "MicroRNAs and other tiny endogenous RNAs in C. elegans." Current Biology 13.10 (2003): 807-818.

Ambros V., "microRNAs: tiny regulators with great potential." Cell 107.7 (2001): 823-826.

Ambros V., "The functions of animal microRNAs." Nature 431. 7006 (2004): 350-355.

Anandalakshmi et al., "A calmodulin-related protein that suppresses posttranscriptional gene silencing in plants." Science 290.5489 (2000): 142-144.

Anonymous. "Whither RNAi" Nat Cell Biol 5 (2003): 489-490.

Antonarakis et al., "Chromosome 21 and down syndrome: from genomics to pathophysiology." Nature reviews genetics 5.10 (2004): 725-738.

Aoun et al., "Impact of traumatic brain injury on sleep: an overview." Nature and science of sleep (2019): 131-140.

Arai et al., "Establishment of stable hFis1 knockdown cells with an siRNA expression vector." Journal of biochemistry 136.4 (2004): 421-425.

Aravin et al., "Dissection of a natural RNA silencing process in the Drosophila melanogaster germ line." Molecular and cellular biology 24.15 (2004): 6742-6750.

Aravin et al., "The small RNA profile during Drosophila melanogaster development." Developmental cell 5.2 (2003): 337-350.

Arditte Hall et al., "Plasma gamma-aminobutyric acid (GABA) levels and posttraumatic stress disorder symptoms in trauma-exposed women: a preliminary report." Psychopharmacology 238.6 (2021): 1541-1552.

Argaman et al., "Novel small RNA-encoding genes in the intergenic regions of *Escherichia coli*." Current Biology 11.12 (2001): 941-950.

Arias et al., "RNA silencing of rotavirus gene expression." Virus research 102.1 (2004): 43-51.

Ashrafi et al., "Genome-wide RNAi analysis of Caenorhabditis elegans fat regulatory genes." Nature 421.6920 (2003): 268-272.

Atkinson A., "Intracerebroventricular drug administration." Translational and Clinical Pharmacology 25.3 (2017): 117-124.

Atwoli et al., "Epidemiology of posttraumatic stress disorder: prevalence, correlates and consequences." Current opinion in psychiatry 28.4 (2015): 307-311.

Augustinsson et al., "Intracerebroventricular administration of GM1 ganglioside to presenile Alzheimer patients." Dementia and geriatric cognitive disorders 8.1 (1997): 26-33.

Aukerman et al., "Regulation of flowering time and floral organ identity by a microRNA and its APETALA2-like target genes." The Plant Cell 15.11 (2003): 2730-2741.

Averill et al., "Glutamate dysregulation and glutamatergic therapeutics for PTSD: Evidence from human studies." Neuroscience letters 649 (2017): 147-155.

Avery et al., "BAFF selectively enhances the survival of plasmablasts generated from human memory B cells." The Journal of clinical investigation 112.2 (2003): 286-297.

Ayash-Rashkovsky et al., "Generation of Th1 immune responses to inactivated, gp120-depleted HIV-1 in mice with a dominant Th2 biased immune profile via imunostimulatory oligonucleotides—relevance to AIDS vaccines in developing countries." Vaccine 20.21-22 (2002): 2684-2692.

Baba et al., "Solution structure of an RNA stem-loop derived from the 3' conserved region of eel LINE UnaL2." Rna 10.9 (2004): 1380-1387.

Babak et al., "Probing microRNAs with microarrays: tissue specificity and functional inference." Rna 10.11 (2004): 1813-1819.

Bagasra et al., "RNA interference: the molecular immune system." Journal of molecular histology 35.6 (2004): 545-553.

Bahramian et al., "GENE impedance: a natural process for control of gene expression and the origin of RNA interference." Journal of theoretical biology 233.3 (2005): 301-314.

Pooggin et al., "Fighting geminiviruses by RNAi and vice versa." Plant molecular biology 55.2 (2004): 149-152.

Popoli et al., "The stressed synapse: the impact of stress and glucocorticoids on glutamate transmission." Nature Reviews Neuroscience 13.1 (2012): 22-37.

Posner et al., "The Columbia-Suicide Severity Rating Scale: initial validity and internal consistency findings from three multisite studies with adolescents and adults." American journal of psychiatry 168.12 (2011): 1266-1277.

Post et al., "Sensitization and kindling: implications for the evolving neural substrates of post-traumatic stress disorder." Neurobiological and Clinical Consequences of Stress: From Normal Adaptation to PTSD (1995): 1-22.

Post-Traumatic Stress Disorder (PTSD), National Institute of Mental Health, Retrieved from the Internet: <URL: https://www.nimh.nih.gov/health/statistics/post-traumatic-stress-disorder-ptsd> (2017): 1-4.

(56)         References Cited

OTHER PUBLICATIONS

Poy et al., "A pancreatic islet-specific microRNA regulates insulin secretion." Nature 432.7014 (2004): 226-230.

Primeau et al., "Valproic acid and panic disorder." The Canadian Journal of Psychiatry 35.3 (1990): 248-250.

Provost et al., "Ribonuclease activity and RNA binding of recombinant human Dicer." The EMBO journal (2002): 1-11.

Puerta-Fernandez et al., "Anchoring hairpin ribozymes to long target RNAs by loop-loop RNA interactions." Antisense and Nucleic Acid Drug Development 12.1 (2002): 1-9.

Puetz et al., "Effects of pharmacotherapy on combat-related PTSD, anxiety, and depression: a systematic review and meta-regression analysis." PloS one 10.5 (2015): 1-18.

Qassem et al., "Psychiatric co-morbidities in post-traumatic stress disorder: detailed findings from the adult psychiatric morbidity survey in the English population." Psychiatric Quarterly 92.1 (2021): 321-330.

Qi et al., "Inhibition of cell growth and shoot development by a specific nucleotide sequence in a noncoding viroid RNA." The Plant Cell 15.6 (2003): 1360-1374.

Rajewsky et al., "Computational identification of microRNA targets." Genome Biology 5.2 (2004): 1-34.

Rao, M. "Conserved and divergent paths that regulate self-renewal in mouse and human embryonic stem cells." Developmental biology 275.2 (2004): 269-286.

Rapaport et al., "Posttraumatic stress disorder and quality of life: results across 64 weeks of sertraline treatment." Journal of Clinical Psychiatry 63.1 (2002): 59-65.

Rapaport et al., "Quality-of-life impairment in depressive and anxiety disorders." American Journal of Psychiatry 162.6 (2005): 1171-1178.

Rapozzi et al., "Efficient silencing of bcr/abl oncogene by single- and double-stranded siRNAs targeted against b2a2 transcripts." Biochemistry 43.51 (2004): 16134-16141.

Raskind et al., "Trial of prazosin for post-traumatic stress disorder in military veterans." New England Journal of Medicine 378.6 (2018): 507-517.

Rauch et al., "Neurocircuitry models of posttraumatic stress disorder and extinction: human neuroimaging research—past, present, and future." Biological psychiatry 60.4 (2006): 376-382.

Ravindran et al., "Pharmacotherapy of PTSD: premises, principles, and priorities." Brain research 1293 (2009): 24-39.

Reff et al., "Depletion of B cells in vivo by a chimeric mouse human monoclonal antibody to CD20." (1994): 435-445.

Rehmsmeier et al., "Fast and effective prediction of microRNA/target duplexes." Rna 10.10 (2004): 1507-1517.

Reiner et al., "Identifying differentially expressed genes using false discovery rate controlling procedures." Bioinformatics 19.3 (2003): 368-375.

Reinhart et al., "MicroRNAs in plants." Genes & development 16.13 (2002): 1616-1626.

Reinhart et al., "Small RNAs correspond to centromere heterochromatic repeats." science 297.5588 (2002): 1831-1831.

Reinhart et al., "The 21-nucleotide let-7 RNA regulates developmental timing in Caenorhabditis elegans." nature 403.6772 (2000): 901-906.

Rhoades et al., "Prediction of plant microRNA targets." cell 110.4 (2002): 513-520.

Rhoda et al., "Studies with staggered starts: multiple baseline designs and group-randomized trials." American Journal of Public Health 101.11 (2011): 2164-2169.

Richards et al., "Sleep disturbance in PTSD and other anxiety-related disorders: an updated review of clinical features, physiological characteristics, and psychological and neurobiological mechanisms." Neuropsychopharmacology 45.1 (2020): 55-73.

Richter-Levin et al., "Animal models of PTSD: a challenge to be met." Molecular psychiatry 24.8 (2019): 1135-1156.

Riedel et al., "Glutamate receptor function in learning and memory." Behavioural brain research 140.1-2 (2003): 1-47.

Rinker et al., "Outcomes of short-gap sensory nerve injuries reconstructed with processed nerve allografts from a multicenter registry study." Journal of reconstructive microsurgery 31.05 (2015): 384-390.

Rivas et al., "Purified Argonaute2 and an siRNA form recombinant human RISC." Nature structural & molecular biology 12.4 (2005): 340-349.

Robb et al., "Specific and potent RNAi in the nucleus of human cells." Nature structural & molecular biology 12.2 (2005): 133-137.

Robins et al., "Incorporating structure to predict microRNA targets." Proceedings of the National Academy of Sciences 102.11 (2005): 4006-4009.

Robinson et al., "Genomic and proteomic analysis of multiple sclerosis: Opinion." Current opinion in immunology 15.6 (2003): 660-667.

Rodriguez et al., "Identification of mammalian microRNA host genes and transcription units." Genome research 14.10a (2004): 1902-1910.

Rose et al., "Blocking memory reconsolidation reverses memory-associated changes in glutamate receptor expression." Journal of Neuroscience 26.45 (2006): 11582-11587.

Roseboom et al., "Evidence in primates supporting the use of chemogenetics for the treatment of human refractory neuropsychiatric disorders." Molecular Therapy 29.12 (2021): 3484-3497.

Rosenbaum et al., "Ventriculostomy: Frequency, length of stay and in-hospital mortality in the United States of America, 1988-2010." Journal of Clinical Neuroscience 21.4 (2014): 623-632.

Rosok et al., "Systematic identification of sense-antisense transcripts in mammalian cells." Nature biotechnology 22.1 (2004): 104-108.

Rosso et al., "Insula and anterior cingulate GABA levels in post-traumatic stress disorder: preliminary findings using magnetic resonance spectroscopy." Depression and anxiety 31.2 (2013): 1-9.

Roth et al., "Expression profiling using a hexamer-based universal microarray." Nature biotechnology 22.4 (2004): 418-426.

Roy et al., "Deep learning-based electroencephalography analysis: a systematic review." Journal of neural engineering 16.5 (2019): 1-38.

Rudikoff et al., "Single amino acid substitution altering antigen-binding specificity." Proceedings of the National Academy of Sciences 79.6 (1982): 1979-1983.

Rush et al., "Clinical research challenges posed by difficult-to-treat depression." Psychological Medicine 52.3 (2022): 419-432.

Ruvkun et al., "The 20 years it took to recognize the importance of tiny RNAs." Cell 116 (2004): S93-S98.

Ruvkun, G., "Glimpses of a tiny RNA world." Science 294.5543 (2001): 797-799.

Ryan et al., "Antibody targeting of B-cell maturation antigen on malignant plasma cells." Molecular cancer therapeutics 6.11 (2007): 3009-3018.

Rye et al., "Interfering with cancer: a brief outline of advances in RNA interference in oncology." Tumor Biology 25.5-6 (2004): 329-336.

Ehret M., "Treatment of posttraumatic stress disorder: Focus on pharmacotherapy." Mental Health Clinician 9.6 (2019): 373-382.

Eichenbaum et al., "The hippocampus-what does it do." Behavioral and neural biology 57.1 (1992): 2-36.

Eichenbaum H., "The hippocampus and declarative memory: cognitive mechanisms and neural codes." Behavioural brain research 127.1-2 (2001): 199-207.

Einav et al., "shRNA-mediated RNA interference as a tool for genetic synthetic lethality screening in mouse embryo fibroblasts." FEBS letters 579.1 (2005): 199-202.

Eis et al., "Accumulation of miR-155 and Bic Rna in human B cell lymphomas." Proceedings of the National Academy of Sciences 102.10 (2005): 3627-3632.

Elbashir et al., "Analysis of gene function in somatic mammalian cells using small interfering RNAs." Methods 26.2 (2002): 199-213.

Elbashir et al., "Duplexes of 21-nucleotide RNAs mediate RNA interference in cultured mammalian cells." nature 411.6836 (2001): 494-498.

(56)                        References Cited

OTHER PUBLICATIONS

Elbashir et al., "Functional anatomy of siRNAs for mediating efficient RNAi in Drosophila melanogaster embryo lysate." The EMBO journal 20.23 (2001): 6877-6888.

Elbashir et al., "RNA interference is mediated by 21-and 22-nucleo-tide RNAs." Genes & development 15.2 (2001): 188-200.

Elmen et al., "Locked nucleic acid (LNA) mediated improvements in siRNA stability and functionality." Nucleic acids research 33.1 (2005): 439-447.

Emrick et al., "Different simultaneous sleep states in the hip-pocampus and neocortex." Sleep 39.12 (2016): 2201-2209.

Engdahl et al., "A two unit antisense RNA cassette test system for silencing of target genes." Nucleic acids research 25.16 (1997): 3218-3227.

Engstrom et al., "Promoter bashing, microRNAs, and Knox genes. New insights, regulators, and targets-of-regulation in the establish-ment of lateral organ polarity in Arabidopsis." Plant Physiology 135.2 (2004): 685-694.

Enright et al., "MicroRNA targets in Drosophila." Genome Biology 5.1 (2003): 1-27.

Epilepsy for Parents and Caregivers, Epilepsy.com, Retrieved from the Internet: <URL: https://www.epilepsy.com/living-epilepsy/epilepsy-and/professional-health-care-providers/about-epilepsy-seizures/idiopathic-4> (2024): 1-9.

Eriksdotter-Jonhagen et al., "Encapsulated cell biodelivery of nerve growth factor to the basal forebrain in patients with Alzheimer's disease." Dementia and geriatric cognitive disorders 33.1 (2012): 18-28.

Esau et al., "MicroRNA-143 regulates adipocyte differentiation." Journal of Biological Chemistry 279.50 (2004): 52361-52365.

Eshed et al., "MicroRNAs guide asymmetric DNA modifications guiding asymmetric organs." Developmental Cell 7.5 (2004): 629-630.

Esquela-Kerscher et al., "The age of high-throughput microRNA profiling." Nature Methods 1.2 (2004): 106-107.

Etkin et al., "Functional neuroimaging of anxiety: a meta-analysis of emotional processing in PTSD, social anxiety disorder, and specific phobia." American journal of Psychiatry 164.10 (2007): 1476-1488.

European Search Report for EP05774516.8, mailed Nov. 27, 2008, 5 pages.

European Search Report for EP16153513.3, mailed Jan. 17, 2020, 7 pages.

Fagard et al., "AGO1, QDE-2, and RDE-1 are related proteins required for post-transcriptional gene silencing in plants, quelling in fungi, and RNA interference in animals." Proceedings of the National Academy of Sciences 97.21 (2000): 11650-11654.

Famulok M., "Chemical biology: green fluorescent RNA." Nature 430 (2004): 976-977.

Fan et al., "RNA interference against a glioma-derived allele of EGFR induces blockade at G2M." Oncogene 24.5 (2005): 829-837.

Feder et al., "A randomized controlled trial of repeated ketamine administration for chronic posttraumatic stress disorder," American Journal of Psychiatry 178.2 (2021): 193-202.

Feder et al., "Efficacy of intravenous ketamine for treatment of chronic posttraumatic stress disorder: a randomized clinical trial." JAMA psychiatry 71.6 (2014): 681-688.

Fenoy et al., "Risks of common complications in deep brain stimulation surgery: management and avoidance." Journal of neu-rosurgery 120.1 (2014): 132-139.

Ferry et al., "The economic burden of PTSD in Northern Ireland." Journal of traumatic stress 28.3 (2015): 191-197.

Fesler F., "Valproate in combat-related posttraumatic stress disor-der." The Journal of Clinical Psychiatry 52.9 (1991): 361-364.

Findley et al., "Maelstrom, a Drosophila spindle-class gene, encodes a protein that colocalizes with Vasa and RDE1/ AGO1 homolog, Aubergine, in nuage." Development 130.5 (2003): 859-871.

Finnegan et al., "The small RNA world." Journal of cell science 116.23 (2003): 4689-4693.

Fire A., "RNA-triggered gene silencing." Trends in Genetics 15.9 (1999): 358-363.

Fire et al., "Potent and specific genetic interference by double-stranded RNA in Caenorhabditis elegans." nature 391.6669 (1998): 806-811.

Fisher et al., "Seizure diaries for clinical research and practice: limitations and future prospects." Epilepsy & Behavior 24.3 (2012): 304-310.

Fleischhack et al., "Pharmacokinetics following intraventricular administration of chemotherapy in patients with neoplastic menin-gitis." Clinical pharmacokinetics 44.1 (2005): 1-31.

Floriano-Sanchez et al., "Differential gene expression profile induced by valproic acid (VPA) in pediatric epileptic patients." Genes 9.7 (2018): 1-15.

Floyd et al., "Ancient microRNA target sequences in plants." Nature 428.6982 (2004): 485-486.

Foa et al., "Prolonged Exposure Therapy for PTSD: Emotional Processing of Traumatic Experiences," Therapist Guide, 2nd ed., Copyright page (2019) 1-2.

Forbes et al., "A guide to guidelines for the treatment of PTSD and related conditions." Journal of traumatic stress 23.5 (2010): 537-552.

Foreman et al., "Quantitative EEG for the detection of brain ischemia." Critical care 16.2 (2012): 1-9.

Forman-Hoffman et al., "Psychological and Pharmacological Treat-ments for Adults With Posttraumatic Stress Disorder: A Systematic Review Update," Agency for Healthcare Research and Quality (2018): 1-4.

Fortier et al., "Temperature-dependent gene silencing by an expressed inverted repeat in Drosophila." genesis 26.4 (2000): 240-244.

Fowler et al., "Intrathecal drug delivery in the era of nanomedicine." Advanced drug delivery reviews 165 (2020): 77-95.

Friedman et al., "Considering future pharmacotherapy for PTSD." Neuroscience letters 649 (2017): 181-185.

Friedrich et al., "RNA molecules as anti-cancer agents." Seminars in cancer biology 14.4 (2004): 223-230.

Froeyen et al., "RNA as a target for drug design, the example of Tat-TAR interaction." Current topics in medicinal chemistry 2.10 (2002): 1123-1145.

Gallinaro et al., "Structural Study of the 5' End of a Synthetic Premessenger RNA from Adenovirus: Evidence for a Long-range Exon-Intron Interaction." Journal of molecular biology 240.3 (1994): 205-225.

Galyam et al., "Complex host cell responses to antisense suppres-sion of ACHE gene expression." Antisense and Nucleic Acid Drug Development 11.1 (2001): 51-57.

Garfinkel et al., "Impaired contextual modulation of memories in PTSD: an fMRI and psychophysiological study of extinction reten-tion and fear renewal." Journal of Neuroscience 34.40 (2014): 13435-13443.

Baldino et al., "Sodium valproate enhancement of gamma-aminobutyric acid (GABA) inhibition: electrophysiological evi-dence for anticonvulsant activity." The Journal of Pharmacology and Experimental Therapeutics 217.2 (1981): 445-450.

Ball et al., "Signal quality of simultaneously recorded invasive and non-invasive EEG." Neuroimage 46.3 (2009): 708-716.

Ballantyne et al., "Comparative efficacy of epidural, subarachnoid, and intracerebroventricular opioids in patients with pain due to cancer (Cochrane Review)." Journal of the American College of Surgeons 200.6 (2005): 1-4.

Bandelow et al., "Biological markers for anxiety disorders, OCD and PTSD: A consensus statement. Part II: Neurochemistry, neurophysiology and neurocognition." The World Journal of Bio-logical Psychiatry 18.3 (2017): 162-214.

Baner et al., "Parallel gene analysis with allele-specific padlock probes and tag microarrays." Nucleic Acids Research 31.17 (2003): e103-e103.

Banerjee et al., "Control of developmental timing by small temporal RNAs: a paradigm for RNA-mediated regulation of gene expres-sion." Bioessays 24.2 (2002): 119-129.

(56)          References Cited

OTHER PUBLICATIONS

Baniasadi et al., "Effect of pregabalin augmentation in treatment of patients with combat-related chronic posttraumatic stress disorder: a randomized controlled trial." Journal of Psychiatric Practice® 20.6 (2014): 419-427.

Bantounas et al., "RNA interference and the use of small interfering RNA to study gene function in mammalian systems." Journal of molecular endocrinology 33.3 (2004): 545-557.

Bao et al., "MicroRNA binding sites in Arabidopsis class III HD-ZIP mRNAs are required for methylation of the template chromosome." Developmental cell 7.5 (2004): 653-662.

Barad et al., "MicroRNA expression detected by oligonucleotide microarrays: system establishment and expression profiling in human tissues." Genome research 14.12 (2004): 2486-2494.

Barcia et al., "Anticonvulsant and neurotoxic effects of intracerebroventricular injection of phenytoin, phenobarbital and carbamazepine in an amygdala-kindling model of epilepsy in the rat." Epilepsy research 33.2-3 (1999): 159-167.

Barcia et al., "Intraventricular and intracerebral delivery of anti-epileptic drugs in the kindling model." Neurotherapeutics 6.2 (2009): 337-343.

Barrick et al., "New RNA motifs suggest an expanded scope for riboswitches in bacterial genetic control." Proceedings of the National Academy of Sciences 101.17 (2004): 6421-6426.

Bartel D., "MicroRNAs: genomics, biogenesis, mechanism, and function." cell 116.2 (2004): 281-297.

Bartel et al., "Micromanagers of gene expression: the potentially widespread influence of metazoan microRNAs." Nature reviews genetics 5.5 (2004): 396-400.

Bartel et al., "MicroRNAs: at the root of plant development." Plant physiology 132.2 (2003): 709-717.

Bashirullah et al., "Coordinate regulation of small temporal RNAs at the onset of Drosophila metamorphosis." Developmental biology 259.1 (2003): 1-8.

Baskerville et al., "Microarray profiling of microRNAs reveals frequent coexpression with neighboring miRNAs and host genes." Rna 11.3 (2005): 241-247.

Basyuk et al., "Human let-7 stem-loop precursors harbor features of RNase III cleavage products." Nucleic acids research 31.22 (2003): 6593-6597.

Baulcombe D., "An RNA microcosm." Science 297.5589 (2002): 2002-2003.

Baulcombe D., "RNA silencing in plants." Nature 431.7006 (2004): 356-363.

Beclin et al., "A branched pathway for transgene-induced RNA silencing in plants." Current Biology 12.8 (2002): 684-688.

Bedell et al., "Sorghum genome sequencing by methylation filtration." PLoS Biology 3.1 (2005): 1-13.

Bejerano et al., "Ultraconserved elements in the human genome." Science 304.5675 (2004): 1321-1325.

Bellucci et al., "Graft-versus-tumor response in patients with multiple myeloma is associated with antibody response to BCMA, a plasma-cell membrane receptor." Blood 105.10 (2005): 3945-3950.

Belostotsky D., "mRNA turnover meets RNA interference." Molecular cell 16.4 (2004): 498-500.

Bennasser et al., "HIV-1 encoded candidate micro-RNAs and their cellular targets." Retrovirology 1.1 (2004): 1-5.

Berezikov et al., "Phylogenetic shadowing and computational identification of human microRNA genes." Cell 120.1 (2005): 21-24.

Bergmann et al., "HIDden targets of microRNAs for growth control." Trends in biochemical sciences 28.9 (2003): 461-463.

Bernstein et al., "Role for a bidentate ribonuclease in the initiation step of RNA interference." Nature 409.6818 (2001): 363-366.

Best et al., "In vitro synthesized small interfering RNAs elicit RNA interference in african trypanosomes: an in vitro and in vivo analysis." Journal of Biological Chemistry 280.21 (2005): 20573-20579.

Bettencourt et al., "Hemolin gene silencing by ds-RNA injected into Cecropia pupae is lethal to next generation embryos." Insect Molecular Biology 11.3 (2002): 267-271.

Better et al., "*Escherichia coli* secretion of an active chimeric antibody fragment." Science 240.4855 (1988): 1041-1043.

Bignold L., "The cell-type-specificity of inherited predispositions to tumours: review and hypothesis." Cancer letters 216.2 (2004): 127-146.

Bisson et al., "Prevention and treatment of PTSD: the current evidence base." European Journal of Psychotraumatology 12.1 (2021): 1-5.

Bisson et al., "Psychological therapies for chronic post-traumatic stress disorder (PTSD) in adults." Cochrane database of systematic reviews 12 (2013): 1-167.

Bitko et al., "Inhibition of respiratory viruses by nasally administered siRNA." Nature medicine 11.1 (2005): 50-55.

Blaszczyk et al., "Crystallographic and modeling studies of RNase III suggest a mechanism for double-stranded RNA cleavage." Structure 9.12 (2001): 1225-1236.

Biran et al., "Interaction of temporal lobe epilepsy and post-traumatic stress disorder: network analysis of a single case." Frontiers in Psychology 11 (2020): 1-7.

Bluett et al., "Does change in distress matter? Mechanisms of change in prolonged exposure for PTSD." Journal of behavior therapy and experimental psychiatry 45.1 (2014): 97-104.

Boden et al., "Enhanced gene silencing of HIV-1 specific siRNA using microRNA designed hairpins." Nucleic acids research 32.3 (2004): 1154-1158.

Boffelli et al., "Phylogenetic shadowing of primate sequences to find functional regions of the human genome." Science 299.5611 (2003): 1391-1394.

Bohnsack et al., "Exportin 5 is a RanGTP-dependent dsRNA-binding protein that mediates nuclear export of pre-miRNAs." Rna 10.2 (2004): 185-191.

Bonnet et al., "Detection of 91 potential conserved plant microRNAs in Arabidopsis thaliana and Oryza sativa identifies important target genes." Proceedings of the National Academy of Sciences 101.31 (2004): 11511-11516.

Bonnet et al., "Evidence that microRNA precursors, unlike other non-coding RNAs, have lower folding free energies than random sequences." Bioinformatics 20.17 (2004): 2911-2917.

Borghans et al., "Animal models for posttraumatic stress disorder: an overview of what is used in research." World journal of psychiatry 5.4 (2015): 387-396.

Borodina et al., "Ligation-based synthesis of oligonucleotides with block structure." Analytical biochemistry 318.2 (2003): 309-313.

Boscarino J., "Posttraumatic stress disorder and physical illness: results from clinical and epidemiologic studies." Annals of the New York Academy of sciences 1032.1 (2004): 141-153.

Bothe et al., "How expensive are post-traumatic stress disorders? Estimating incremental health care and economic costs on anonymised claims data." The European Journal of Health Economics 21.6 (2020): 917-930.

Bottros et al., "Current perspectives on intrathecal drug delivery." Journal of pain research (2014): 615-626.

Couzin J., "Human RNA Slows Down a Primate Retrovirus." Science 308.5721 (2005): 480-481.

Couzin J., "RNAi shows cracks in its armor." Science 306.5699 (2004): 1124-1125.

Craik et al., "Deep learning for electroencephalogram (EEG) classification tasks: a review." Journal of neural engineering 16.3 (2019): 1-29.

Crawford et al., "Serum prostate-specific antigen and digital rectal examination for early detection of prostate cancer in a national community-based program." Urology 47.6 (1996): 863-869.

Crestani et al., "Decreased GABAA-receptor clustering results in enhanced anxiety and a bias for threat cues." Nature neuroscience 2.9 (1999): 833-839.

Crestani et al., "Trace fear conditioning involves hippocampal a5 GABAA receptors." Proceedings of the National Academy of Sciences 99.13 (2002): 8980-8985.

Crete et al., "Graft transmission of induced and spontaneous post-transcriptional silencing of chitinase genes." The Plant Journal 28.5 (2001): 493-501.

Cullen B., "RNA interference: antiviral defense and genetic tool." Nature immunology 3.7 (2002): 597-599.

(56) References Cited

OTHER PUBLICATIONS

Cullen B., "Transcription and processing of human microRNA precursors." Molecular cell 16.6 (2004): 861-865.
Czeh et al., "Chronic stress reduces the number of GABAergic interneurons in the adult rat hippocampus, dorsal- ventral and region-specific differences." Hippocampus 25.3 (2015): 393-405.
Dandekar et al., "HIV-1 Tat directly binds to NFKB enhancer sequence: role in viral and cellular gene expression." Nucleic acids research 32.4 (2004): 1270-1278.
Darce et al., "Regulated expression of BAFF-binding receptors during human B cell differentiation." The Journal of Immunology 179.11 (2007): 7276-7286.
Database GenBank: XP523298.2, "tumor necrosis factor receptor superfamily member 17 [Pan troglodytes]." NCBI. com, Retrieved from the Internet: <URL:https://www.ncbi.nlm.nih.gov/protein/XP_523298.2/> (2006): 1-2.
Davidson et al., "Highly efficient small interfering RNA delivery to primary mammalian neurons induces MicroRNA-like effects before mRNA degradation." Journal of Neuroscience 24.45 (2004): 10040-10046.
Davidson et al., "Molecular medicine for the brain: silencing of disease genes with RNA interference." The Lancet Neurology 3.3 (2004): 145-149.
Davidson et al., "The efficacy and tolerability of tiagabine in adult patients with post-traumatic stress disorder." Journal of clinical psychopharmacology 27.1 (2007): 85-88.
Davidson et al., "Treatment of posttraumatic stress disorder with venlafaxine extended release: a 6-month randomized controlled trial." Archives of general psychiatry 63.10 (2006): 1158-1165.
Davies et al., "Affinity improvement of single antibody VH domains: residues in all three hypervariable regions affect antigen binding." Immunotechnology 2.3 (1996): 169-179.
Davis et al., "Comprehensive review of the psychiatric uses of valproate." Journal of clinical psychopharmacology 20.1 (2000): 1S-17S.
Davis et al., "Divalproex in the treatment of posttraumatic stress disorder: a randomized, double-blind, placebo-controlled trial in a veteran population." Journal of clinical psychopharmacology 28.1 (2008): 84-88.
Davis et al., "Phasic vs sustained fear in rats and humans: role of the extended amygdala in fear vs anxiety." Neuropsychopharmacology 35.1 (2010): 105-135.
De Barros et al., "Gender differences in prevalence of psychiatric disorders, levels of alexithymia, and coping strategies in patients with refractory mesial temporal epilepsy and comorbid psychogenic nonepileptic seizures." Epilepsy & Behavior 82 (2018): 1-5.
De Pascalis et al., "Grafting of "abbreviated" complementarity-determining regions containing specificity-determining residues essential for ligand contact to engineer a less immunogenic humanized monoclonal antibody." The Journal of Immunology 169.6 (2002): 3076-3084.
Deer et al., "Polyanalgesic consensus conference 2007: recommendations for the management of pain by intrathecal (intraspinal) drug delivery: report of an interdisciplinary expert panel." Neuromodulation: Technology at the neural interface 10.4 (2007): 300-328.
Definition of Between, Dictionary.com, Retrieved from the Internet <URL: https://www.dictionary.com/browse/between> (2021): 1-3.
Demidov et al., "Two sides of the coin: affinity and specificity of nucleic acid interactions." Trends in biochemical sciences 29.2 (2004): 62-71.
Denli et al., "Processing of primary microRNAs by the Microprocessor complex." Nature 432.7014 (2004): 231-235.
Dennis C., "Gene regulation: The brave new world of RNA." Nature 418.6894 (2002): 122-125.
Dennis C., "Small RNAs: the genome's guiding hand." Nature 420 (2002): 732.
Di Serio et al., "Sense-and antisense-mediated gene silencing in tobacco is inhibited by the same viral suppressors and is associated with accumulation of small RNAs." Proceedings of the National Academy of Sciences 98.11 (2001): 6506-6510.

Diagnostic And Statistical Manual Of Mental Disorders, 5th ed., DSM-5, American Psychiatric Association (2013) 1-13.
Diergaarde et al., "Pharmacological manipulation of memory reconsolidation: Towards a novel treatment of pathogenic memories." European journal of pharmacology 585.2-3 (2008): 453-457.
Digraham et al., "Ischaemic brain damage is still common in fatal non-missile head injury." Journal of neurology, neurosurgery & Psychiatry 52.3 (1989): 346-350.
Doench et al., "siRNAs can function as miRNAs." Genes & development 17.4 (2003): 438-442.
Doench et al., "Specificity of microRNA target selection in translational repression." Genes & development 18.5 (2004): 504-511.
Domingo-Fernandez et al., "PTSD Biomarker Database: Deep dive metadatabase for PTSD biomarkers, visualizations and analysis tools." Database (2019): 1-8.
Dorsett et al., "siRNAs: applications in functional genomics and potential as therapeutics." Nature reviews Drug discovery 3.4 (2004): 318-329.
Dostie et al., "Numerous microRNPs in neuronal cells containing novel microRNAs." Rna 9.2 (2003): 180-186.
Draghici S., "Statistical intelligence: effective analysis of high-density microarray data." Drug discovery today 7.11 (2002): S55-S63.
Dresios et al., "Cold stress-induced protein Rbm3 binds 60S ribosomal subunits, alters microRNA levels, and enhances global protein synthesis." Proceedings of the National Academy of Sciences 102.6 (2005): 1865-1870.
Dsouza et al., "Searching for patterns in genomic data." Trends in Genetics 13.12 (1997): 497-498.
Duensing et al., "Cyclin-dependent kinase inhibitor indirubin-3'-oxime selectively inhibits human papillomavirus type 16 E7-induced numerical centrosome anomalies." Oncogene 23.50 (2004): 8206-8215.
Dugas et al., "MicroRNA regulation of gene expression in plants." Current opinion in plant biology 7.5 (2004): 512-520.
Dunlop et al., "Assessing treatment-resistant posttraumatic stress disorder: The Emory treatment resistance interview for PTSD (E-Trip)." Behavioral Sciences 4.4 (2014): 511-527.
Dunoyer et al., "Probing the MicroRNA and small interfering RNA pathways with virus-encoded suppressors of RNA silencing." The Plant Cell 16.5 (2004): 1235-1250.
Duxbury et al., "Systemic siRNA-mediated gene silencing: a new approach to targeted therapy of cancer." Annals of surgery 240.4 (2004): 667-676.
Dykxhoorn et al., "Killing the messenger: short RNAs that silence gene expression." Nature reviews Molecular cell biology 4.6 (2003): 457-467.
Eddy S., "Computational genomics of noncoding RNA genes." Cell 109.2 (2002): 137-140.
Eddy S., "Non-coding RNA genes and the modern RNA world." Nature Reviews Genetics 2.12 (2001): 919-929.
Edwards et al., "Epstein-Barr virus BART microRNAs are produced from a large intron prior to splicing." Journal of virology 82.18 (2008): 9094-9106.
Wilson et al., "RNA interference blocks gene expression and RNA synthesis from hepatitis C replicons propagated in human liver cells." Proceedings of the National Academy of Sciences 100.5 (2003): 2783-2788.
Winkler et al., "Control of gene expression by a natural metabolite-responsive ribozyme." Nature 428.6980 (2004): 281-286.
Wiznerowicz et al., "Conditional suppression of cellular genes: lentivirus vector-mediated drug-inducible RNA interference." Journal of virology 77.16 (2003): 8957-8961.
Wong et al., "Computationally efficient epileptic seizure prediction based on extremely randomised trees." Proceedings of the Australasian Computer Science Week Multiconference (2020): 1-3.
Wood N., "Unravelling the molecular basis of viral suppression of PTGS." Trends in Plant Science 7.9 (2002): 384-385.
Woodman et al., "Panic disorder: treatment with valproate." The Journal of clinical psychiatry 55.4 (1994): 134-136.
Written Opinion in PCT/US2021/041763, mailed May 30, 2022, 9 pages.

(56) References Cited

OTHER PUBLICATIONS

Written Opinion in PCT/US2021/041766, mailed May 30, 2022, 7 pages.

Written Opinion in PCT/US2021/041772, mailed May 30, 2022, 8 pages.

Written Opinion in PCT/US2021/042315, mailed Jun. 8, 2022, 8 pages.

Written Opinion in PCT/US2022/054049, mailed Nov. 16, 2023, 9 pages.

Wrocklage et al., "Neuropsychological functioning in veterans with posttraumatic stress disorder: Associations with performance validity, comorbidities, and functional outcomes." Journal of the International Neuropsychological Society 22.4 (2016): 399-411.

Wu et al., "An electroencephalographic signature predicts antidepressant response in major depression." Nature biotechnology 38.4 (2020): 439-447.

Wu et al., "Humanization of a murine monoclonal antibody by simultaneous optimization of framework and CDR residues." Journal of Molecular Biology 294.1 (1999): 151-162.

Wu et al., "Inhibition of SARS-CoV replication by siRNA." Antiviral research 65.1 (2005): 45-48.

Wu et al., "Unsupervised feature learning via non-parametric instance discrimination." Proceedings of the IEEE conference on computer vision and pattern recognition (2018): 3733-3742.

Wuchty et al., "Complete suboptimal folding of RNA and the stability of secondary structures." Biopolymers: Original Research on Biomolecules 49.2 (1999): 145-165.

Xayaphoummine et al., "Prediction and statistics of pseudoknots in RNA structures using exactly clustered stochastic simulations." Proceedings of the National Academy of Sciences 100.26 (2003): 15310-15315.

Xiang et al., "Amine-modified random primers to label probes for DNA microarrays." nature biotechnology 20.7 (2002): 738-742.

Xiao et al., "A novel mechanism of checkpoint abrogation conferred by Chk1 downregulation." Oncogene 24.8 (2005): 1403-1411.

Xie et al., "Genetic and functional diversification of small RNA pathways in plants." PLoS biology 2.5 (2004): 642-652.

Xie et al., "Negative feedback regulation of Dicer-Like1 in Arabidopsis by microRNA-guided mRNA degradation." Current Biology 13.9 (2003): 784-789.

Xie et al., "Systematic discovery of regulatory motifs in human promoters and 3' UTRs by comparison of several mammals." Nature 434.7031 (2005): 338-345.

Xu et al., "B-cell maturation protein, which binds the tumor necrosis factor family members BAFF and APRIL, is dispensable for humoral immune responses." Molecular and Cellular Biology 21.12 (2001): 4067-4074.

Xu et al., "MicroRNAs and the regulation of cell death." TRENDS in Genetics 20.12 (2004): 617-624.

Xu et al., "The Drosophila microRNA Mir-14 suppresses cell death and is required for normal fat metabolism." Current Biology 13.9 (2003): 790-795.

Yang et al., "Dicer is required for embryonic angiogenesis during mouse development." Journal of Biological Chemistry 280.10 (2005): 9330-9335.

Yang et al., "Evidence that processed small dsRNAs may mediate sequence-specific mRNA degradation during RNAi in Drosophila embryos." Current Biology 10.19 (2000): 1191-1200.

Yang et al., "Intracranial hemorrhage risk factors of deep brain stimulation for Parkinson's disease: a 2-year follow-up study." Journal of International Medical Research 48.5 (2020): 1-10.

Ye et al., "Recognition of small interfering RNA by a viral suppressor of RNA silencing." Nature 426.6968 (2003): 874-878.

Yee et al., "GABAA receptors containing the a5 subunit mediate the trace effect in aversive and appetitive conditioning and extinction of conditioned fear." European Journal of Neuroscience 20.7 (2004): 1928-1936.

Yeh et al., "A double-blind randomized controlled trial to study the efficacy of topiramate in a civilian sample of PTSD." Cns neuroscience & therapeutics 17.5 (2011): 305-310.

Yehuda et al., "Learning and memory in Holocaust survivors with posttraumatic stress disorder." Biological psychiatry 55.3 (2004): 291-295.

Yekta et al., "MicroRNA-directed cleavage of HOXB8 mRNA." Science 304.5670 (2004): 594-596.

Yelin et al., "Widespread occurrence of antisense transcription in the human genome." Nature biotechnology 21.4 (2003): 379-386.

Yi et al., "Exportin-5 mediates the nuclear export of pre-microRNAs and short hairpin RNAs." Genes & development 17.24 (2003): 3011-3016.

Yi et al., "Overexpression of exportin 5 enhances RNA interference mediated by short hairpin RNAs and microRNAs." Rna 11.2 (2005): 220-226.

Ying et al., "Intron-derived microRNAs-fine tuning of gene functions." Gene 342.1 (2004): 25-28.

Ying et al., "Intronic microRNAs." Biochemical and biophysical research communications 326.3 (2005): 515-520.

Yoo et al., "A systemic small RNA signaling system in plants." The Plant Cell 16.8 (2004): 1979-2000.

YouTube video entitled: "Biomarker Terminology: Speaking the Same Language," uploaded Jan. 27, 2017 by user "U.S. Food and Drug Administration," [retrieved on Jun. 24, 2020]. Retrieved from the Internet: <URL: https://www.youtube.com/watch?v=OXo5E0R7zBc>, 1 page.

Yu et al., "Methylation as a crucial step in plant microRNA biogenesis." Science 307.5711 (2005): 932-935.

Yuan et al., "Adaptive design for staggered-start clinical trial." The International Journal of Biostatistics 12.2 (2016): 1-17.

Yun et al., "Both ERK and Wnt/ß-catenin pathways are involved in Wnt3a-induced proliferation." Journal of cell science 118.2 (2005): 313-322.

Zamore, P. "Ancient pathways programmed by small RNAs." Science 296.5571 (2002): 1265-1269.

Zamore, P. "Plant RNAi: How aViral silencing suppressor inactivates siRNA." Current Biology 14.5 (2004): R198- R200.

Zamvil et al., "Diverse targets for intervention during inflammatory and neurodegenerative phases of multiple sclerosis." Neuron 38.5 (2003): 685-688.

Zanatta et al., "Valproic acid interactions with the NavMs voltage-gated sodium channel." Proceedings of the National Academy of Sciences 116.52 (2019): 26549-26554.

Zandvakili et al., "Use of machine learning in predicting clinical response to transcranial magnetic stimulation in comorbid post-traumatic stress disorder and major depression: a resting state electroencephalography study." Journal of affective disorders 252 (2019): 47-54.

Zeng et al., "Both natural and designed micro RNAs can inhibit the expression of cognate mRNAs when expressed in human cells." Molecular cell 9.6 (2002): 1327-1333.

* cited by examiner

FIG. 20

IMPLANTABLE MEDICAL DEVICE FOR USE WITH OR HAVING RECORDING ELECTRODE

CROSS REFERENCE TO RELATED APPLICATION

This application claims the benefit of priority to U.S. Provisional Patent Application No. 63/310,288, filed on 15 Feb. 2022, the disclosure of which is incorporated herein by reference in its entirety.

FIELD

The present disclosure relates to, among other things, devices, assemblies, and systems for use with, or including, devices having a recording electrode for detecting brain activity data; particularly for use with an implantable catheter, as well as methods associated therewith.

INTRODUCTION

Catheters and associated devices have been employed to deliver therapeutic agents to compartments of the brain comprising cerebral spinal fluid (CSF) or for withdrawing CSF from the brain. The catheters may be used to drain CSF from the brain, such as with a ventriculoperitoneal shunt or external ventricular drain; to percutaneously deliver therapeutic fluid to, or withdraw CSF from, the CSF space, such as with Ommaya or Rickman's reservoir; or to infuse therapeutic agent to the CSF space, such as with an implantable infusion device. Surgical procedures to implant the catheters and associated devices are invasive. For example, surgical placement of the catheter alone requires a burr hole to be drilled through the skull and the catheter or an introducer to be advanced through brain tissue to reach the CSF-containing compartment.

In some cases, such catheters and associated devices may be used to monitor a patient's health or therapy progression. For example, if the device includes an access port for withdrawing CSF through catheter, the withdrawn CSF may be evaluated, for example, to determine whether the patient has a bacterial, fungal, or viral infection or to determine whether a delivered therapeutic agent is present in the CSF at effective concentrations. However, monitoring of electrical brain signals, which may be important for monitoring the therapy, a condition being treated, or a brain state, is not possible with such devices.

Brain activity may be monitored in such patients by using a separate system to record brain activity from the scalp. Such electroencephalogram (EEG) recordings may be useful for periodic monitoring of the patient's brain activity but are not suitable for long-term, continuous monitoring for patients that are not confined to a health care facility. In addition, the signal provided by such EEG recordings tends to be noisy and of lower quality due to signal attenuation through the skull and scalp.

SUMMARY

The present disclosure relates to, among other things, devices and systems configured for use with a catheter for delivering therapeutic agents to the brain or withdrawing, shunting, or draining CSF from the brain. The devices and systems may include a sheath configured to receive the catheter. The sheath may include an electrode configured to be intracranially positioned for recording brain activity data.

The devices and systems may include a burr hole apparatus configured to receive the catheter and the sheath or portions thereof.

The devices and systems described herein may facilitate intracranial implantation of an electrode for recording brain activity data with a catheter for delivering fluid to or withdrawing, shunting, or draining fluid from a brain of a subject.

In an aspect, the present disclosure describes a burr hole device. The burr hole device is configured to receive a catheter for delivering fluid to or withdrawing, shunting, or draining fluid from a brain of a subject and to receive a cable of a sheath, where a conductor of the cable is electrically coupled to an electrode of the sheath.

In embodiments, the burr hole device includes a body having a top surface and a bottom surface and defining a lumen extending from the top surface to the bottom surface. The lumen is configured to receive a catheter configured to infuse fluid to, or withdraw fluid from, a brain of a subject. At least a portion of the bottom surface is configured to be disposed on a surface of a skull adjacent to a burr hole in the skull of the subject. The body further defines a top groove along the top surface. The top groove extends from the lumen towards a lateral edge of the top surface of the body. The top groove is configured to receive the catheter. The body further defines a bottom groove along the bottom surface. The bottom groove extends from a lateral edge of the bottom surface end towards the lumen. The bottom groove is configured to receive a cable. The cable may be a cable of a sheath device configured to receive the lead, wherein the sheath device has an electrode to which a conductor of the cable is electrically coupled.

In embodiments, the burr hole device includes a body having a top surface and a bottom surface and defining a lumen extending from the top surface to the bottom surface. The lumen is configured to receive a catheter configured to infuse fluid to, or withdraw fluid from, a brain of a subject. At least a portion of the bottom surface is configured to be disposed on a surface of a skull adjacent to a burr hole in the skull of the subject. The body further defines a first top groove along the top surface. The first top groove extends from the lumen towards a lateral edge of the top surface of the body. The first top groove is configured to receive the catheter. The body further defines a second top groove along the top surface. The second top groove extends from the lumen towards a lateral edge of the top surface of the body. The second top groove is configured to receive a cable. The cable may be a cable of a sheath device configured to receive the lead, wherein the sheath device has an electrode to which a conductor of the cable is electrically coupled.

In embodiments, the burr hole device includes a body having a top surface and a bottom surface and defining a lumen extending from the top surface to the bottom surface. The lumen is configured to receive a catheter configured to infuse fluid to, or withdraw fluid from, a brain of a subject. At least a portion of the bottom surface is configured to be disposed on a surface of a skull adjacent to a burr hole in the skull of the subject. The body further defines a top groove along the top surface. The top groove extends from the lumen towards a lateral edge of the top surface of the body. The top groove comprises a lower groove portion and an upper groove portion, the lower groove portion having a smaller diametric dimension than the upper groove portion. The lower groove portion is configured to receive a cable. The upper groove portion is configured to receive the catheter such that the catheter is positioned over the cable when the both the cable and the catheter are received in the top groove. The cable may be a cable of a sheath device configured to receive the lead, wherein the sheath device has an electrode to which a conductor of the cable is electrically coupled.

In embodiments, the burr hole device defines an upper flange portion and a lower portion. The lower portion is configured to be placed within the burr hole, and the upper flange portion is configured to be disposed on the surface of the skull. The lower portion of the body may be configured to have a clearance of 1 millimeter or less when disposed in the burr hole.

An assembly may include the burr hole device, the catheter, and a sheath. The sheath may include a sheath body defining a sleeve lumen configured to receive the catheter, (ii) a recording electrode disposed on the sheath body, (iii) the cable, and (iv) a conductor electrically coupled to the recording electrode and extending in the cable. The catheter may be a therapeutic fluid delivery catheter, a catheter of a ventriculoperitoneal (VP) shunt, a catheter of an external ventricular drain (EVD), a catheter for aspirating CSF, or the like. The assembly may comprise a VP shunt, an EVD, an infusion device, which may be an implantable infusion device, configured to connect to the therapeutic fluid delivery catheter, or the like.

A method may include disposing the burr hole device in or about a burr hole of a subject; inserting the catheter through the lumen of the burr hole device; inserting the catheter through the sheath lumen; implanting a distal end of the catheter in a brain of the subject; implanting the recording electrode of the sheath beneath the skull of the subject; inserting the cable of the sheath in the bottom groove, the second top groove, or the bottom portion of the top groove, depending on which burr hole device is employed; and inserting the catheter in the top groove, the first top groove, or the top portion of the top groove.

In an aspect, the present disclosure describes a burr hole device. The burr hole device is configured to be inserted into a burr hole of a subject and to be secured against a side of the burr hole.

In an embodiment, a burr hole device comprises a body having a top surface and a bottom surface and defining a lumen extending from the top surface to the bottom surface. The lumen may be configured to receive one or both of a cable of a sheath or lead and a catheter. The catheter may be configured to infuse fluid to, or withdraw fluid from, a brain of a subject. At least a portion of the body of the burr hole device is configured to be inserted into a burr hole. The burr hole device comprises an expansion member that may be deployed when the body is in the burr hole. The expansion member is configured to expand against a side of the burr hole to anchor the body within the burr hole. The expansion member is deployable from a retracted state to an expanded state. When the expansion member is in the retracted state, the body is slidably receivable in the burr hole. The expansion member may be operatively coupled to a user actuatable member that, when actuated, causes the expansion member to adapt the expanded state. The burr hole device may optionally comprise a portion configured to be disposed on a surface of the skull. For example, the configured to be disposed on a surface of the skull may be an upper flange portion. The portion configured to be disposed on a surface of the skull may comprise a groove for receiving the cable.

An assembly may include the burr hole device, the catheter, and a sheath. The sheath may include a sheath body defining a sleeve lumen configured to receive the catheter, (ii) a recording electrode disposed on the sheath body, (iii) the cable, and (iv) a conductor electrically coupled to the recording electrode and extending in the cable. The catheter may be a therapeutic fluid delivery catheter, a catheter of a ventriculoperitoneal (VP) shunt, a catheter of an external ventricular drain (EVD), a catheter for aspirating CSF, or the like. The assembly may comprise a VP shunt, an EVD, an infusion device, which may be an implantable infusion device, configured to connect to the therapeutic fluid delivery catheter, or the like.

A method may include disposing the burr hole device in or about a burr hole of a subject; inserting the catheter through the lumen of the burr hole device; inserting the catheter through the sheath lumen; implanting a distal end of the catheter in a brain of the subject; implanting the recording electrode of the sheath beneath the skull of the subject; inserting the cable of the sheath in the bottom groove, the second top groove, or the bottom portion of the top groove, depending on which burr hole device is employed; and inserting the catheter in the top groove, the first top groove, or the top portion of the top groove.

In an aspect, the present disclosure describes a burr hole device having an electrode. The burr hole device is configured to receive a catheter for delivering fluid to or withdrawing, shunting, or draining fluid from a brain of a subject and to receive electrical brain activity data via the electrode.

In embodiments, the burr hole device includes a body having a top surface and a bottom surface and defining a lumen extending from the top surface to the bottom surface. The body defines an upper flange portion and a lower portion. The lower portion is configured to be placed within the burr hole. The upper flange portion is configured to be disposed on the surface of the skull. The lumen is configured to receive a catheter configured to infuse fluid to, or withdraw fluid from, a brain of a subject. The burr hole device comprises an electrode disposed on the bottom surface of the lower portion.

The burr hole device may be configured such that the bottom surface of the lower portion is placed on a surface of a brain or above the surface of the brain when the burr hole device is implanted.

The burr hole device may have an electrical interconnect electrically coupled to the electrode. The electrical interconnect may be configured to electrically couple to an implantable medical lead.

An assembly may comprise the burr hole device and the catheter. The assembly may further comprise a sheath. The sheath may include a sheath body defining a sleeve lumen configured to receive the catheter, (ii) a recording electrode disposed on the sheath body, (iii) a cable, and (iv) a conductor electrically coupled to the recording electrode and extending in the cable. The burr hole device may comprise a groove configured to receive the cable. The catheter may be a therapeutic fluid delivery catheter, a catheter of a ventriculoperitoneal (VP) shunt, a catheter of an external ventricular drain (EVD), a catheter for aspirating CSF, or the like. The assembly may comprise a VP shunt, an EVD, an infusion device, which may be an implantable infusion device, configured to connect to the therapeutic fluid delivery catheter, or the like.

A method may include operatively coupling to signal apparatus the electrode disposed on the bottom surface of the lower portion of the body of the burr hole device.

A method may include disposing the burr hole device in or about a burr hole of a subject; inserting the catheter through the lumen of the burr hole device; and implanting a distal end of the catheter in a brain of the subject. The method may further include inserting the catheter through the sheath lumen; implanting the recording electrode of the sheath beneath the skull of the subject; and inserting the cable of the sheath in a groove of the burr hole device.

In an aspect, the present disclosure describes a burr hole device configured to receive a port device operatively couplable to a catheter for delivering fluid to, or withdrawing, shunting, or draining fluid from, a brain of a subject. The burr hole device is also configured to receive the catheter and comprises an electrode configured to detect brain electrical activity data.

In an aspect, the present disclosure describes an implantable sheath configured to receive a catheter and having an electrode configured to detect brain electrical activity data. The sheath and the catheter may be used with various embodiments of burr hole devices described herein.

In embodiments, an implantable sheath includes a body having a proximal end and a distal end and defining a lumen from the proximal end to the distal end. The lumen is configured to receive a catheter. The sheath comprises an electrode disposed on the body and a cable extending from the body in proximity to the proximal end. The sheath may comprise more than one electrode. One or more electrodes may be sensing electrodes. One or more electrodes may be referential electrodes. The sheath comprises a conductor electrically coupled to the electrode and extending in the cable. The cable comprises an electrical interconnect comprising a contact electrically coupled to the conductor. The sheath may be configured to be completely implanted in a subject.

An assembly may include the sheath, the catheter, and a burr hole device as described herein. The catheter may be a therapeutic fluid delivery catheter, a catheter of a ventriculoperitoneal (VP) shunt, a catheter of an external ventricular drain (EVD), a catheter for aspirating CSF, or the like. The assembly may comprise a VP shunt, an EVD, an infusion device, which may be an implantable infusion device, configured to connect to the therapeutic fluid delivery catheter, or the like.

In an aspect, the present disclosure describes a method for implanting a catheter and a sheath in a subject. The sheath may comprise (i) a sheath body defining a sleeve lumen configured to receive the catheter, (ii) one or more electrode, such as one or more recording or referential electrodes, disposed on the sheath body, (iii) a cable, and (iv) a conductor electrically coupled to the recording electrode and extending in the cable. When implanted a distal end of the catheter may be position in a brain of the subject and the electrode may be positioned in the brain.

In embodiments, the method comprises creating a first burr hole having a first diameter in a skull of a subject wherein the skull defines an edge of the first burr hole; and creating a second burr hole having a second diameter in skull. The second diameter is smaller than the first diameter. The first and second burr holes partially overlap. The first burr hole may be configured to receive a catheter or a burr hole device. The second burr hole may be configured to receive a cable of a sheath.

The method may further comprise creating a trench in the top surface of the skull. The trench may have a first end and a second end. The first end of the trench may intersect the second burr. The trench may extend away from the second burr hole towards the second end. The trench may have a first depth at the first end. The trench may have a second depth at the second end. The first depth may be greater than the second depth. The trench may be configured to receive a cable of a sheath.

The details of one or more aspects of the disclosure are set forth in the accompanying drawings and the description below. Other features, objects, and advantages of the techniques described in this disclosure will be apparent from the description and drawings, and from the claims.

Definitions and Context for Defined Terms

All scientific and technical terms used herein have meanings commonly used in the art unless otherwise specified. The definitions provided herein are to facilitate understanding of certain terms used frequently herein and are not meant to limit the scope of the present disclosure.

As used herein, "disposed on" in the context of an electrode on a body, such as a sheath body refers to the electrode being associated with the body in a manner such that the position of the electrode maintains a position relative to the body and at least a portion of the electrode is exposed to tissue or fluid of a subject when the body is implanted in the subject. The electrode may be bonded, fastened, or adhered to the body, may be recessed into a portion of the body, or may be otherwise retained by the body, or the like.

As used herein, a "cable" is an assembly of one or more electrical conductors, such as wires, running along a length of the cable. The electrical conductors may be used to carry electric current. The conductors may be electrically insulated from one another. The conductors may be electrically insulated from the exterior of the cable by the material employed in forming the cable.

As used herein, "diameter" refers to the largest distance from one edge to another of an object along a section orthogonal to a longitudinal axis of the object. If the object is cylindrical, the diameter will be constant along the section. If the object is a rectangular prism having a square cross-section, the diameter is the distance from one corner of the square to the opposing corner of the square.

The terms "coupled" or "connected" refer to elements being attached to each other either directly (in direct contact with each other) or indirectly (having one or more elements between and attaching the two elements). Either term may be replaced to "couplable" or "connectable" to describe that the elements are configured to be coupled or connected. In addition, either term may be modified by "operatively" and "operably," which may be used interchangeably, to describe that the coupling or connection is configured to allow the components to interact to carry out functionality.

As used herein, "treat," "treatment," or the like mean to reduce or alleviate one or more symptom or to slow the progression of the disease being treated.

As used herein, "intracranial" means within the skull of a subject. An intracranial electrode may be placed at any suitable location within the confines of a skull of a subject. For example, the intracranial electrode may be placed in the brain of the subject or on a surface of the brain of the subject. An intracranial electrode may be placed in brain parenchyma ("intraparenchymal"). An intracranial electrode may be placed within the cerebrum of a subject ("intracerebral"). An intracranial electrode may be placed within an intracranial blood vessel ("intravascular"). An intracranial electrode may be placed within a cerebral ventricle ("intraventricular"). iEEG signals include signals obtained from electrodes positioned on the surface of the brain of a subject and within the brain of the subject, including electrodes placed intraparenchymally, intracerebrally, intraventricular, and intravascularly.

As used herein, "withdrawing" fluid, such as cerebrospinal fluid (CSF), from a brain means removing the fluid from the brain. The removed fluid may be tested to determine one or more properties of the fluid, such as the concentration of one or more components of the removed fluid. The removed fluid, such as CSF, may be shunted to another location of the subject. The removed fluid may be drained from the subject. In some instances, the present disclosure discusses withdrawing, shunting, or draining CSF from the subject. In other instances, the present disclosure discusses withdrawing CSF from the subject without discussing shunting or draining. "Withdrawing" and "withdrawing, shunting, or draining" or the like, in the context of fluid relative to the brain, are used interchangeably herein.

As used herein, a "brain state" is a symptom or function of the brain that (i) involves multiple areas and neuronal networks of the brain and (ii) is reflected in brain activity. A brain state may be manifest in normal or abnormal brain activity. Motor function, speech function, visual function, somatosensory sensation function, smell function, and the like, in and of themselves, are not brain states. These functions, in and of themselves, impact smaller, more discrete, less distributed regions of the brain. For example, visual function involves the visual cortex, visual radiations, and optic tract. A brain state may, however, involve one or more of motor function, speech function, visual function, smell function, and the like. A brain state may involve activity in 2 or more Brodmann areas, 3 or more Brodmann areas, 4 or more Brodmann areas, 5 or more Brodmann areas, 6 or more Brodmann areas, 7 or more Brodmann areas, 8 or more Brodmann areas, 9 or more Brodmann areas, or 10 or more Brodmann areas.

As used herein, a "psychological brain state" is a brain state having a mental or emotional component. A subject is typically aware of their psychological brain state in their feelings and thoughts. Examples of psychological brain states include general affect or mood, anxiety, depression, addiction, obsession, suicidal thoughts, hallucinations, cognition, attention, post-traumatic stress, and the like, and degrees thereof. As an example, a traumatic memory may involve one area of the brain, but post-traumatic stress disorder (PTSD) is the impact of that memory which distracts attention, causes fear, and/or impacts cognitive function. Accordingly, PTSD involves or impacts multiple regions and neural networks of the brain.

Psychological brain states do not include seizure activity and/or motor activity alone. However, electrical brain activity associated with epileptic and/or motor activity may be relevant to a broader psychological brain state.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

As used herein, singular forms "a," "an" and "the" include plural referents unless the context clearly dictates otherwise.

As used herein, the term "or" is generally employed in its sense including "and/or" unless the content clearly dictates otherwise. The term "and/or" means one or all the listed elements or a combination of any two or more of the listed elements. The use of and/or in some locations of the present disclosure is not intended to mean that the use of "or" in other locations cannot be interpreted as "and/or."

The phrases "at least one of" and "one or more of" followed by a list refers to any one of the items in the list and any combination of two or more items in the list.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

Any direction referred to herein, such as "top," "bottom," "side," "upper," "lower," and other directions or orientations are described herein for clarity and brevity but are not intended to be limiting of an actual device or system. Devices and systems described herein may be used in a number of directions and orientations.

As used herein, "providing" an article, device, or system means manufacturing the article, device, or system, assembling the article, device, or system, purchasing the article, device, or system, or otherwise obtaining the article, device, or system.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must).

The words "include," "including," and "includes" indicate open-ended relationships and therefore mean including, but not limited to. Similarly, the words "have," "having," and "has" also indicated open-ended relationships, and thus mean having, but not limited to. Similarly, the terms "comprise" and "comprising" indicate open-ended relationships, and thus mean comprising, but not limited to. The terms "consisting essentially of" and "consisting of" are subsumed within the term "comprising." For example, a catheter comprising tubing may be a catheter consisting of tubing. The term "consisting essentially of" means a recited list of one or more items belonging to an article, kit, system, or method and other non-listed items that do not materially affect the properties of the article, kit, system, or method.

The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a catheter connector may be configured to place a lumen of a catheter in fluid communication with a fluid path, even when the catheter is not connected to the catheter connector).

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

BRIEF DESCRIPTION OF THE DRAWINGS

Figure 20:
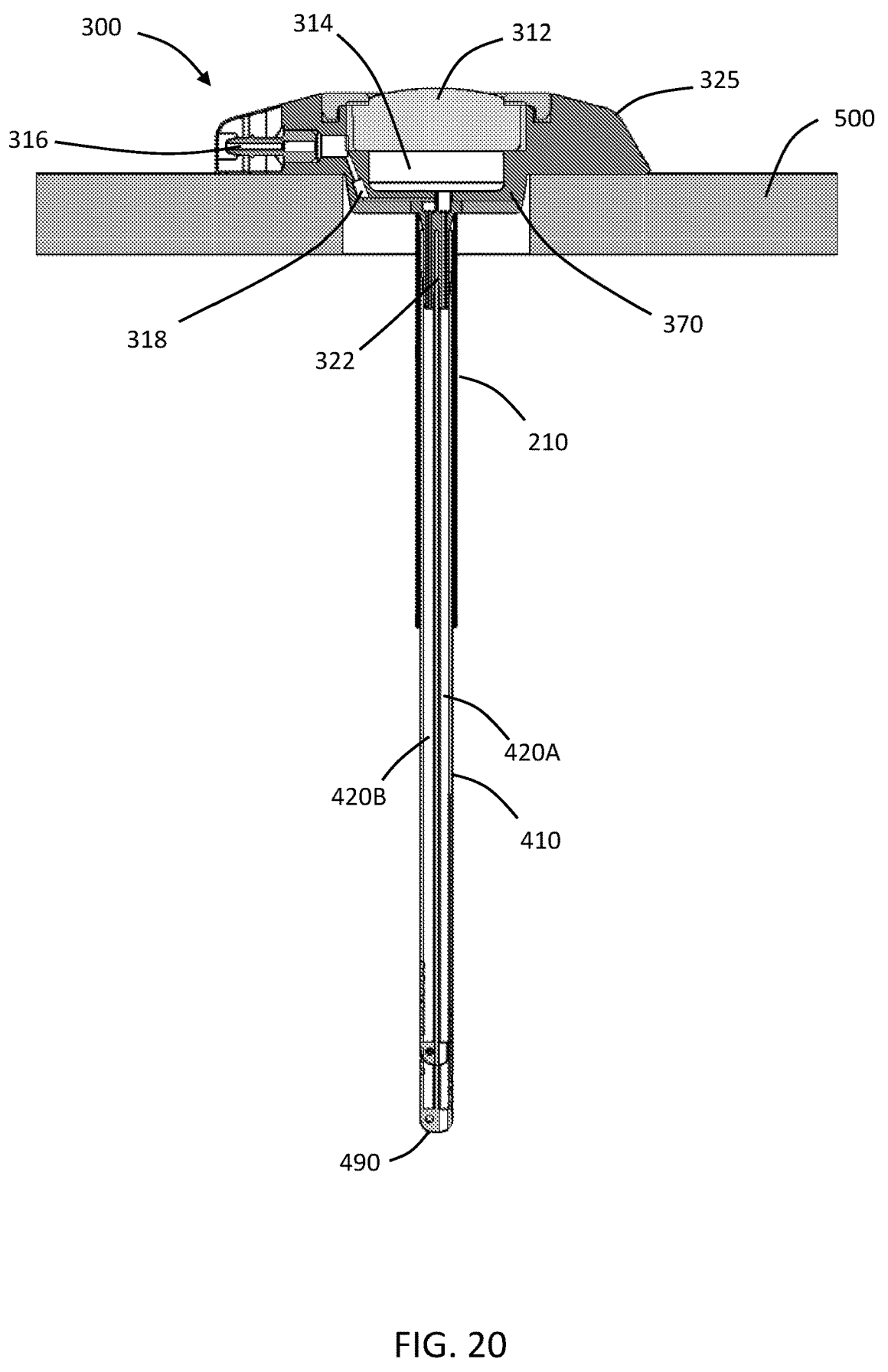

FIG. 20 is a schematic cross-sectional view of the assembly of FIG. 18 relative to a bottom surface of the skull.

Figure 1:
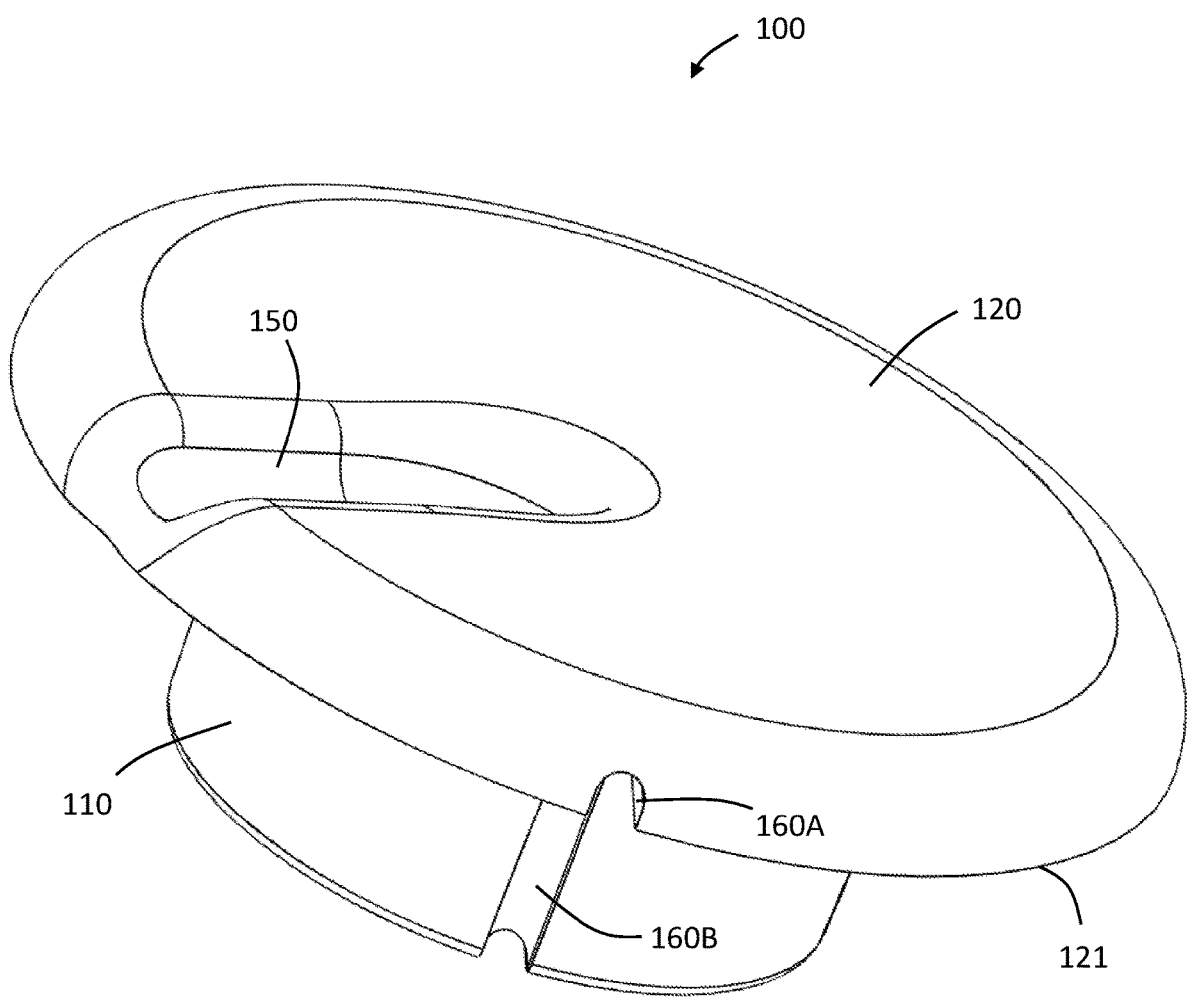
FIGS. 1-3 are a schematic perspective views of an embodiment of a burr hole device.
Figure 2:
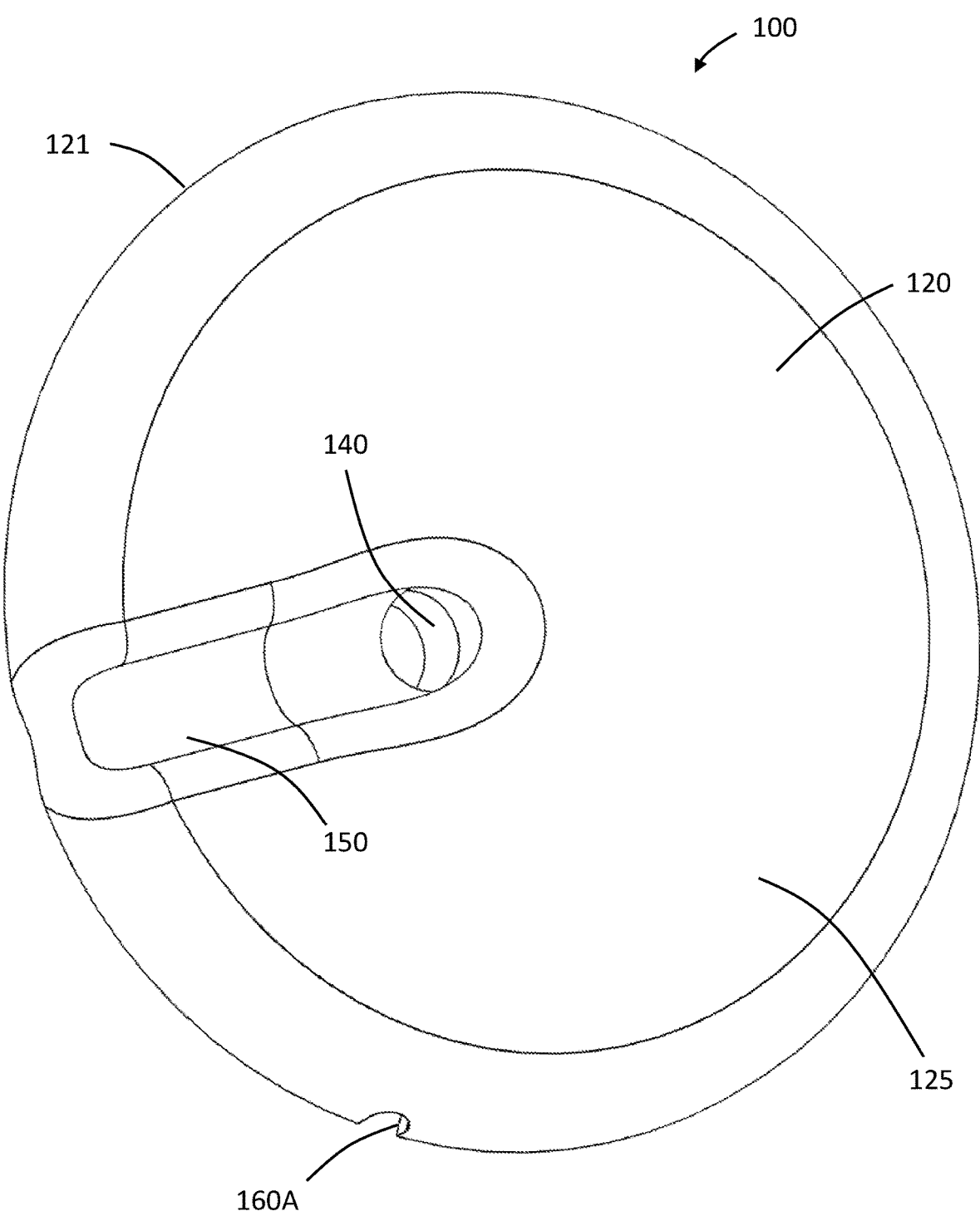
Figure 3:
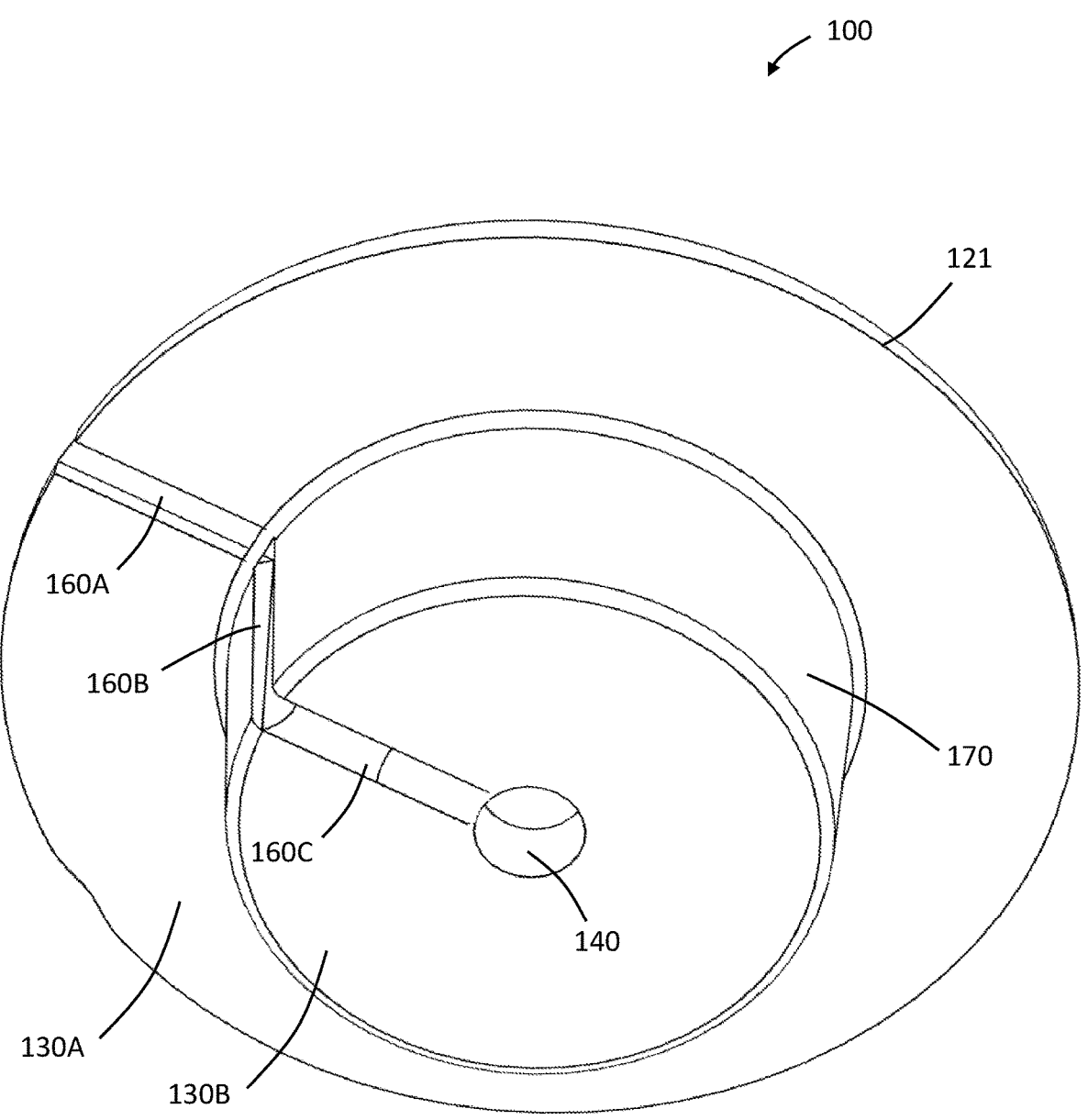

While the invention is susceptible to various modifications and alternative forms, specific embodiments thereof are shown by way of example in the drawings and may herein be described in detail. The schematic drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

Like numbers used in the figures refer to like components. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components.

Features or elements shown in a given figure that are not shown in another figure may be present in the other figure in which the features or elements are not shown. That is, the features and elements shown in the figures are interchangeable. For example, an embodiment of a burr hole device that is shown in the figures without through openings configured to receive screws, an electrical interconnect, a cable, or any other feature or element may, in other embodiments, include through openings, an electrical interconnect, a cable, or any other feature or element illustrated in other figures.

DETAILED DESCRIPTION

The present disclosure relates to, among other things, devices and systems configured for use with a catheter for delivering therapeutic agents to the brain or withdrawing CSF from the brain. The devices and systems may include a sheath configured to receive the catheter. The sheath may include an electrode configured to be intracranially positioned for recording brain activity data. The devices and systems may include a burr hole apparatus configured to receive the catheter and the sheath or portions thereof.

FIGS. 1, 2, 3, and 4A show an embodiment of a burr hole device 100 configured for use with a catheter for delivering fluid to or removing fluid from a brain of a subject. The burr hole device 100 is also configured to receive a cable. The cable may comprise a conductor electrically coupled to an electrode. The electrode may be disposed on the catheter, a lead, or a sheath configured to receive the catheter.

The burr hole device 100 has a body 110 having a top surface 120 and a bottom surface 130A, 130B and defining a lumen 140 extending from the top surface 120 to the bottom surface 130. The lumen 140 is configured to receive a catheter configured to allow fluid to flow to or from a brain of a subject. For example, the catheter may be configured to deliver fluid therapeutic or diagnostic compositions to the brain of the subject, may be configured to permit aspiration of cerebral spinal fluid (CSF) from the brain of the subject, may be configured to drain or shunt CSF from the brain of the subject, or the like.

The body 110 defines a top groove 150 along the top surface 120. The top groove 150 extends from the lumen 140 towards a lateral edge 121 of the top surface 120 of the body 110. The top groove 150 is configured to receive the catheter as the catheter exits the lumen 140. The top groove 150 may be configured to snuggly or grippingly engage the catheter to retain the catheter relative to the burr hole device 100. Alternatively, the top groove may be configured to loosely receive the catheter so that the catheter may be readily removed from the brain by pulling on a proximal portion of the catheter at a distance from the burr hole device 100. Such ease of removal may be beneficial for certain catheters where explant is routine, such as with catheters that are part of an external ventricular drain (EVD) apparatus. Often, EVD catheters exit the skin of the subject at a distance from the burr hole. Explanting the EVD catheter by pulling on an externalized portion of the catheter may be more desirable than reopening the scalp in proximity to the burr hole to remove the catheter.

The body 110 of the burr hole device 100 depicted in FIGS. 1-4 defines an upper flange portion 125 and a lower portion 170. The lower portion 170 is configured to be placed within the burr hole. Preferably, the lower portion 170 of the body 110 has a clearance of 1 millimeter or less when disposed in the burr hole to help stabilize the device 100 when implanted. In embodiments, the lower portion 170 of the body 110 has an outer diametric dimension $OD_L$ in a range from 3 millimeters to 20 millimeters, which outer diametric dimension may depend on the size of the burr hole. In embodiments, the lower portion 170 of the body 110 has an outer diametric dimension $OD_L$ in a range from 10 millimeters to 20 millimeters. In embodiments, the lower portion 170 of the body 110 has an outer diametric dimension $OD_L$ in a range from 5 millimeters to 14 millimeters, such as from about 11 millimeters to about 13 millimeters. Typically, the outer surface of the lower portion 170 is generally cylindrical as depicted in FIGS. 1, 2, 3, and 4A or frustoconical, and the lower portion 170 of the device 100 may have a generally circular cross-section.

When the burr hole device 100 is implanted, a bottom surface 130B of the lower portion 170 of the device 100 preferably does not extend substantially beyond the bottom of skull when received in the burr hole. Accordingly, the height of lower portion 170 may vary depending on the thickness of the skull of the subject into which the burr hole device 100 is implanted. As an example, a thickness of a human adult skull may typically be in a range from about 6.5 millimeters to about 7 millimeters.

In some embodiments, the height of the lower portion 170 ($H_L$) of the burr hole device 100 (distance from the bottom surface 130A of the upper flange portion 125 to the bottom surface 130B of the lower portion 170) is in a range from about 3 millimeters to about 7 millimeters. For example, the height of the lower portion 170 may be in a range from about 4 millimeters to about 6 millimeters or from about 4.5 millimeters to about 5.5 millimeters.

The upper flange portion 125 is configured to be disposed on the surface of the skull adjacent to the burr hole. That is, the bottom surface 130A of the upper flange portion 125 may rest on the skull when the device 100 is implanted. The upper flange portion 125 has an outer diametric dimension $OD_U$ that is greater than the diameter of the burr hole. In embodiments, the outer diametric dimension $OD_U$ of the upper flange portion 170 is in a range from 15 millimeters to 30 millimeters.

The bottom surface 130A of the upper flange portion 125 defines a bottom groove 160A configured to receive a cable comprising a conductor electrically coupled to an electrode configured to be implanted in the brain of the subject. The bottom groove 160A extends from a lateral edge 121 of the bottom surface 130A towards the lumen 140. The cable may be protected by the bottom groove 160A when implanted, rather than being pinched between the upper surface of the skull and the bottom surface 130A of the upper flange portion 125.

The lower portion 170 of the device 100 may define a side groove 160B that may run the length of the lower portion 170. The side grove 160B intersects with and meets bottom groove 160A. The side groove 160B is configured to receive the cable such that the cable. The cable may be positioned in the side groove 160B between the side of the burr hole and the body 110 of the lower portion 170 when the burr hole device 100 is implanted. When clearances are small between the lower portion 170 and the burr hole, the cable may be protected in the side groove 160B, as opposed to being pinched between the lower portion 170 of the device 100 and the side of the burr hole.

The burr hole device 100 may optionally comprise bottom groove 160C as depicted in FIGS. 1, 2, 3, and 4A. Bottom groove 160C extends from the lumen 140 to a lateral edge of the bottom surface 130B of the lower portion 170 of the burr hole device 170. Bottom groove 160C may intersect and meet with side groove 160B.

Figure 4A:
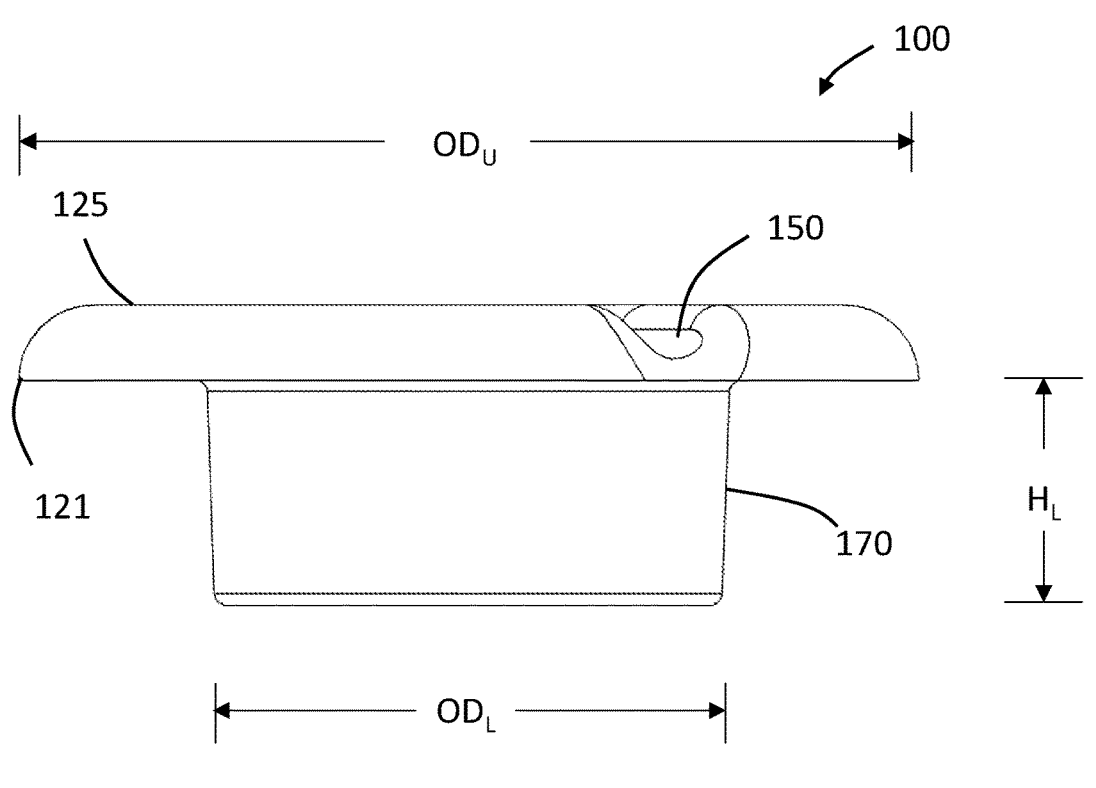
FIG. 4A is a schematic side view of the burr hole device of FIGS. 1-3.
Figure 4B:
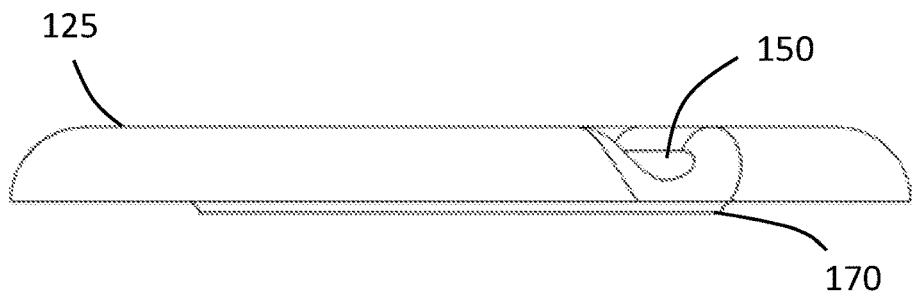
FIGS. 4B and 4C are side views of alternative embodiments of burr hole devices.
Figure 4C:

In embodiments, a burr hole device 100 lacks a lower portion 170 or has a lower portion 170 with having a small height, as depicted in FIGS. 4B and 4C. The height of the lower portion in FIG. 4B may range from about 0.1 millimeters to about 1 millimeter. The lower portion 170 may be inserted into a burr hole to assist with aligning the top upper portion 125 relative to the burr hole. The upper flange portion 125 may include a groove 150 for receiving a portion of a catheter.

When the burr hole device 100 lacks a lower portion as shown in FIG. 4C, the burr hole device may be visually aligned over the burr hole.

Figure 5:
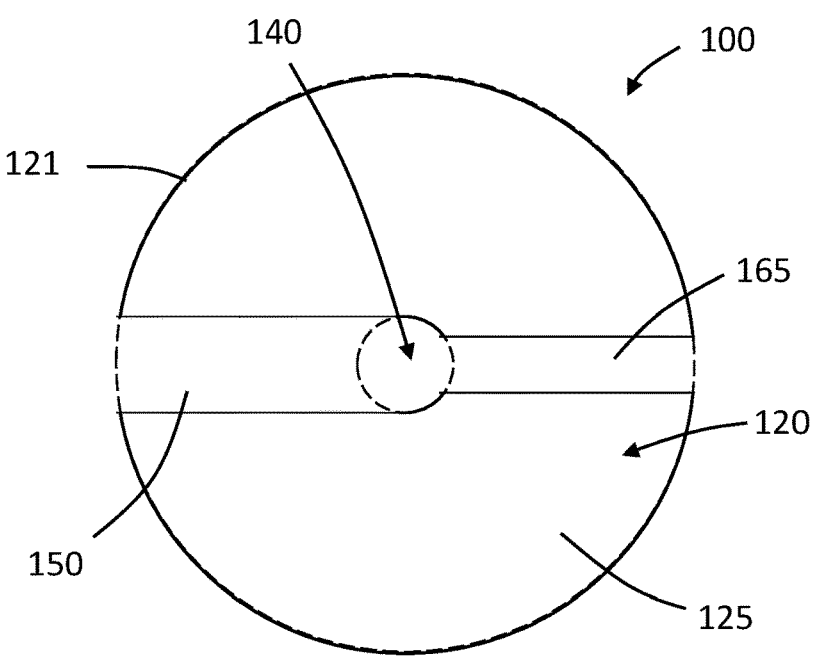
FIGS. 5-7 are schematic top views of embodiments of burr hole devices.
Figure 6:
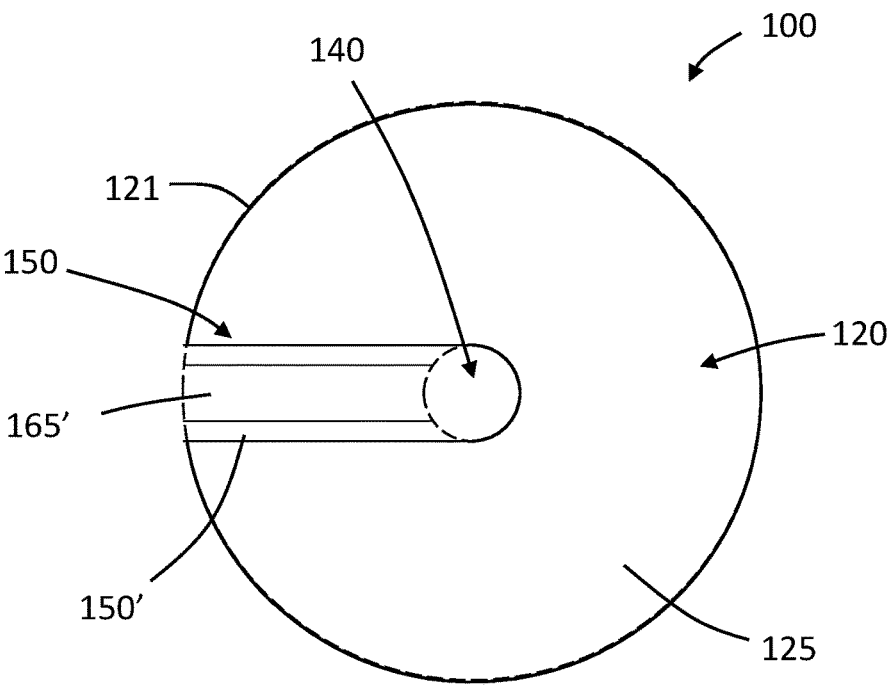
Figure 7:
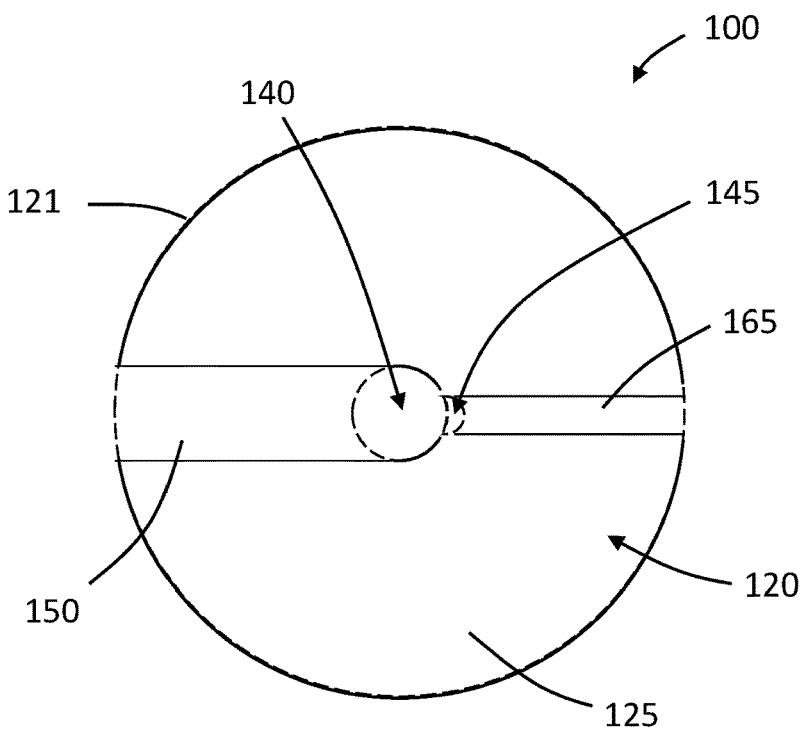

FIGS. 5-7 show embodiments of burr hole devices 100 having a groove 165 configured to receive a cable, such as a cable of a sheath, on the top surface 120 of the upper flange portion 125. The burr hole devices 100 of FIGS. 5-7 may, otherwise, be similar to the burr hole devices 100 shown in FIGS. 1-3 and 4A-C. The burr hole devices 100 of FIGS. 5-7 may have some or all features or elements of the burr hole devices 100 of FIGS. 1-3 and 4A-C. For example, the devices 100 of FIGS. 5-7 may comprise a bottom groove 160A (or a bottom grooves 160A, 160C) or a bottom groove 160A (or a bottom grooves 160A, 160C) and a side grove 160B as shown in FIGS. 1-4. By having grooves for a cable on the bottom surface 130A (or 130A and 130B) and the top surface 120, the burr hole device 100 may be used with a variety of different configurations of cables, such as cables of sheaths. Having grooves for a cable on the bottom surface 130A (or 130A and 130B) and the top surface 120, the burr hole device 100 may also provide the implanting physician with options for different routes for cable feedthrough on a case-by-case basis.

As shown in FIG. 5, the top surface 120 of the upper flange portion 125 of the burr hole device 100 defines a first top groove 150 configured to receive a catheter and a second top groove 165 configured to receive a cable. The first 150 and second 165 top grooves extend from the lumen 140 to a lateral edge 121 of the top surface 120. A portion of the catheter and a portion of the cable may exit the lumen 140 and may be placed in the respective top groove 150, 165. The first top grove 150 may be configured to snuggly or grippingly receive the catheter or may be configured to loosely receive the catheter. The second top groove 165 may be configured to snuggly or grippingly receive the cable or may be configured to loosely receive the cable.

While the first top groove 150 and second top groove 165 shown in FIG. 5 extend in generally opposite directions from the lumen 140 across the top surface 120, they may extend in any suitable orientation relative to one another.

As shown in FIG. 6, the top surface 120 of the upper flange portion 125 of the burr hole device 100 defines a top groove 150 extending from the lumen 140 towards a lateral edge 121 of the top surface 120. The top groove 150 comprises a lower groove portion 165' and an upper groove portion 150'. The lower groove portion 165' is configured to receive a cable and has a smaller diametric dimension than the upper groove portion 150', which is configured to receive a catheter. The upper groove portion 150' is configured to receive the catheter such that the catheter is positioned over the cable when the both the cable and the catheter are received in the top groove 150. A portion of the catheter and a portion of the cable may exit the lumen 140 and may be placed in the respective top groove portion 150', 165'. The upper top grove portion 150' may be configured to snuggly or grippingly receive the catheter or may be configured to loosely receive the catheter. The lower top groove portion 165' may be configured to snuggly or grippingly receive the cable or may be configured to loosely receive the cable.

In FIG. 7, the burr hole device 100 has a first lumen 140 extending through the body from the top surface 120 to the bottom surface (e.g., 103B as shown in FIGS. 1-4). The burr hole device 100 has a second lumen 145 extending through the body from the top surface 120 to the bottom surface. The first 140 and second 145 lumens partially overlap. The first top groove 150, which is configured to receive a catheter, extends from the first lumen 140 to a lateral edge 121 of the upper surface 120 of the body 110. The second top groove 165, which is configured to receive a cable, extends from the second lumen 145 to a lateral edge 121 of the upper surface 120 of the body 110. The diameter of the second lumen 145 is smaller than the diameter of the first lumen 140. The first lumen 140 is configured to receive the catheter. The second lumen 145 is configured to receive the cable.

While the first top groove 150 and second top groove 165 shown in FIG. 5 extend in generally opposite directions from the lumen 140 across the top surface 120, they may extend in any suitable orientation relative to one another.

It should be understood that the burr hole device 100 shown in FIG. 6 may be readily modified to include a second lumen 145 (and the lower grove portion 165' may extend from the second lumen 145) as shown in FIG. 7.

Figure 8:
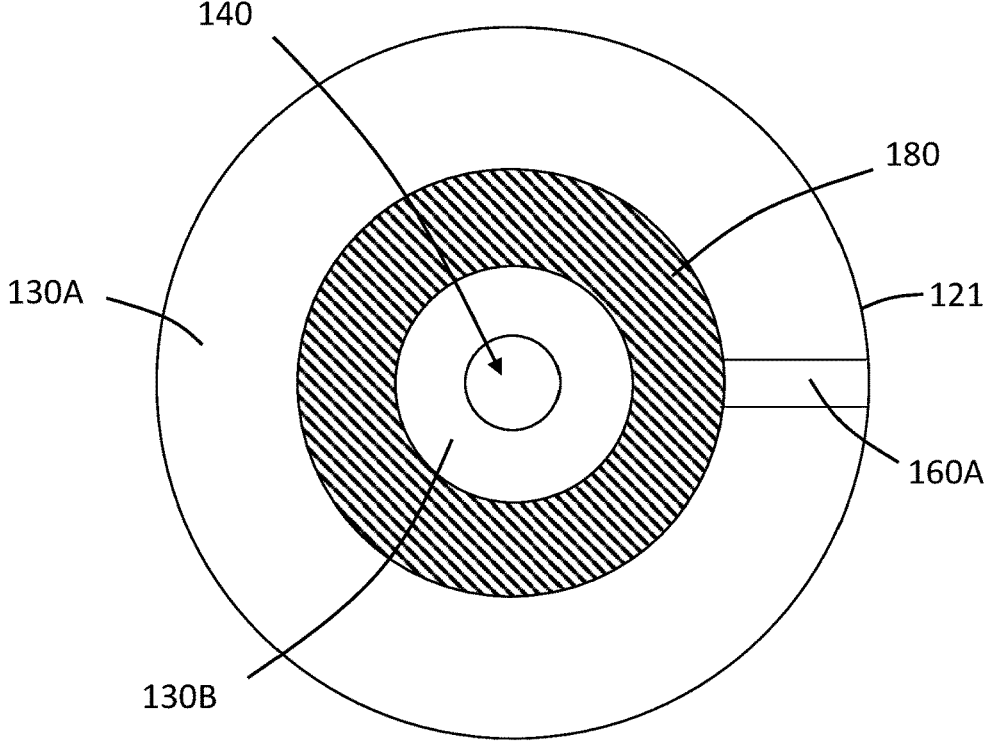
FIG. 8 is a schematic bottom plan view of an embodiment of a burr hole device having an electrode.
Figure 9:
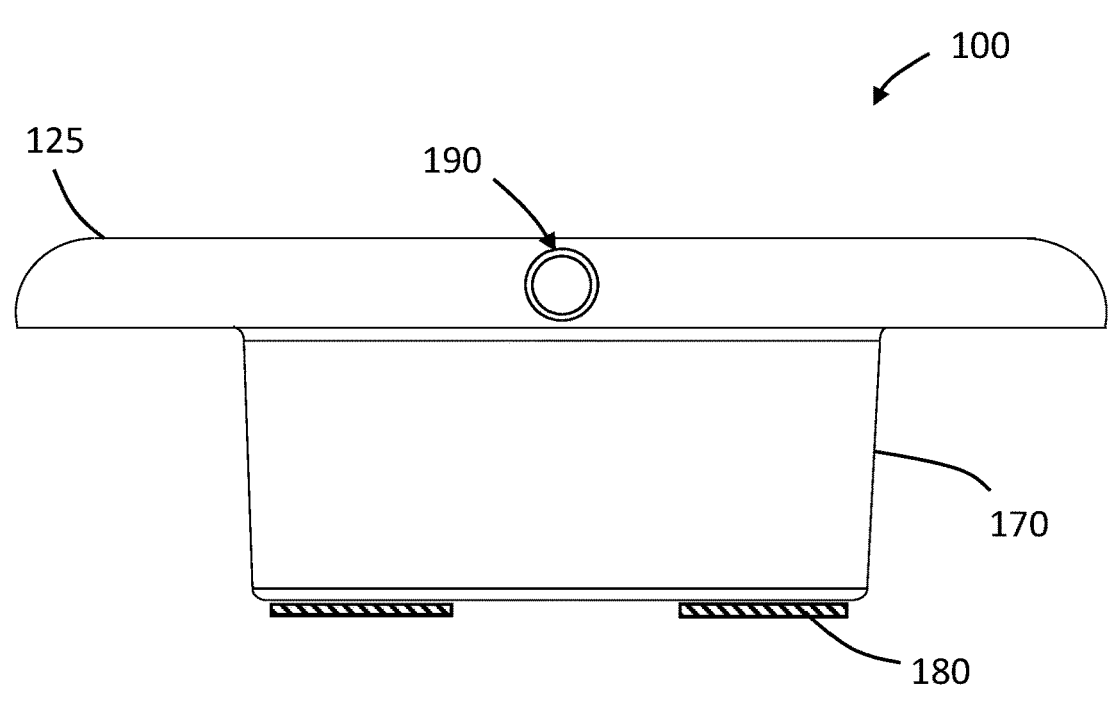
FIGS. 9-10 are side plan views of embodiments of the device shown in FIG. 8.
Figure 10:
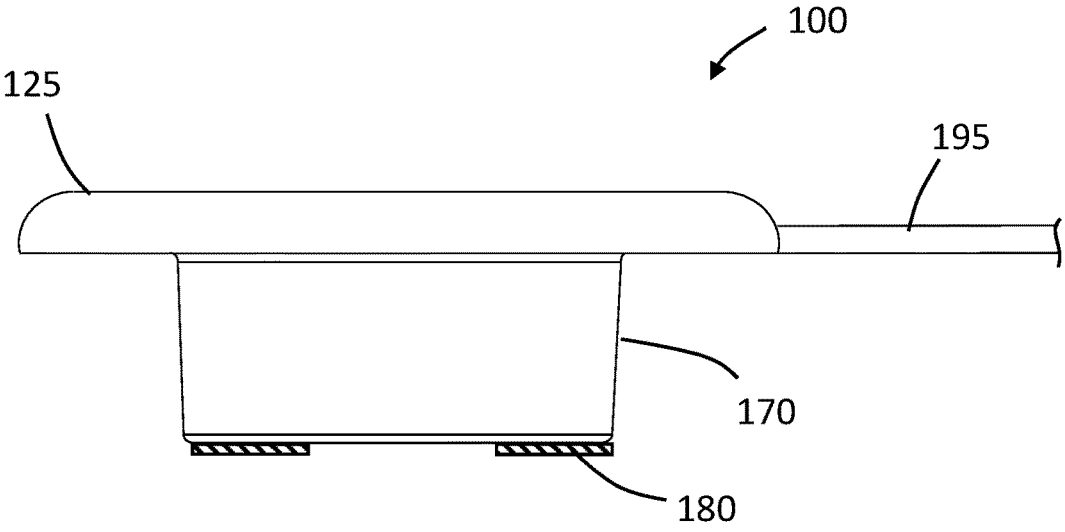

FIGS. 8-10 show embodiments of burr hole devices 100 having an electrode 180. The electrode 180 may be configured to detect brain electrical activity, such as EEG signals or to act as a return path for electrical sensing with other electrodes. The burr hole devices 100 of FIGS. 8-10 may, otherwise, be similar to the burr hole device 100 shown in FIGS. 1-7. The burr hole devices 100 of FIGS. 8-10 may have some or all features or elements of the burr hole device 100 of FIGS. 1-7.

The electrode 180 is disposed on or may be in proximity to the bottom surface 130B of the lower portion 170 of the burr hole device 100. Disposing the electrode 180 on or in proximity to the bottom surface 130B may place the electrode 180 on or in proximity to a surface of the brain when the lower portion 170 of the burr hole device 100 is positioned in the burr hole.

In embodiments, the electrode 180 is disposed on at least a portion of the bottom surface 130B of the burr hole device 100. The electrode 180 may be annular as shown in FIG. 8 or may have any other suitable shape. The electrode may extend over the entire bottom surface 130B or over a portion of the bottom surface 130B of the device 100. More than one electrode (not shown) may be disposed on the bottom surface 130B of the device 100.

The electrode 180 may serve as a ground electrode, reference electrode, or working electrode, or combinations thereof. The electrode 180 may be operatively couplable with signal apparatus that processes signals from the electrode 180 and other electrodes.

The electrode 180 may be made from any suitable material. Suitable materials for implantable electrodes are well-known to those of skill in the art. Materials suitable for deep brain stimulation electrodes are suitable materials for electrodes of the catheters described herein. In embodiments, the electrode 180 is made from platinum or a platinum iridium alloy.

The electrode 180 may have any suitable thickness. For example, the electrode 180 may have a thickness from about 100 microns to about 3 millimeters, such as from about 200 microns to about 2 millimeters. The electrode 180 may be formed from a foil.

As shown in FIG. 9, the burr hole device 100 may include an electrical interconnect 190 electrically coupled to the electrode 180. A conductor may run through the body of the burr hole device 100 from the electrode 180 to a contact of the electrical interconnect 190. The electrical interconnect 190 may be configured to electrically couple with an implantable medical lead or suitable wire for carrying electrical signals from the burr hole device 100 to signal apparatus for processing or transmitting signals received by the electrode 180.

As shown in FIG. 10, the burr hole device 100 may comprise a cable 195 electrically coupled to the electrode 180. The cable 195 may comprise a conductor electrically coupled to the electrode 180. The cable 195 may comprise a contact (not shown) for electrical connection to, for example, signal apparatus.

The burr hole device 100 having an electrode 180 may comprise a bottom groove 160A on the bottom surface 130A of the upper flange portion 125, and may also comprise a side groove (e.g., 160B as shown in the device of FIGS. 1-4) along the side of the lower portion 170 that meets with the bottom groove 160A. The bottom groove 160A and side groove, if present, may receive a cable. The cable may comprise a conductor electrically coupled to the electrode 180.

In embodiments, the bottom groove 160A and side groove, if present, receive a cable comprising a conductor electrically coupled to an electrode disposed on the catheter or a sheath.

The burr hole device 100 may comprise an electrical interconnect 190 or a cable 195 and may comprise a bottom groove 160A and optional side groove. Accordingly, the burr hole device 100 is configured to allow signals from the electrode 180 of the burr hole device 100 and electrodes of other devices, such as a catheter or sheath, used with the burr hole device 100 to be delivered to, for example, signal apparatus. Signals from electrodes of the associated devices may be carried through a cable received in the bottom groove 160A and optional side groove, and signals from the electrode 180 of the burr hole device 100 may be carried through the cable 195 or electrical interconnect 190.

FIGS. 11-14 show an embodiment of a burr hole device 100 configured to receive a cranial port device. The burr hole device 100 of FIGS. 11-14 may, otherwise, be similar to the burr hole device 100 shown in FIGS. 1-10. The burr hole devices 100 of FIGS. 11-14 may have some or all features or elements of the burr hole device 100 of FIGS. 1-10.

The burr hole device 100 may be configured to receive any suitable cranial port device. For example, the burr hole device 100 may receive a ventriculoperitoneal shunt valve housing, an Ommaya reservoir, a cranial port device as described in, for example, U.S. 2022/016338-A1, entitled IMPLANTABLE CRANIAL MEDICAL DEVICE, filed on Jul. 15, 2021, and published on Jan. 20, 2022, which published patent application is hereby incorporated herein in its entirety by reference to the extent that it does not conflict with the disclosure presented herein, or the like.

The burr hole device 100 of FIGS. 11-14 includes a body 110 defining an upper flange portion 125 and a lower portion 170. The lower portion 170 is configured to be placed within the burr hole and the upper flange portion 125 is configured to be disposed on the surface of the skull. The body 110 defines a cavity 145 for receiving a cranial port device. The lower portion 170 defines an opening 140 in communication with the cavity 145. The opening 140 is configured such that a catheter or a catheter connector of the cranial port device may be inserted therethrough. The cavity 145 may be shaped similarly to an outer surface of a housing of the cranial port device.

The upper flange portion 125 defines a top groove 150 that extends from the cavity 145 towards a lateral edge 121 of the top surface 120. The top groove 150 is configured to receive a catheter, such as a catheter coupled to the cranial port device, if any.

The bottom surface 130A of the upper flange portion 125 defines a groove 160A. The device 100 may also comprise a side groove (e.g., 160B as shown in the device of FIGS. 1-4) along the side of the lower portion 170 that meets with the bottom groove 160A. The bottom groove 160A and side groove, if present, may receive a cable comprising a conductor electrically coupled to an electrode disposed on a catheter or a sheath.

The burr hole device 100 of FIGS. 11-14 includes an electrode 180 disposed on the bottom surface 130B of the lower portion 170. The device 100 may include an electrical interconnect 190 comprising a contact 199 for electrically coupling to a lead or other suitable cable to electrically couple the electrode 180 to, for example, signal apparatus. The device 100 includes a conductor 185 that runs through the body 110 of the device 100 and electrically couples the electrode 180 to the contact 199 of the electrical interconnect 190. Alternatively, the burr hole device 100 may comprise a cable (e.g., 195 as shown in FIG. 10) for carrying signals from the electrode 180 to, for example, signal apparatus.

The burr hole device 100 may include one or more through holes 114A-D (four shown) through the upper flange portion 125. The through holes 114A-D may be configured to receive screws for securing the burr hole device 100 to the skull of the subject. While not shown in FIGS. 1-10, it will be understood that the burr hole devices of FIGS. 1-10 may also have through holes.

Figure 11:
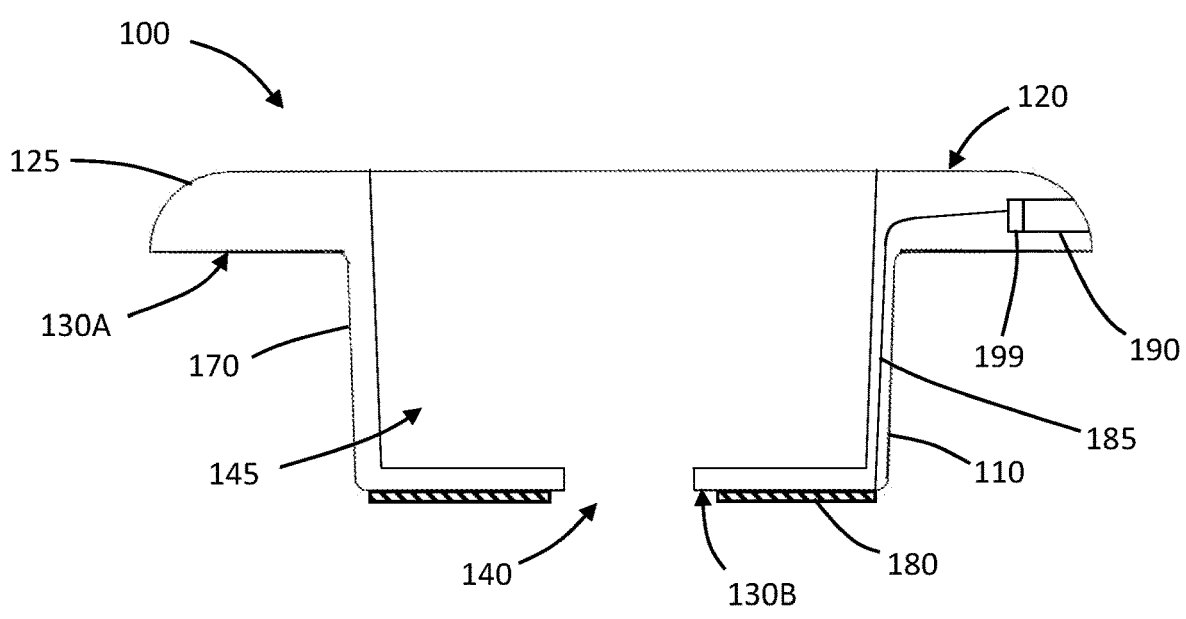
FIG. 11 is a schematic sectional view of an embodiment of a burr hole device configured to receive a cranial port device.
Figure 12:
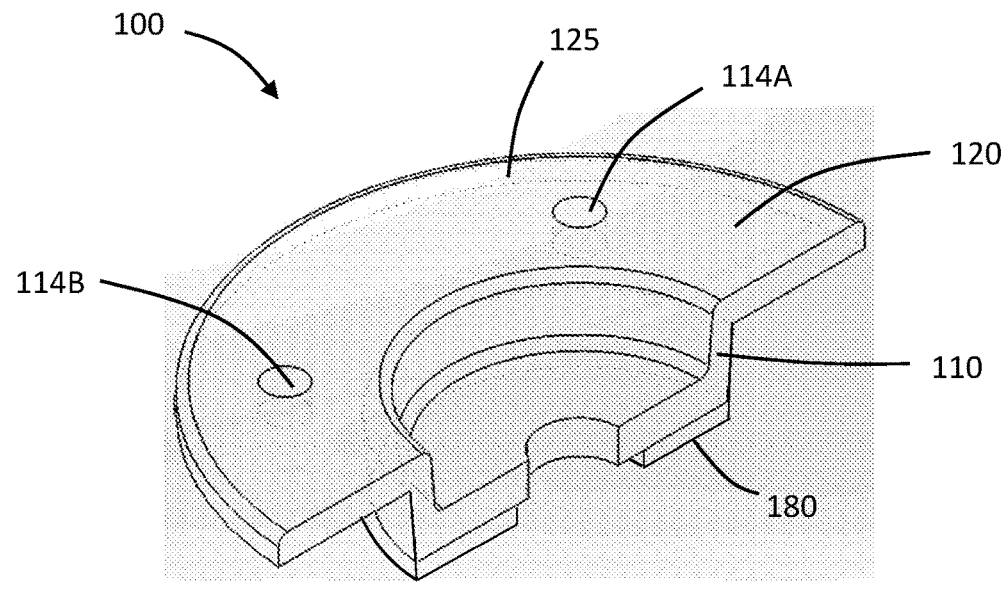
FIG. 12 is a schematic perspective sectional view of the burr hole device of FIG. 11.
Figure 13:
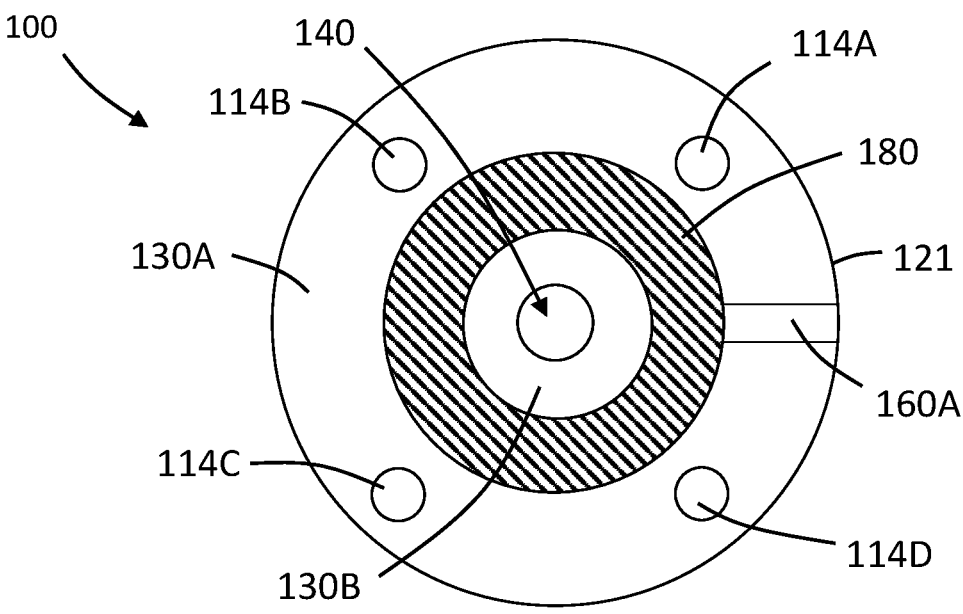
FIG. 13 is a bottom plan view of the burr hole device of FIG. 11.
Figure 14:
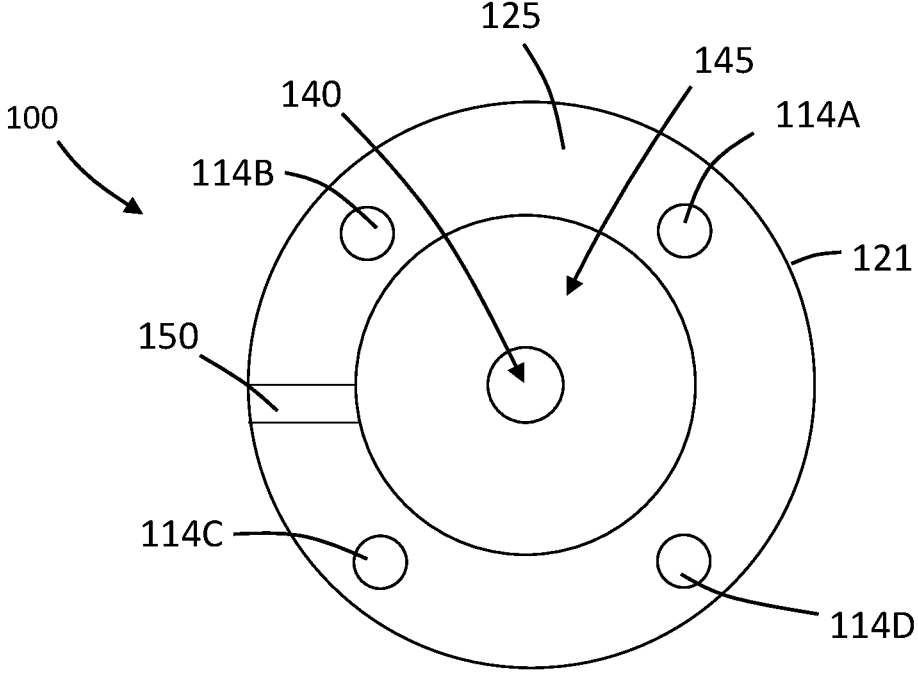
FIG. 14 is a top plan view of the burr hole device of FIG. 11.
Figure 15:
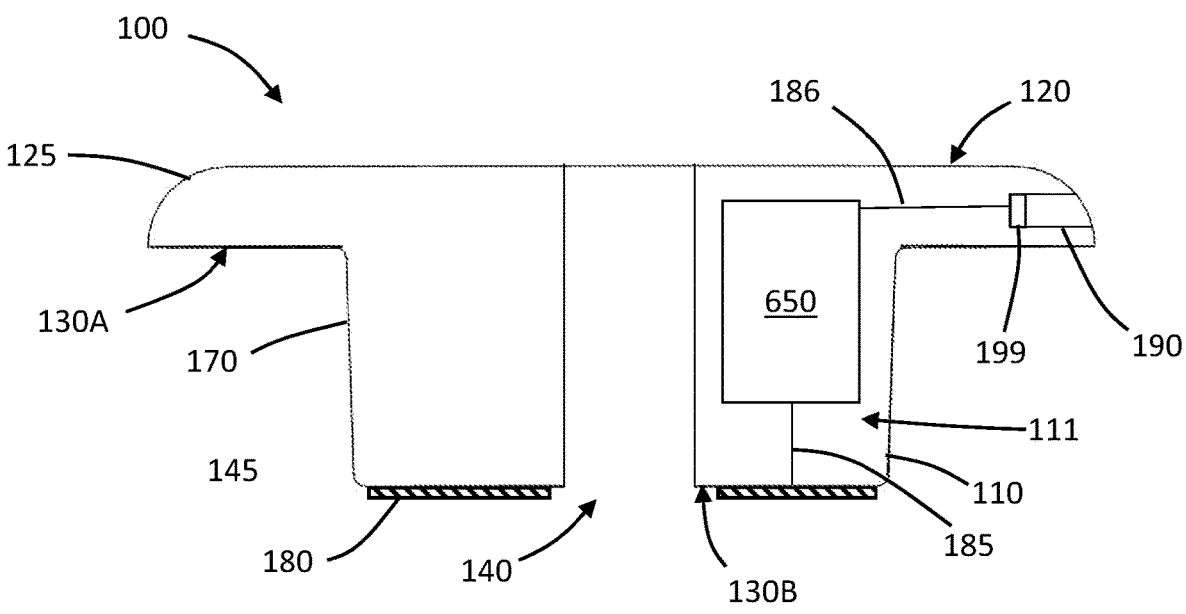
FIG. 15 is a schematic side sectional/block view of a burr hole device comprising electronic components.

The burr hole device 100 of FIG. 15 is similar to the burr hole device of FIG. 11, except that the burr hole device 100 of FIG. 15 includes one or more electronic component 650 operably coupled to the electrode 180 or electrodes via one or more conductors 185. The electrode 180 or electrodes may be positioned at a bottom surface 130B of the lower portion 110 of the burr hole device 100. The one or more electronic components 650 may be housed in a cavity 111 defined by a body of the lower portion 110 of the device. The electronic components 650 may be operatively coupled to electrodes of another device or devices, such as a sheath, a lead, or the like.

The one or more electronic component 650 may one or more of: store, transmit, and process signals from the electrode 180 or electrodes. The one or more electronic component 650 may include one or more of a power source, a transmitter for transmitting brain activity obtained from the electrodes, a controller for controlling other components, a processor, memory for storing brain activity data, which may or may not be processes, and memory containing instructions carried out by the controller or processor. The power supply may comprise a battery. The battery may be rechargeable, wireless powered, or rechargeable and wirelessly powered. The signal apparatus may comprise an inductive coil, solenoid, or other suitable components configured to permit wireless powering or charging by an external apparatus and to transmit data regarding the signals recorded by the electrodes to the external apparatus.

The external device may be placed in proximity to the burr hole device 100 to permit wireless charging, powering, and/or data transfer. Any suitable external device may be used. In embodiments, the external device may be worn by the subject. For example, the external device may comprise a hat having electronic components that may be placed in proximity to the burr hole device 100 when the subject wears the hat. The external device may be continuously placed in proximity to the burr hole device 100 to permit transmission of brain activity data from the one or more electronic components 650 to be transmitted to the external device. The external device may be worn for short periods of time or for long durations. When the external device is not in proximity to the burr hole device the one or more electronic components 650 the one or more electronic components 650 of the burr hole device may store brain activity data. Once the external device is placed in proximity to the burr hole device 100, the one or more electronic components 650 may transmit the stored data to the external device.

The electrical components 650 may optionally be electrically coupled to one or more contact 199 of an electrical interconnect 190 via one or more conductors 186. The electrical interconnect 190 may be used to connect the control electronics 650 to other signal apparatus, which may be implanted.

Referring now to FIGS. 16A-D, an embodiment of a burr hole device 100 configured to be inserted into a burr hole of a subject and to be secured against a side of the burr hole is shown. The depicted burr hole device 100 does not contain an upper flange portion. However, embodiments of burr hole devices having an upper flange portion (e.g., as shown in, and described regarding, FIGS. 1-14) and configured to be inserted into a burr hole of a subject and to be secured against a side of the burr hole are contemplated herein.

The burr hole device in FIGS. 16A-D has a body 111 defining a top surface 120, a bottom surface 130 and a lumen 140 extending through the body 111 from the top surface 120 to the bottom surface 130. The lumen 140 may be configured to receive one or more of a catheter, a cable (such as a cable of a sheath), a lead, or the like. The catheter may be configured to infuse fluid to, or withdraw fluid from, a brain of a subject. The catheter may be a therapeutic fluid delivery catheter, a catheter of a ventriculoperitoneal shunt, a catheter of an external ventricular drain, a catheter for aspirating CSF, or the like.

The body 111 may define a cavity for housing one or more electronic components, such as electronic components 650 as depicted in FIG. 15. The device 100 may comprise an electrode, such as an electrode 180 as depicted in FIG. 15.

Figure 16A:
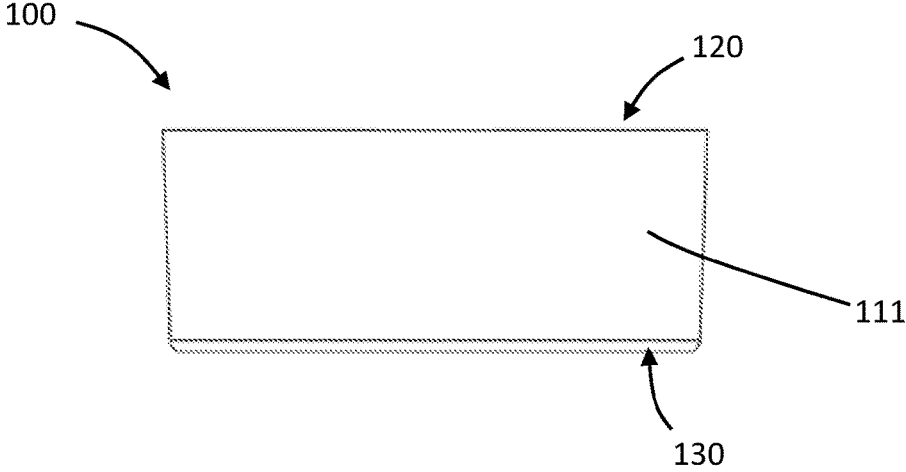
FIGS. 16A-D are side views (A and C), a sectional view (B), and a top view (D) of an embodiment of a burr hole device.
Figure 16B:
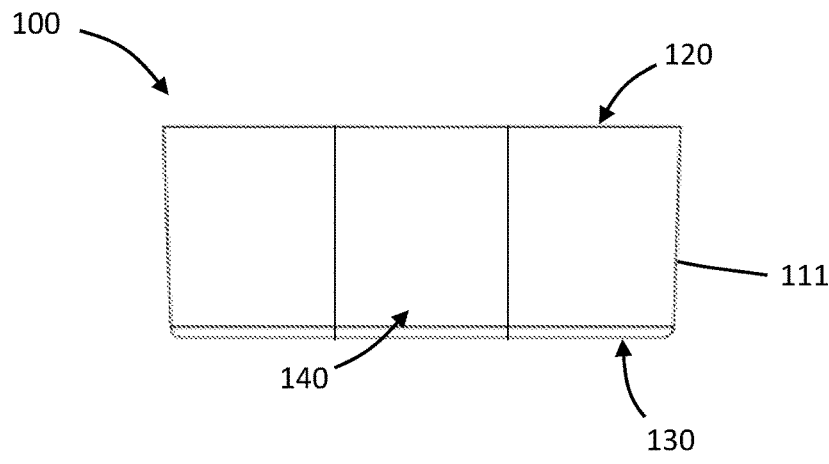
Figure 16C:
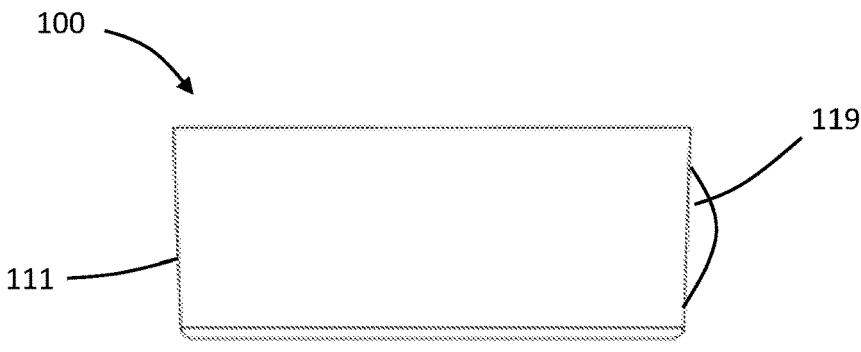
Figure 16D:
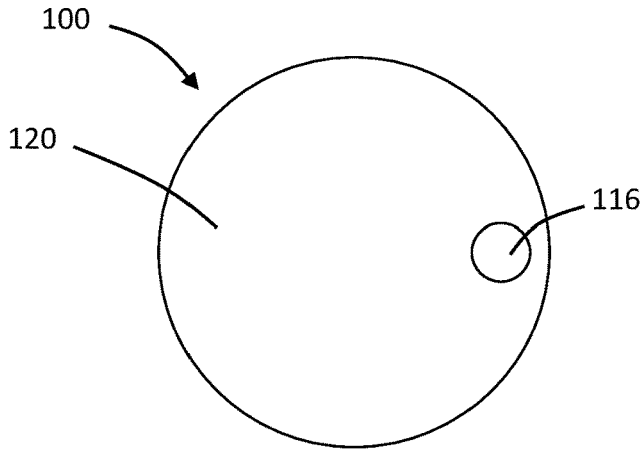

At least a portion of the body 111 of the burr hole device 100 of FIGS. 16A-D is configured to be inserted into a burr hole. In embodiments, the entire device 100 is configured to be received in the burr hole. The burr hole device 100 comprises an expansion member 119 that may be deployed when the body 111 is in the burr hole. The expansion member 119 is configured to expand against a side of the burr hole to anchor the body 111 within the burr hole. The expansion member 119 is deployable from a retracted state (FIG. 16A) to an expanded state (FIG. 16C). When the expansion member 119 is in the retracted state, the body 111 is slidably receivable in the burr hole. The expansion member 119 may be operatively coupled to a user actuatable member 116 that, when actuated, causes the expansion member 119 to adapt the expanded state. The user actuatable member 116 may be a screw, bolt, or the like, that may be turned by a user when using an appropriate tool, such as a screwdriver, or the like.

Any suitable expansion member 119 and user actuatable member 116 or combination thereof may be employed. For example, the user actuatable member 116 may comprise a screw and expansion member 119 may be an anchor that expands as the screw is advanced. The user actuatable member 116 may comprise a bolt and expansion member 119 may comprise an elongate member. The elongate member may be coupled to the bolt such that rotation of the bolt causes rotation of rotation of an elongate member about an axis of the bolt to cause the elongate member press against the side of the burr hole to retain the body 111 in the burr hole.

The body of the burr hole devices described herein may be made from any suitable material or materials. In embodiments, the body of the burr hole device comprises rigid materials such as a hard plastic, ceramic, glass, or metallic material, or a combination thereof. Rigid material may have a higher durometer than more flexible materials. Examples of materials that may be used to form the body of the burr hole device include one or more of a high-performance thermoplastic or relatively rigid plastic material, such as polyurethane, polycarbonate, polysulfone, polyether ether ketone (PEEK), nylon, and Ultra High Molecular Weight Polyethylene (UHMWPE); and a biocompatible metal, such as a stainless steel alloy, titanium, and nitinol. Preferably, the material is compatible with magnetic resonance imaging (MRI). Preferably, the upper flange comprises a biocompatible material or comprises an exterior biocompatible coating.

Figure 17:
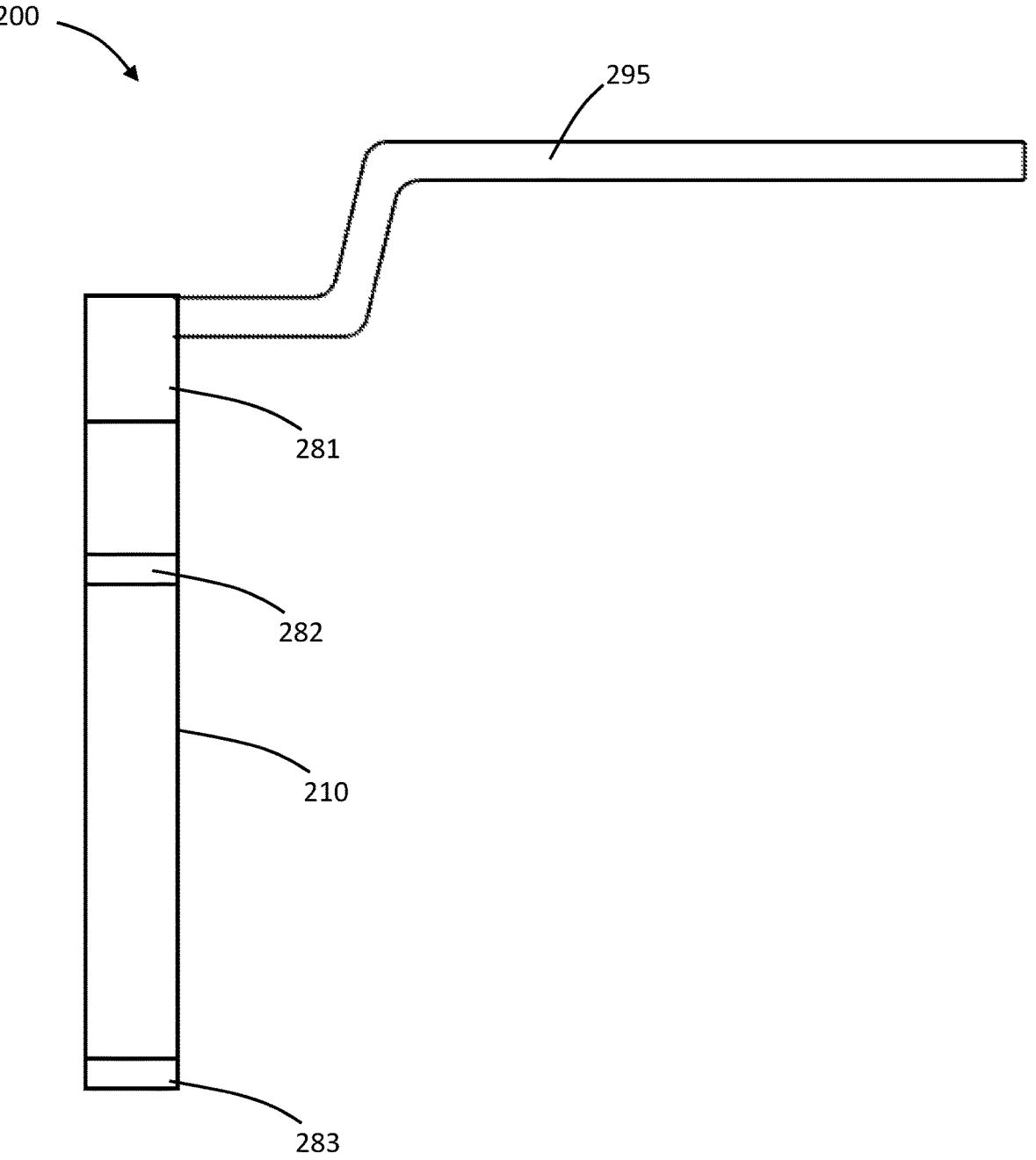
FIG. 17 is a schematic side view of an embodiment of the sheath containing electrodes.
Figure 18:
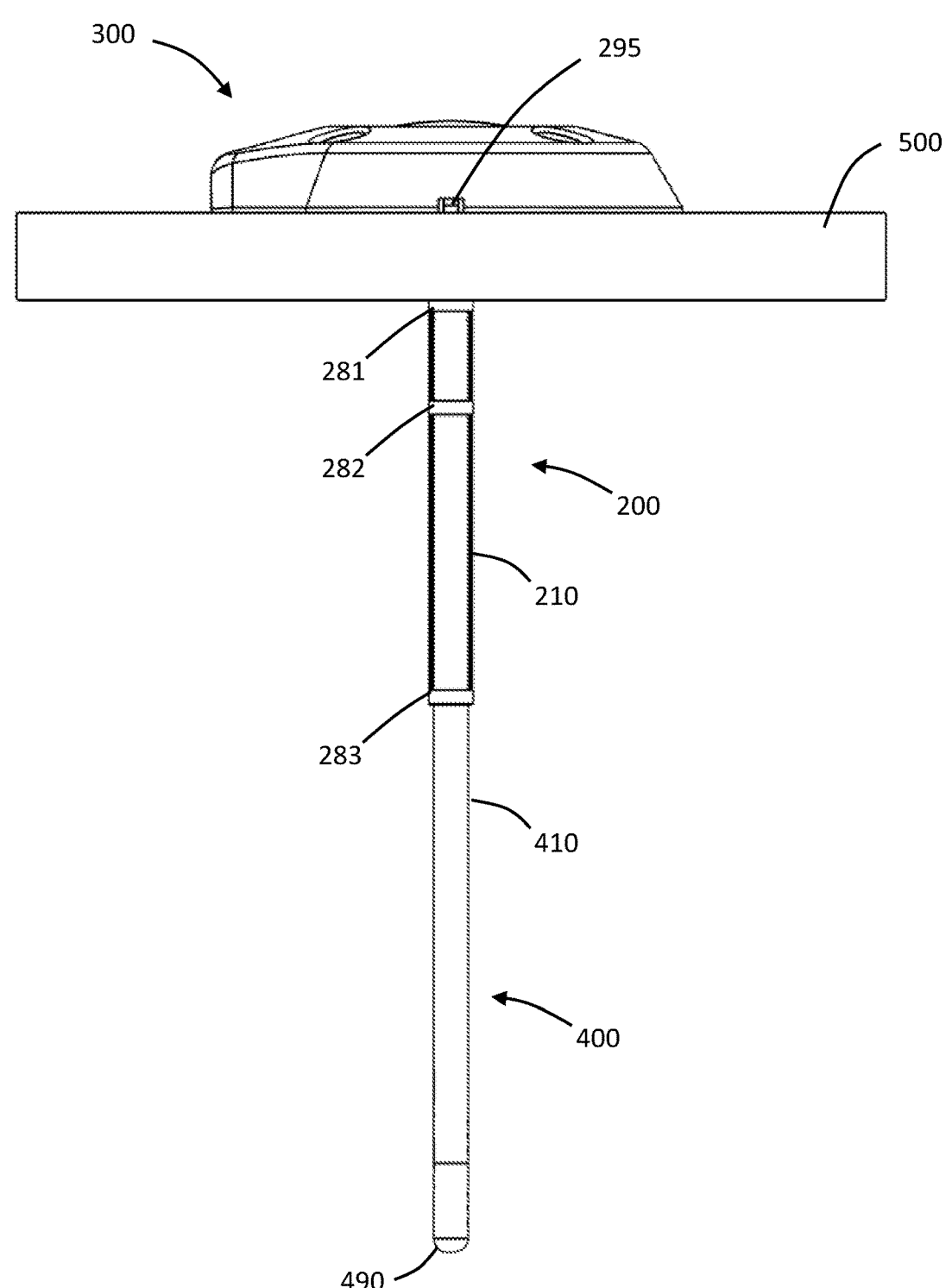
FIG. 18 is a schematic side view of an embodiment of an assembly comprising a cranial port, the sheath of FIG. 17, and a catheter relative to a skull.
Figure 19:
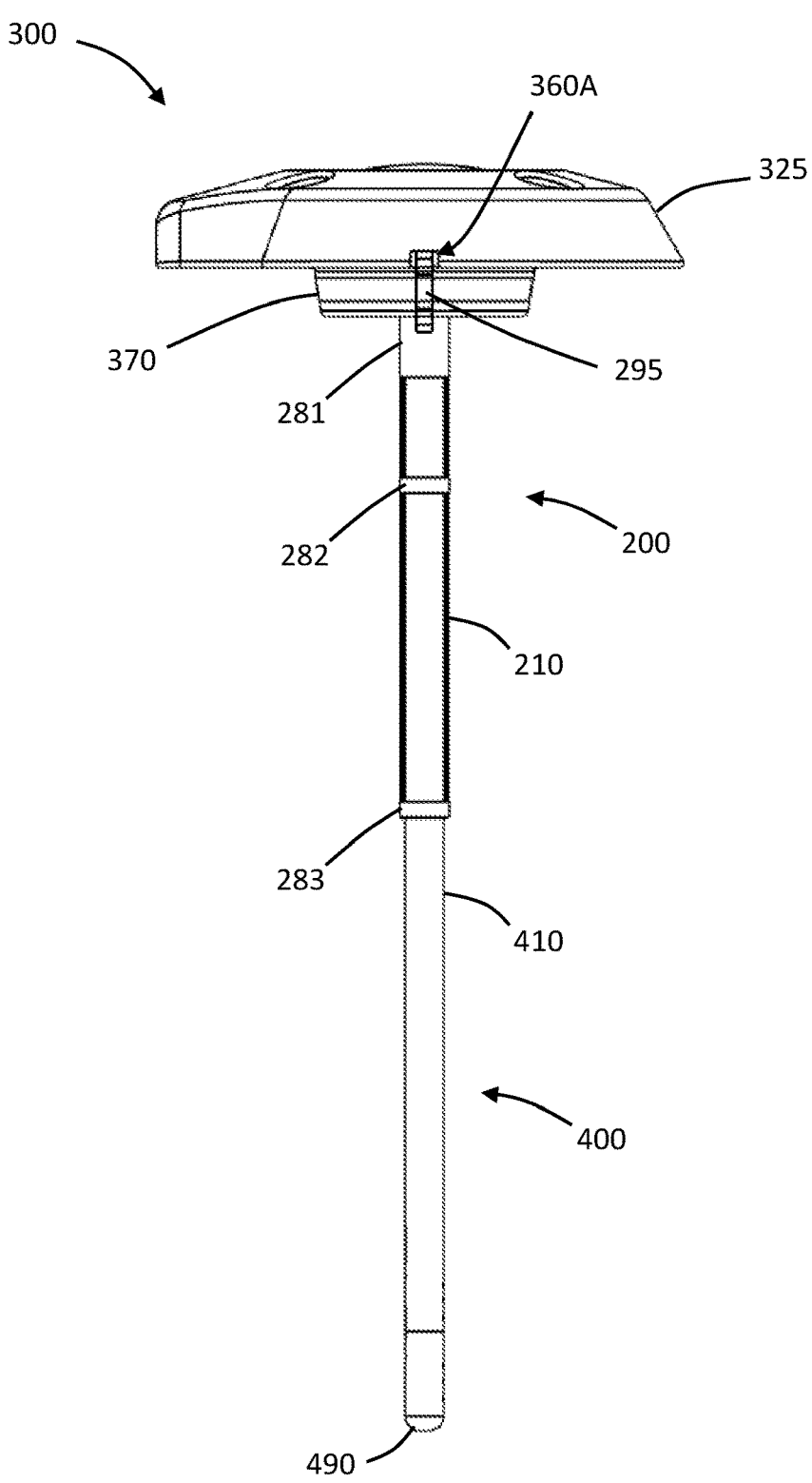
FIG. 19 is a schematic side view of the assembly of FIG. 18 with the skull removed.
Figure 21:
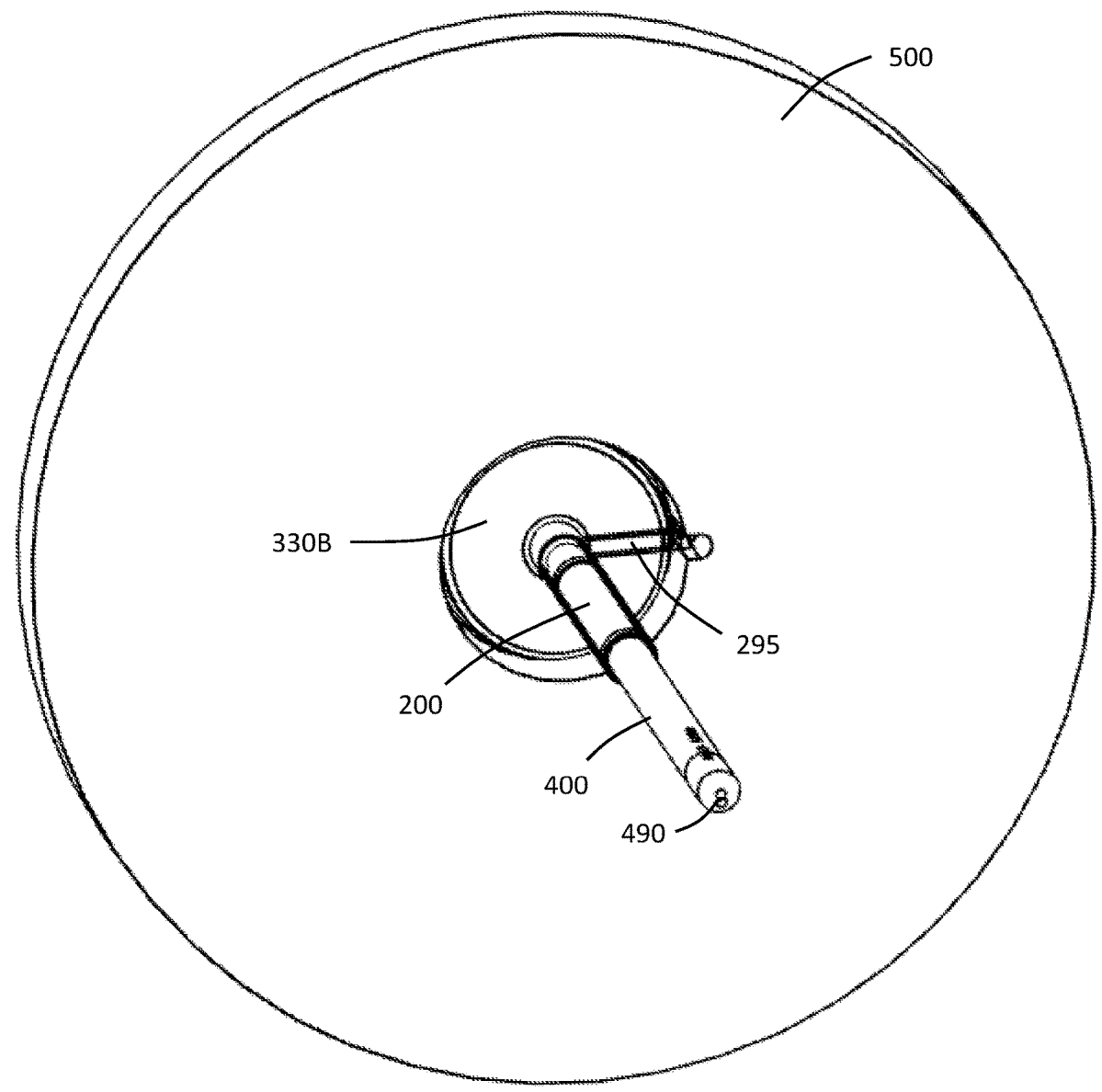
FIG. 21 is a schematic perspective view of the assembly of FIG. 18.
Figure 22:
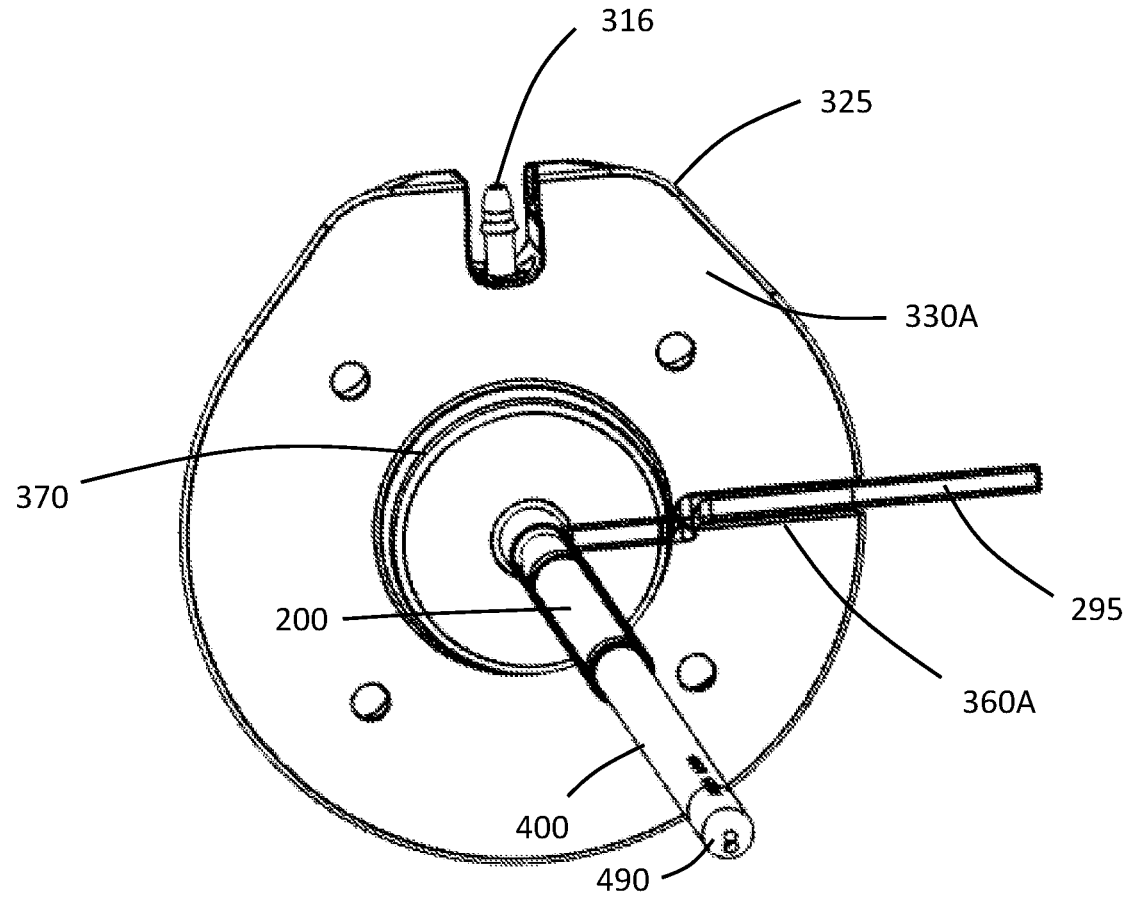
FIG. 22 is a schematic perspective view of the assembly of FIG. 21 with the skull removed.
Figure 23:
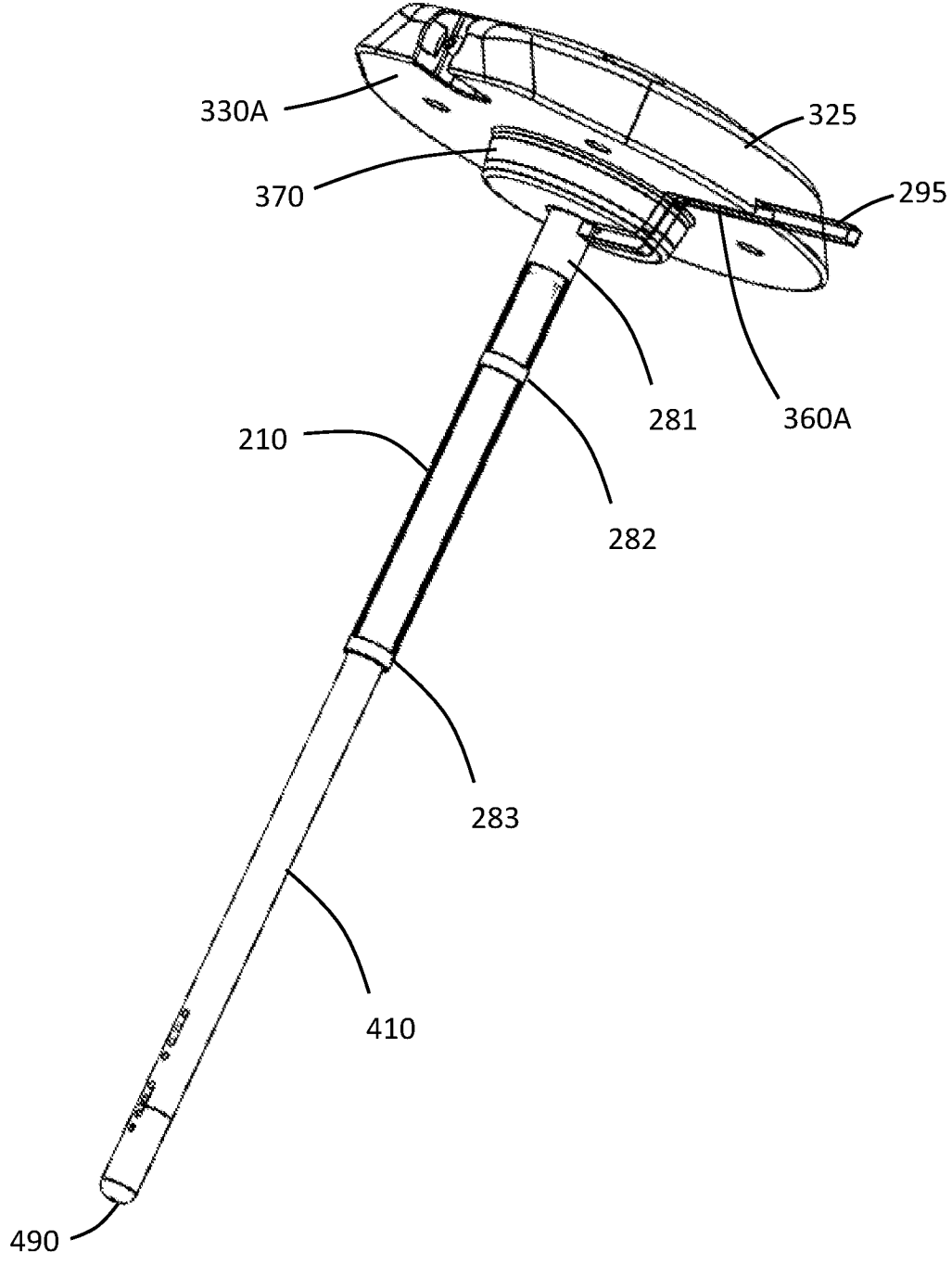
FIG. 23 is a schematic perspective view of the assembly of FIG. 18.

Referring now to FIG. 17, an embodiment of a sheath 200 is shown. The sheath 200 is configured to receive a catheter via a lumen that runs through the length of the body 210 of the sheath 200. The sheath 200 comprises one or more electrodes 281, 282, 283 (three shown) and a cable 295 comprising one or more conductors. Each conductor may be independently electrically coupled to an electrode 281, 282, 283. The cable 295 may comprise contacts (not shown), each independently electrically coupled to a conductor such that the conductors discretely electrically couple the contacts to the electrodes 281, 282, 283.

The sheath 200 is configured to be implanted such that the one or more electrodes 281, 282, 283 are in contact with the brain of a subject. The one or more electrodes 281, 282, 283 may be used to detect brain activity, such as electrocochleogram (EEG) activity. Contacts of the cable 295 or an interconnect electrically coupled with the cable 295 may be used for electrical coupling to signal apparatus.

The sheath 200 may be used with a burr hole device 100 as described herein, such as a burr hole device as shown in FIGS. 1-16 or may be used without a burr hole device as described herein. The cable 295 may be received within a groove of the burr hole device 100, such as in groove 160A, 160B, 160C, or 165, or groove portion 165' shown in FIGS. 1-16. If the burr hole device 100 includes an electrode 180, the electrode 180 of the burr hole device 100 and the one or more electrodes 281, 282, 283 of the sheath 200 may be operatively coupled to signal apparatus so that the signals detected by the electrode 180 of the burr hole device 100 and the one or more electrodes 281, 282, 283 of the sheath 200 may be appropriately processed or transmitted.

The diameter of the lumen defined by the sheath body 210 is preferably no more than 1 mm greater than the outer diameter of the catheter to keep minimal the outer diameter of the sheath body 210. In embodiments, the diameter of the lumen is no more than 0.9 mm, no more than 0.8 mm, no more than 0.7 mm, no more than 0.6 mm greater, no more than 0.5 mm greater, no more than 0.4 mm greater, no more than 0.3 mm greater, no more than 0.2 mm greater, or no more than 0.1 mm greater than the outer diameter of the catheter. The diameter of the lumen may be substantially the same (e.g., within 10%) along the length of the sheath body 210 or may vary along the length of the sheath body 210.

In embodiments, the diameter of the lumen of the sheath body 210 is from about 2 mm to about 5 mm, such as from about 2.2 mm to about 4 mm, or from about 2.5 mm to about 3.5 mm.

The material of the sheath body 210 defining the lumen and the material defining an outer surface of the catheter preferably have a low coefficient of friction to allow the catheter to easily slide through the lumen. Preferably, the lumen of the sheath body 210 comprises a smooth surface. The surface of the sheath body 210 that defines the lumen may be lubricious or a lubricious coating may be applied to the surface of the lumen.

The sheath body 210 preferably is preferably sufficiently rigid to permit the sheath body 210 to be advanced through brain parenchymal tissue. The sheath body 210 is preferably sufficiently flexible to permit movement along with movement of the brain so that the sheath body 210 does not damage brain tissue when implanted.

One of skill in the art will understand that the rigidity and flexibility of the sheath body 210 will depend on the material from which the elongate body is formed as well as the thickness of the sheath body 210. The sheath body 210 may have any suitable thickness from an outer surface to the lumen. In embodiments, the sheath body 210 has a thickness from about 0.1 mm to about 1 mm, such as from about 0.2 mm to about 0.5 mm.

The sheath body 210 may be formed from any suitable material. For example, the elongate body may be formed from polydimethylsiloxane (PDMS).

The electrodes 281, 282, 283 of the sheath 200 may be positioned on the sheath body 210 in any suitable manner. For example, the electrodes 281, 282, 283 may extend around the circumference of the sheath body 210 or may extend less than all the way around the circumference of the sheath body 210. For example, the electrodes 281, 282, 283 may radially extend around the sheath body 210 from about 10 degrees to about 360 degrees, such as from about 10 degrees to about 20 degrees, from about 150 degrees to about 210 degrees, or about 180 degrees. Each electrode 281, 282, 283 may extend around the sheath body 210 the same or a different amount. Preferably, each electrode 281, 282, 283 extends around the sheath body 210 the same amount. Preferably, each electrode 281, 282, 283 extends radially around the sheath body 210 about 180 degrees, or about half-way around the circumference of the sheath body 210, to all the way around the circumference of the sheath body 210, or about 360 degrees.

The electrodes 281, 282, 283 may be made of any suitable material. Suitable materials for implantable electrodes are well-known to those of skill in the art. Materials suitable for deep brain stimulation electrodes are suitable materials for electrodes of the catheters described herein. In embodiments, the electrodes are made from platinum or a platinum iridium alloy.

The electrodes 281, 282, 283 may have any suitable thickness. For example, the electrodes 281, 282, 283 may have a thickness from about 100 microns to about 3 millimeters, such as from about 200 microns to about 2 millimeters. The electrodes 281, 282, 283 may be formed from a foil.

Each electrode 281, 282, 283 may be discretely electrically coupled to one or more electrical contacts. Each electrode may be electrically coupled to a discrete contact by an electrical conductor, such as a wire. The conductors may extend within the sheath body 210 and may branch off from the sheath body 210 in proximity to the proximal end of the sheath body 210. The conductors may comprise an electrically insulating coating or outer surface. Conductors that branch off the sheath body 210 may be braided or twisted to form a cable 295. The cable may comprise an electrically insulating outer material.

In embodiments, an assembly comprises the sheath 200, and a catheter. In embodiments, an assembly comprises the sheath 200, the burr hole device 100, and a catheter. In embodiments, an assembly comprises the sheath 200, the burr hole device 100, a catheter, and a cranial port device. In embodiments, an assembly comprises the sheath 200, a catheter, and a cranial port device. The catheter may be a therapeutic fluid delivery catheter, a catheter of a ventriculoperitoneal (VP) shunt, a catheter of an external ventricular drain (EVD), a catheter for aspirating CSF, or the like. The assembly may comprise a VP shunt, an EVD, an infusion device, which may be an implantable infusion device, configured to connect to the therapeutic fluid delivery catheter, or the like.

Referring now to FIGS. 18-26, assemblies including a sheath 200, a cranial port device 300, and a catheter 400 are shown. The assembly of FIGS. 18-24 includes the sheath 200 of FIG. 17. The assemblies of FIGS. 18-26 include a cranial port device 300 having two fluid pathways, and a dual lumen catheter 400. However, the assemblies described herein may comprise any suitable cranial port device having any suitable number of fluid pathways, such as one or two pathways, and any suitable catheter having any suitable number of lumens, such as one or two.

The cranial port device 300 depicted in the assemblies of FIGS. 18-26 may be a cranial port device as described in U.S. 2022/016338-A1, entitled IMPLANTABLE CRANIAL MEDICAL DEVICE, filed on Jul. 15, 2021, and published on Jan. 20, 2022, or a modified version thereof.

The depicted cranial port device 300 comprises a body defining an upper flange portion 325 and a lower portion 370. The lower portion 370 is configured to be received by a burr hole in the skull 500 of the subject. The upper flange portion 325 is configured to rest on the skull 500 adjacent to the burr hole. Preferably, the lower portion 370 of the cranial port device 300 has a clearance of 1 millimeter or less when disposed in the burr hole to help stabilize the device 300 when implanted. In embodiments, the lower portion 370 of the cranial port device 300 has an outer diametric dimension in a range from 10 millimeters to 20 millimeters, which outer diametric dimension may depend on the size of the burr hole. In embodiments, the lower portion 370 of the cranial port device 300 has an outer diametric dimension in a range from 10 millimeters to 20 millimeters. In embodiments, the lower portion 370 of the cranial port device 300 has an outer diametric dimension in a range from 10 millimeters to 14 millimeters, such as from about 11 millimeters to about 13 millimeters. Typically, the outer surface of the lower portion 370 is generally cylindrical as depicted in FIGS. 18-26 or frustoconical.

When the cranial port device 300 is implanted, a bottom surface 330B of the lower portion 370 of the device 300 preferably does not extend substantially beyond the bottom of skull when received in the burr hole. More preferably, the bottom surface 330B of the lower portion 370 of the device 300 preferably does not extend substantially beyond the bottom of skull. Accordingly, the height of lower portion 370 may vary depending on the thickness of the skull of the subject into which the cranial port device 300 is implanted. As an example, a thickness of a human adult skull may typically be in a range from about 6.5 millimeters to about 7 millimeters.

In some embodiments, the height of the lower portion 370 of the cranial port device 300 (distance from the bottom surface 330A of the upper flange portion 325 to the bottom surface 330B of the lower portion 370) is in a range from about 3 millimeters to about 7 millimeters. For example, the height of the lower portion 370 may be in a range from about 4 millimeters to about 6 millimeters or from about 4.5 millimeters to about 5.5 millimeters.

The upper flange portion 325 is configured to be disposed on the surface of the skull adjacent to the burr hole. That is, the bottom surface 330A of the upper flange portion 325 may rest on the skull when the device 300 is implanted. The upper flange portion 325 has an outer diametric dimension that is greater than the diameter of the burr hole. In embodiments, the outer diametric dimension of the upper flange portion 370 is in a range from 15 millimeters to 30 millimeters.

The bottom surface 330A of the upper flange portion 325 defines a bottom groove 360A configured to receive a cable 295 of the sheath 200. The bottom groove 360A extends from a lateral edge 121 of the bottom surface 330A towards the bottom surface 330A abutting the lower portion 370. The cable 295 may be protected by the bottom groove 360A when implanted, rather than being pinched between the upper surface of the skull and the bottom surface 330A of the upper flange portion 325 of the cranial port device 300.

While not shown, the lower portion 370 of the device 300 may define a side groove that may run the length of the lower portion 370. The side grove may intersect with and meet the bottom groove 160A. The side groove may be configured to receive the cable 295 such that the cable. The cable may be positioned in the side groove between the side of the burr hole and the body of the lower portion 370 when the cranial port device 300 is implanted. When clearances are small between the lower portion 370 and the burr hole, the cable 295 may be protected in the side groove, as opposed to being pinched between the lower portion 370 of the device 300 and the side of the burr hole. The cranial port device 300 may optionally comprise bottom groove on the bottom surface 330B of the lower portion 370 of the cranial port device 300. The bottom groove may intersect and meet with side groove.

The cranial port device 300 includes two fluid flow pathways. The first pathway runs from a opening in the upper flange portion 325 (shown with self-sealing septum 312 disposed across the opening) to a first lumen in a brain catheter connector 322 extending from the bottom of the lower portion 370. The first pathway may be used to withdraw fluid from the brain of the subject, or to inject fluid into the brain of the subject, through the catheter 200. The second fluid pathway extends from a lumen of an infusion catheter connector 316 to a second lumen in the brain catheter connector 322. The second pathway may be used to infuse fluid into the brain of the subject when connected to the catheter 200. An infusion catheter may be coupled to the infusion catheter connector 316 on one end and may be coupled to an infusion device, such an implantable infusion device, on the other end.

When coupled to the brain catheter connector 322, a first lumen 420A of the catheter 400 is fluidly coupled to the first fluid pathway of the cranial port device 300 and a second lumen 420A of the catheter 400 is fluidly coupled to the second fluid pathway of the cranial port device 300. Openings 450 are defined in the catheter body 410. Each opening 450 is in fluid communication with either the first 420A or second 420B lumens of the catheter 400 to allow fluid to flow into the brain from the catheter 400 or to flow into the catheter 400 from the brain when the catheter 400 is implanted and coupled to the cranial port device 300.

In embodiments, the distal end 490 of the catheter 400 is positioned in a CSF-containing space of the brain when implanted. Preferably, the distal end 490 of the catheter 400 is positioned in a lateral ventricle.

The catheter 200 may be a catheter as described in U.S. 2022/016338-A1, entitled IMPLANTABLE CRANIAL MEDICAL DEVICE, filed on Jul. 15, 2021, and published on Jan. 20, 2022, or any other suitable catheter.

A proximal portion of the catheter 400 is received in lumen defined by the sheath body 210. The sheath body 210 and catheter 400 are configured to be intracranially implanted beneath the skull 500 of a subject. When implanted, one or more electrodes 281, 282, 283 of the sheath 200 are preferably in contact with parenchymal tissue of the brain.

Figure 24:
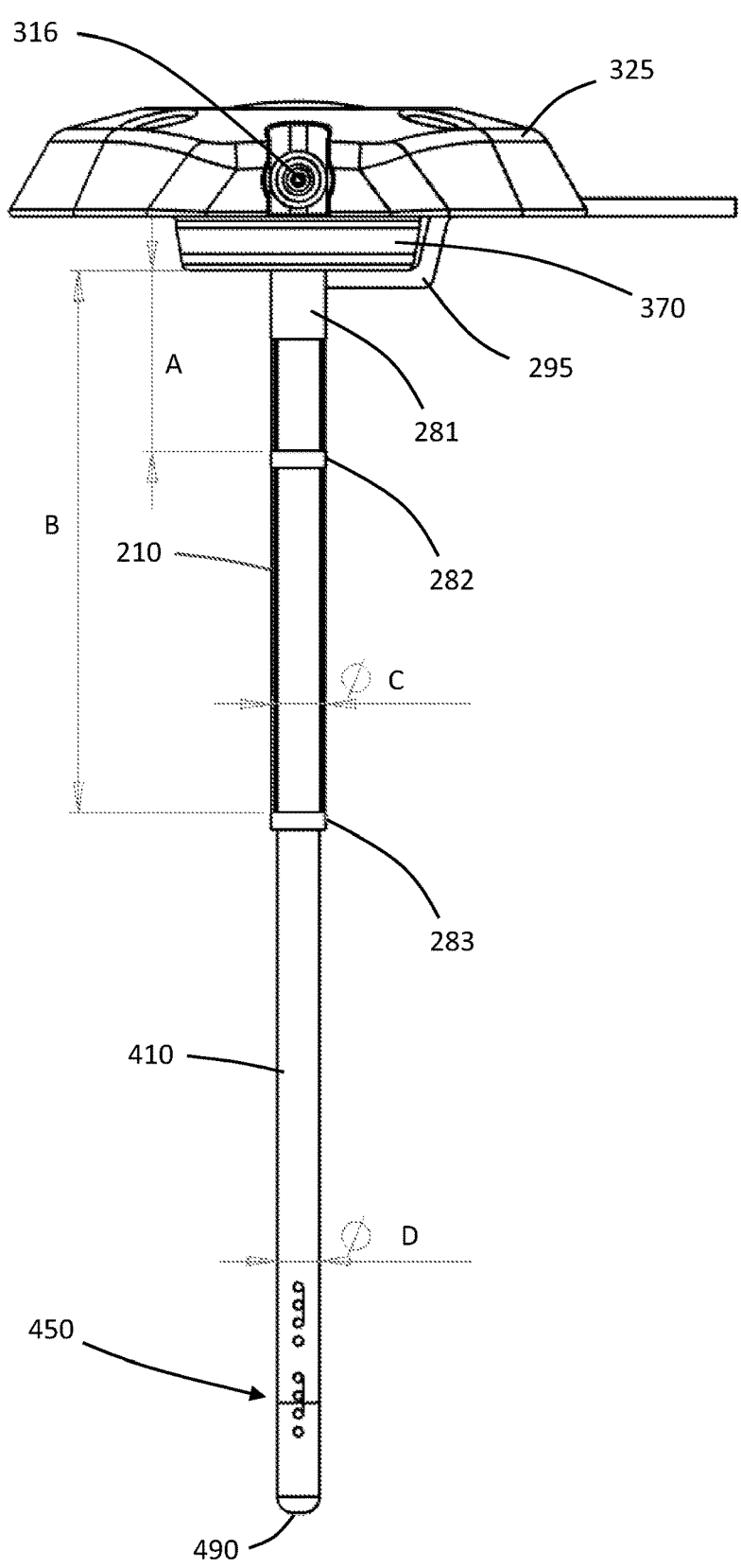
FIG. 24 is a schematic side view of the assembly of FIG. 18.

With reference to FIG. 24, the distance A from the bottom of the lower portion 370 of the cranial port device to the top of electrode 282 of the sheath in the assembly is preferably sufficient to cause the electrode 282 to be implanted in the brain when the assembly is implanted. In embodiments, the distance A is in a range from 5 millimeters to 15 millimeters, such as 8 millimeters to 12 millimeters, or about 10 millimeters.

The distance B from the bottom of the lower portion 370 of the cranial port device to the top of electrode 283 of the sheath in the assembly is preferably sufficient to cause the electrode 283 to be implanted in the brain when the assembly is implanted. In embodiments, the distance B is in a range from 25 millimeters to 35 millimeters, such as 28 millimeters to 32 millimeters, or about 30 millimeters.

The outer diameter C of the sheath is preferably small to minimize damage to the brain when implanted and is not substantially larger than the outer diameter D of the catheter. In embodiments, the outer diameter C of the sheath is in a range from 2 millimeters to 4 millimeters, such as 2.5 millimeters to 3.5 millimeters, or about 3 millimeters. In embodiments, the outer diameter D of the catheter is in a range from 1.75 millimeters to 3 millimeters, such as 2 millimeters to 2.5 millimeters, or about 2.5 millimeters or about 2.33 millimeters.

Figure 25:
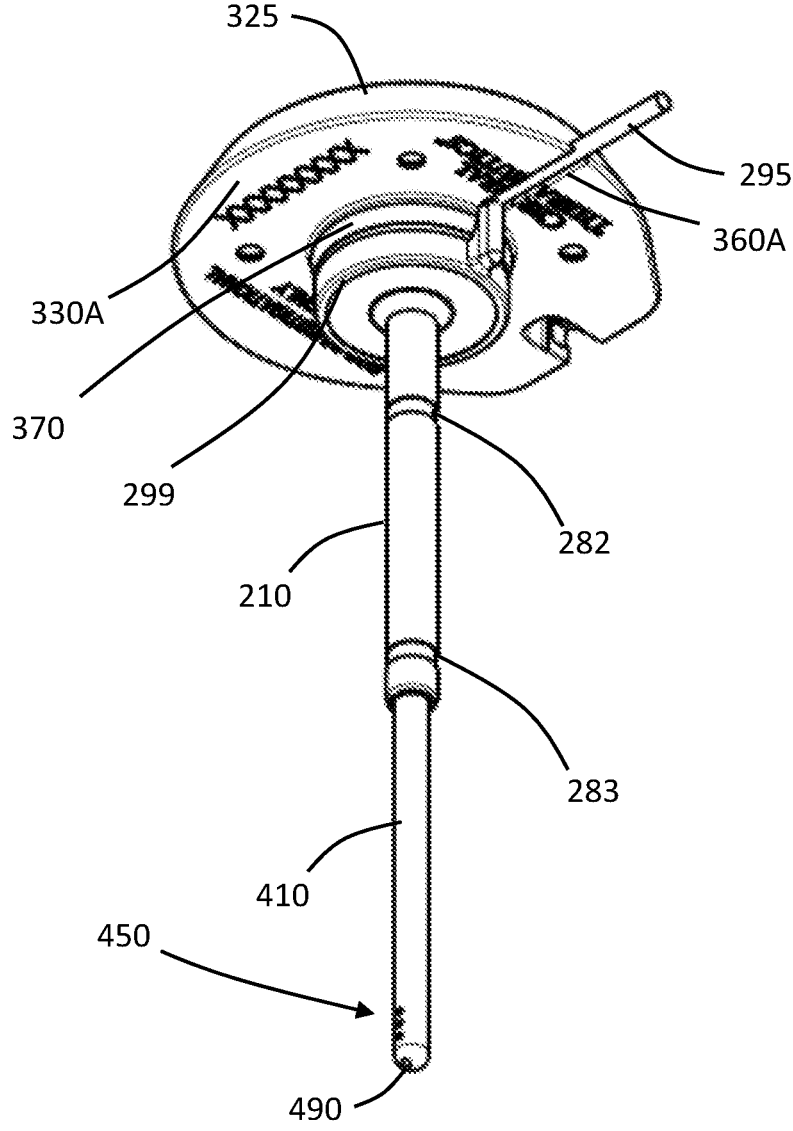
FIG. 25 is a schematic perspective view of an embodiment of an assembly comprising a cranial port device, a sheath, and a catheter.
Figure 26:
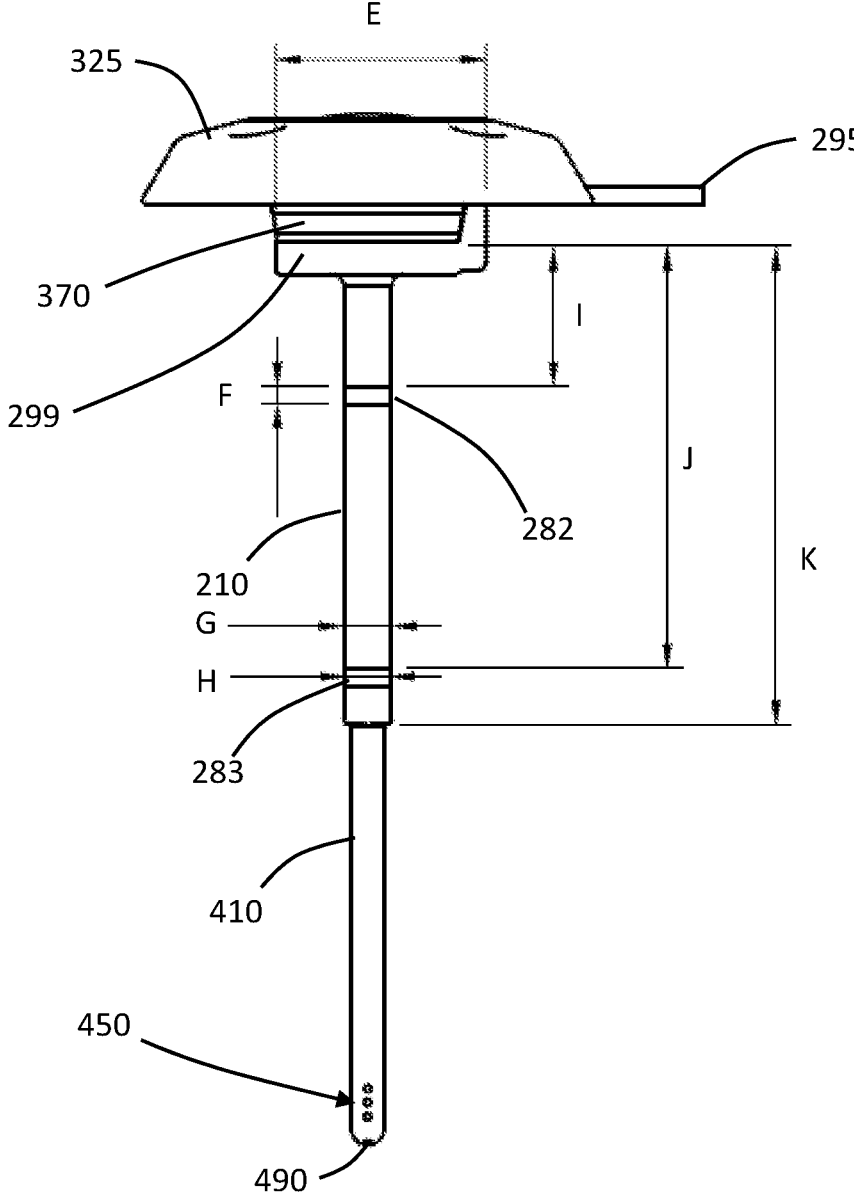
FIG. 26 is a schematic side view of the assembly of FIG. 25.

In FIGS. 25 and 26, the sheath 200 comprises an annular place 299 at the proximal end of the sheath body 210. The cable 295 extends away from the annular plate 299. The annular plate 299 abuts the bottom surface of the lower portion 370 of the cranial port device 300 when implanted.

With reference to FIG. 26, the width or diametric dimension E of the annular plate 299 and portion of cable 295 positioned below the lower portion 370 of the cranial port device in the assembly is preferably sufficiently small to fit within a burr hole when implanted. In embodiments, the width E is in a range from 14 millimeters to 15 millimeters, such as from 14.5 millimeters to 14.95 millimeters, or about 14.9 millimeters or about 14.89 millimeters.

The electrodes 282, 283 may have any suitable height. In embodiments, the height F of electrode 282 is in a range from 0.5 millimeters to 2 millimeters, such as from 0.8 millimeters to 1.6 millimeters, or about 1.2 millimeters.

The outer diameter G of the sheath is preferably small to minimize damage to the brain when implanted and is not substantially larger than the outer diameter of the catheter body 410. In embodiments, the outer diameter G of the sheath is in a range from 2 millimeters to 4 millimeters, such as 2.5 millimeters to 3.8 millimeters, or about 3.4 millimeters.

In embodiments, the outer diameter F of the electrode 283 disposed on the sheath body 210 is less than the outer diameter of the sheath body 210. In embodiments, the outer diameter F of the electrode 283 is in a range from 2 millimeters to 4 millimeters, such as 2.5 millimeters to 3.5 millimeters, or about 3 millimeters or about 3.2 millimeters.

The distance I from the bottom of the lower portion 370 of the cranial port device to the top of electrode 282 of the sheath in the assembly is preferably sufficient to cause the electrode 282 to be implanted in the brain when the assembly is implanted. In embodiments, the distance A is in a range from 5 millimeters to 15 millimeters, such as 8 millimeters to 12 millimeters, or about 10 millimeters.

The distance J from the bottom of the lower portion 370 of the cranial port device to the top of electrode 283 of the sheath in the assembly is preferably sufficient to cause the electrode 283 to be implanted in the brain when the assembly is implanted. In embodiments, the distance B is in a range from 25 millimeters to 35 millimeters, such as 28 millimeters to 32 millimeters, or about 30 millimeters.

The distance K from the bottom of the lower portion 370 of the cranial port device to the distal end of the sheath body 210 in the assembly is shorter than the length of the catheter. In embodiments, the distance K is in a range from 30 millimeters to 40 millimeters, such as 32 millimeters to 36 millimeters, or about 34 millimeters.

Figure 27:
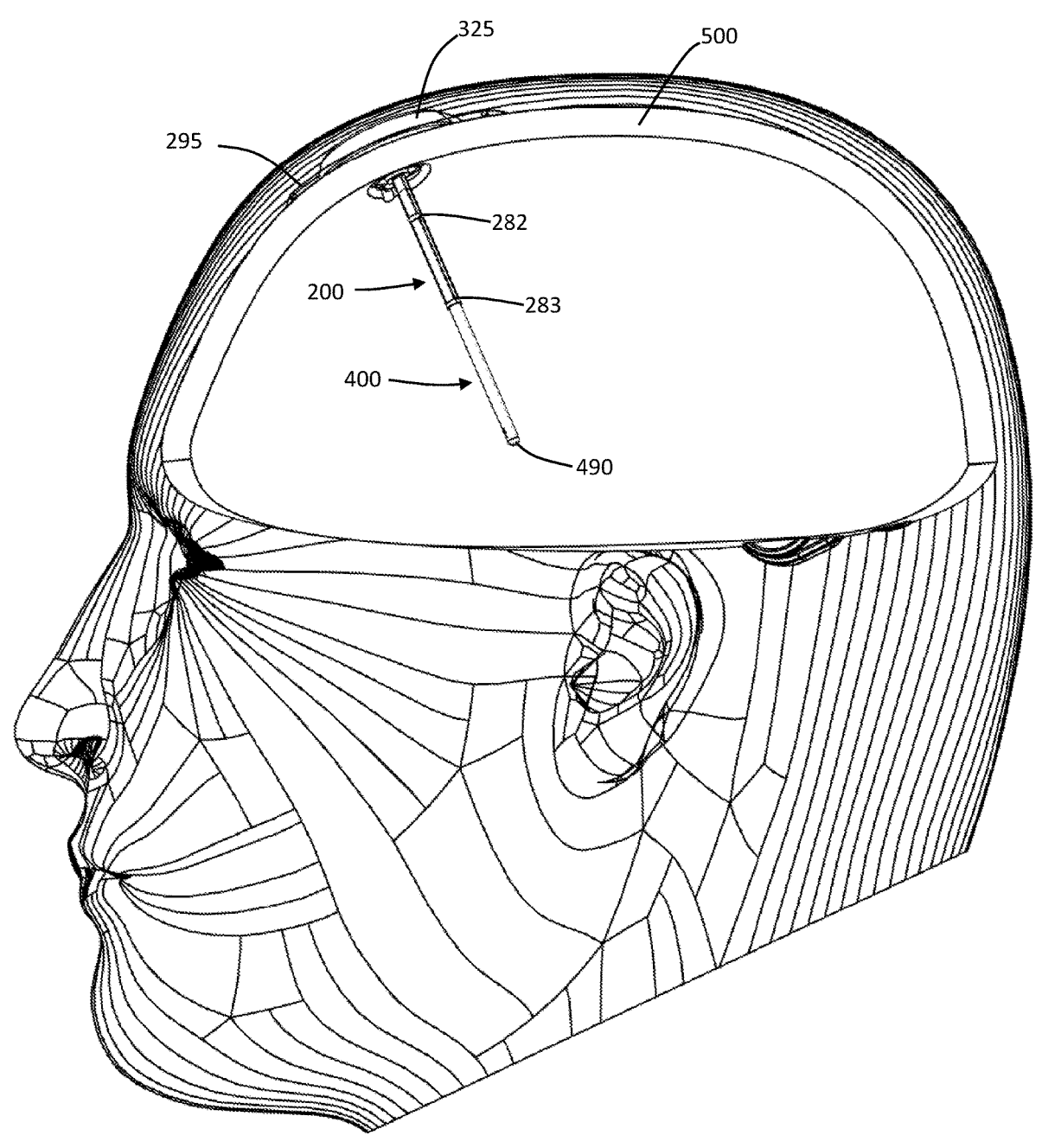
FIG. 27 is a schematic view of an assembly comprising a cranial port device, a sheath, and a catheter implanted relative to a head of a subject.
Figure 28:
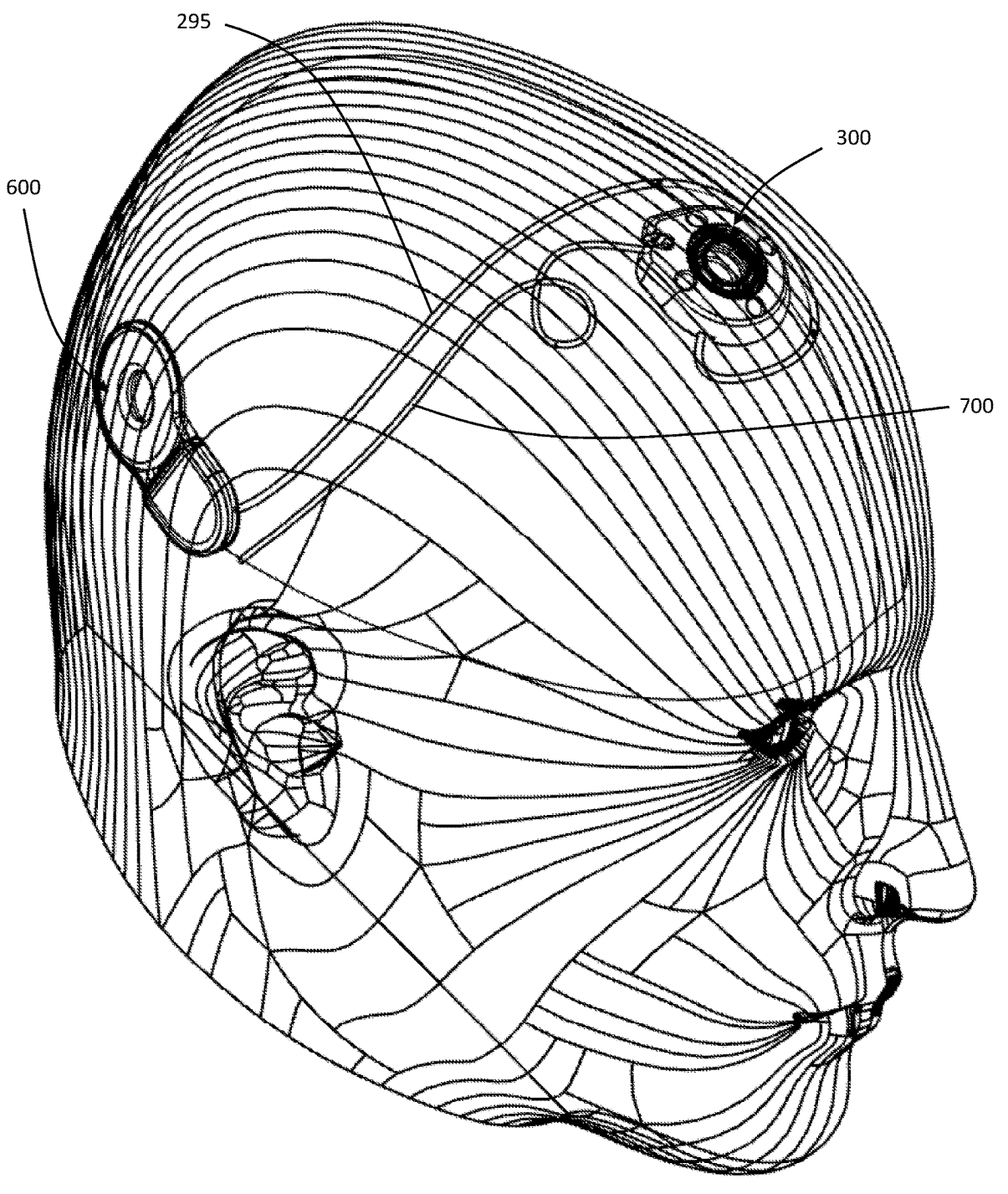
FIG. 28 is a schematic view of a system comprising the assembly of FIG. 27 and signal apparatus implanted relative to the head of the subject.

Referring now to FIGS. 27 and 28, a system comprising a cranial port device 300, a sheath 200, a catheter 400, and signal apparatus 600 are shown implanted in a subject. Components of the system shown in FIGS. 27 and 28 may be similar to the assemblies described regarding FIGS. 18-26. The systems shown in FIGS. 27 and 28 may have some of or all the features or elements of the assemblies FIGS. 18-26. While not shown, the system may also comprise a burr hole device as described herein, or a burr hole device may be substituted for the cranial port device.

As illustrated, the catheter 400 is received within the sheath 200 and operably coupled to the cranial port device 300. Electrodes 282, 283 and the distal end 490 the catheter 400 are positioned in the brain of the subject. The upper flange portion 325 of the cranial port device 300 is positioned on the skull 500 of the subject. The cable 295 of the sheath 200 exits a bottom groove of the upper flange portion 325, extends along the surface of the skull 500 and is operatively coupled to signal apparatus 600. The signal apparatus 600 is shown implanted between the scalp and the skull 500 behind the ear of the subject but may be implanted in any other suitable location. The signal apparatus 600 may be configured to one or more of store, process, and transmit brain activity data received by electrodes 282, 283, etc. Signal apparatus 600 may be configured to transmit data to a device outside of the patient.

An infusion catheter 700 is coupled to the infusion catheter port of the cranial port device 300 and extends across the surface of the skull and subcutaneously to an implantable infusion device (not shown).

Figure 29:
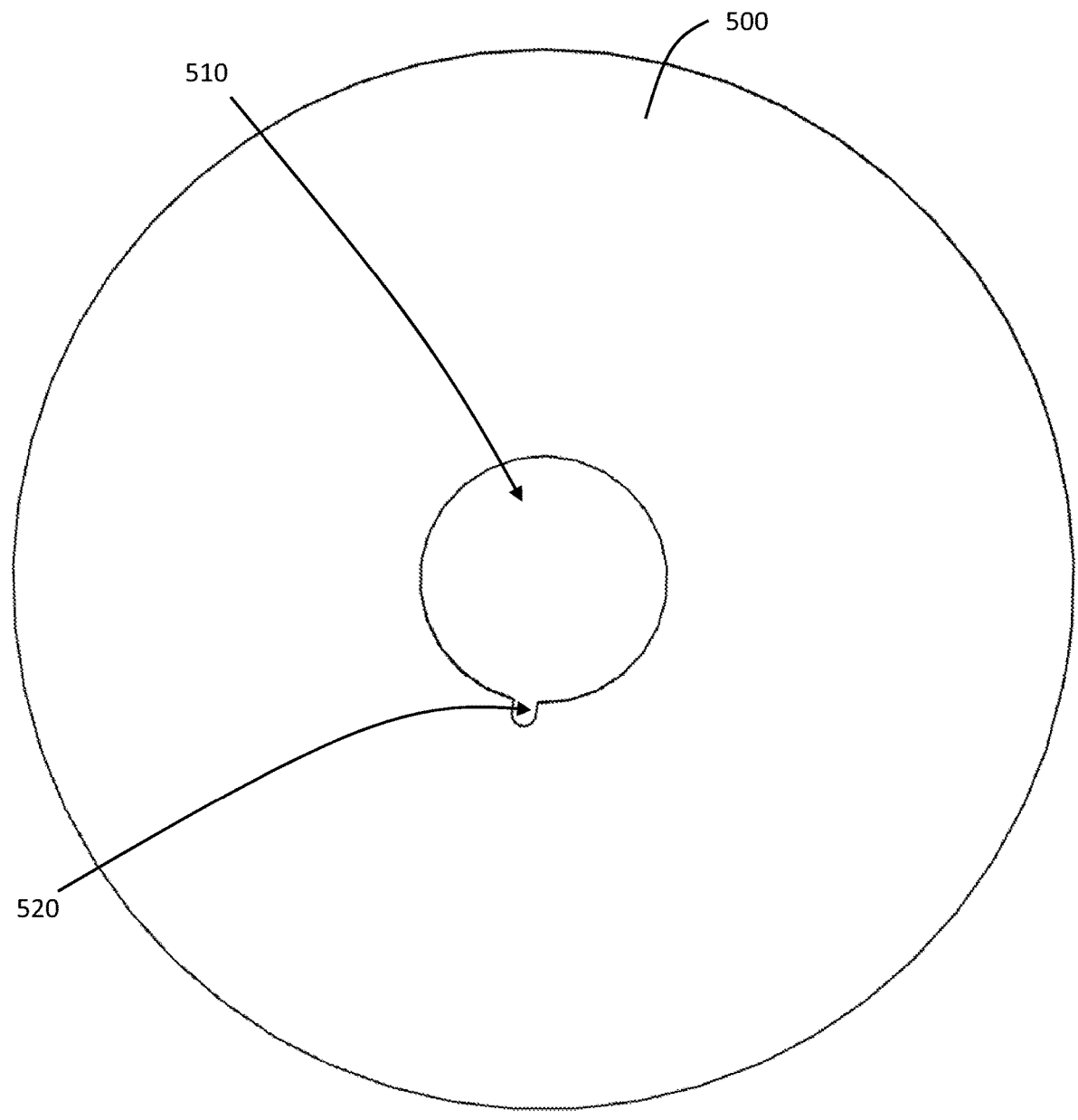
FIGS. 29 and 30 are schematic top view portions of skulls having first and second burr holes therethrough where the burr holes are created according to methods described herein.
Figure 30:
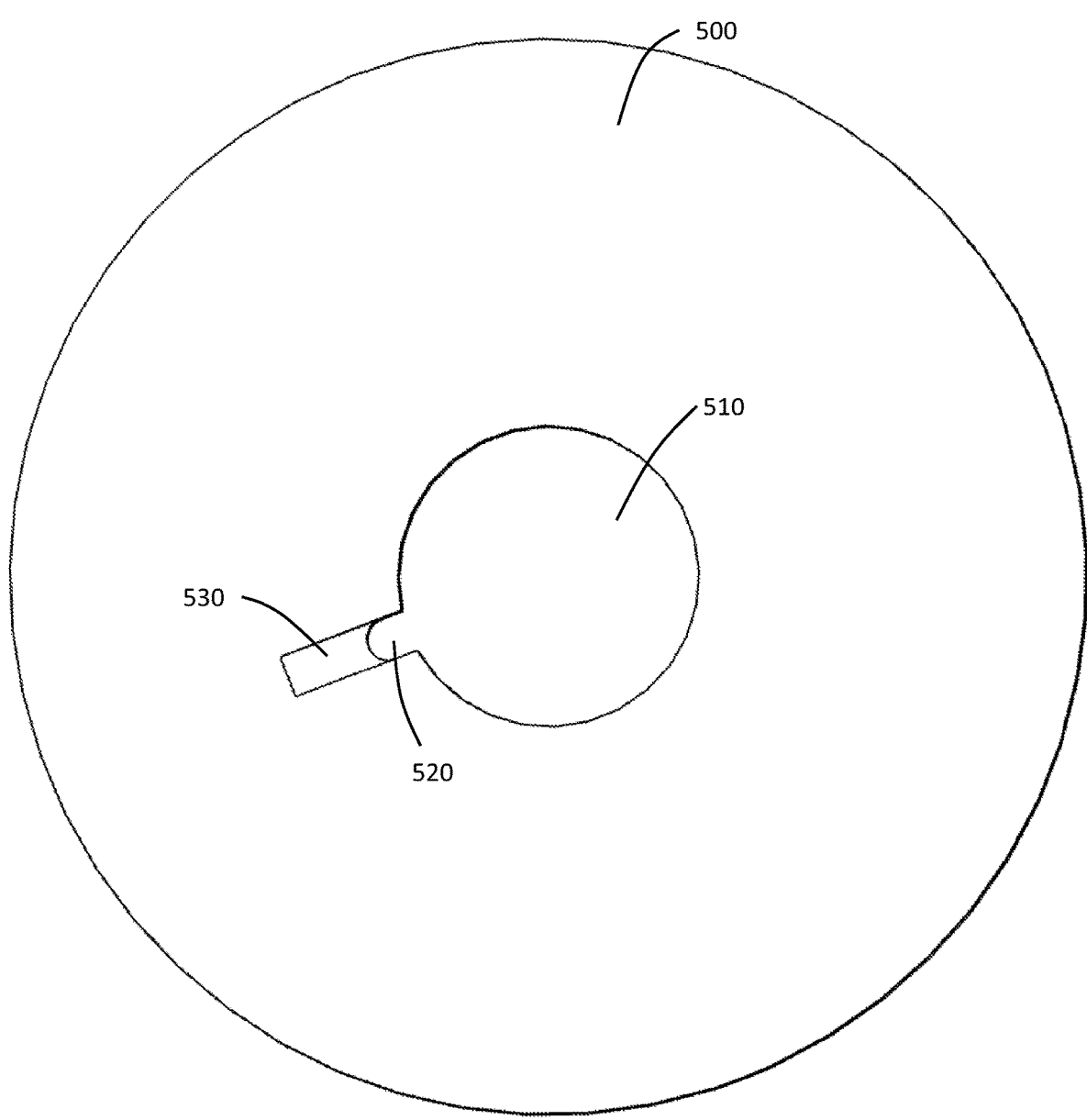
Figure 31:
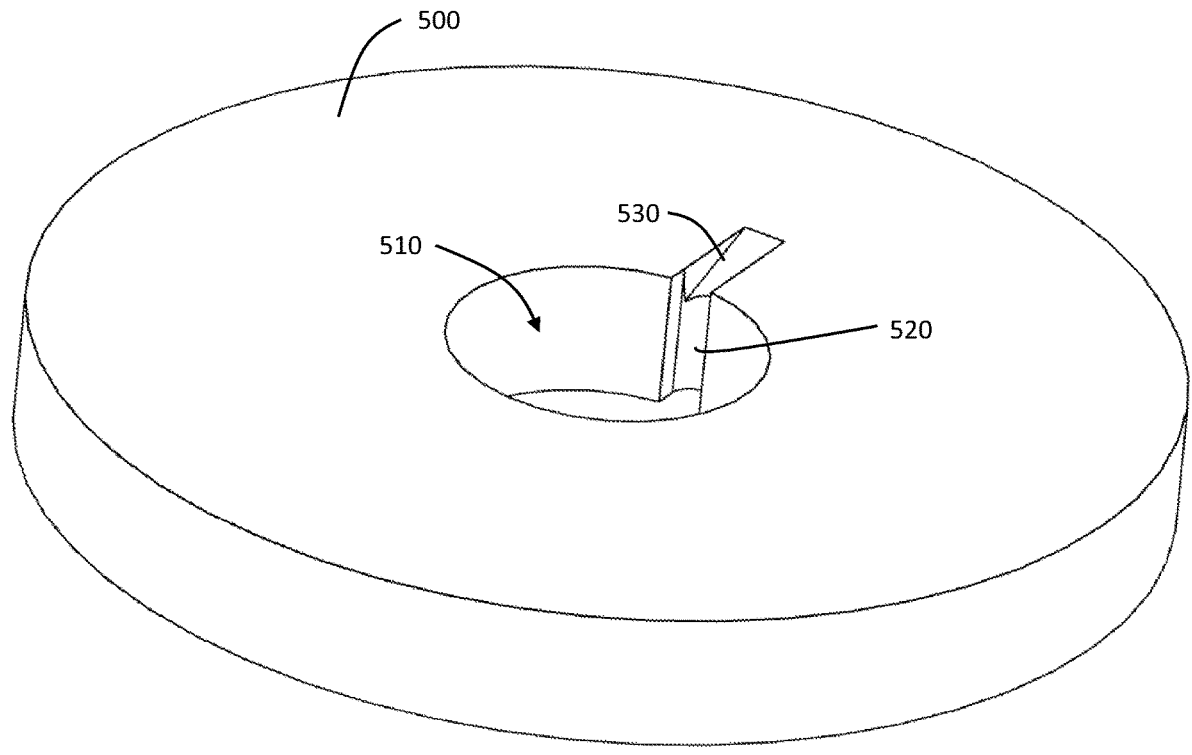
FIG. 31 is a schematic perspective view of a portion of the skull shown in FIG. 30.

Referring now to FIGS. 29-31 burr holes 510, 520 in a portion of a skull 500 are shown to illustrate a method that may be employed to implant the burr hole device, catheter and sheath, cranial access port, and assemblies described herein.

A first burr hole 510 is created in the skull 500. The edge of the skull 500 defines the first burr hole 510. The first burr hole 510 has a diameter sufficiently large to accommodate the device to be implanted in the burr hole 510. For example, the diameter of the burr hole 510 may be suitable for accommodating passage of a catheter and sheath body, accommodating a lower portion of a burr hole device or a lower portion of a cranial port device, or the like. In embodiments, the first burr hole 510 has a diameter in a range from about 4 millimeters to about 20 millimeters, such as from about 5 millimeters to about 15 millimeters. In embodiments, the first burr hole 510 has a diameter of about 5 millimeters. In embodiments, the first burr hole 510 has a diameter of about 15 millimeters.

A second burr hole 520 is created through the skull 500. The second burr hole 520 has a smaller diameter than the first burr hole 510. The second burr hole 520 is configured to receive a cable, such as a cable of a sheath as described herein. By feeding the cable through the second burr hole 520 the cable may avoid being pinched by any device, such as a cranial port device or a burr hole device, inserted into the first burr hole 510. In embodiments, the diameter of the second burr hole is in a range from 1 millimeter to 10 millimeters.

The first 510 and second 520 burr holes partially overlap. The second burr hole 520 forms a groove along the edge of the first burr hole 520 along the thickness of the skull 500. Such a configuration provides access to the second burr hole 520 through the first burr hole 510.

In embodiments, the first burr hole 510 is formed through the skull 500 prior to the second burr hole 520 being formed. In embodiments, the first burr hole 510 is formed through the skull 500 after to the second burr hole 520 being formed.

A trench 530 may be created in the top surface of the skull 500. The trench 530 has a first end and a second end. The first end of the trench 530 intersects the second burr 520, and the trench 530 extends away from the second burr hole 520 towards the second end. The trench 530 has a first depth at the first end and has a second depth at the second end. The first depth is greater than the second depth.

The trench 530 provides a ramp to allow the cable to exit the second burr hole 520 at an angle less than 90 degrees, which may prevent damage to conductors running through the cable.

The figures and description above describe burr hole devices, catheter access ports, catheters, sheaths, signal apparatus, and assemblies and systems comprising one or more of the burr hole devices, catheter access ports, catheters, sheaths, and signal apparatus, as well as methods of use and methods of implantation of such devices, assemblies, and systems. The devices, assemblies, systems, and methods described herein, among other things, allow or facilitate implanting a catheter into a brain of a subject and implanting a recording electrode into the brain of the subject. The catheter may be used to provide treatment to the subject, through delivery of therapeutic fluids to the brain, through removal of fluid from the brain, or through delivery of fluid to the brain and removal of fluid from the brain. The recording electrode may be used to monitor brain activity signals, which may or may not be related to the disease being treated. When related to the disease being treated, the monitored brain activity data may be used to adjust treatment (e.g., delivery of therapeutic fluid or removal of cerebral spinal fluid) based on the data.

The electrodes of the sheath, assembly, or systems described herein may be configured to detect electroencephalogram (EEG) signals. The sheath, assembly, or systems may comprise one or more electrodes. One or more electrodes may be a recording electrode. One or more electrodes may be a ground or reference electrode.

The sheath, assembly, or systems may comprise any suitable number of electrodes, such from 1 electrode to about 64 electrodes. For example, 2 to 32 electrodes, such 2 to 16 electrodes, or 2 to 10 electrodes.

In embodiments, most or all the electrodes are positioned such that they will be placed in white or grey matter of the brain when implanted. However, it is not necessary that all the electrodes be placed in the white or grey matter. If an electrode is not placed in white or grey matter, the recording from that electrode may continue to be captured and ultimately ignored or captured and considered. Alternatively, recording from that electrode may be inactivated. In embodiments, one or more electrodes are placed on a surface of the brain or above the brain as a ground or reference electrode.

Preferably, at least two electrodes are configured to be placed in white or grey matter. When multiple electrodes record signals from white or grey matter, coherent changes in activity between electrodes may be a powerful way to track more global changes. In some embodiments, the excitable state of a neural network is determined by monitoring a small neuronal population. The more excitable the small neuronal population, the higher the probability for activity to propagate throughout the network causing an 'avalanche' of activity. Such monitoring may be valuable for general brain state monitoring and may be particularly valuable for monitoring a brain state to predict a seizure.

In embodiments, the excitable state of a neural network is determined by monitoring brain activity at multiple brain locations (termed nodes). Interaction in the local field activity between the nodes can be used to determine the brain excitability. Such monitoring may be valuable for general brain state monitoring and may be particularly valuable for monitoring a change in brain state to predict a seizure The electrodes and associated signal processing apparatus may be configured in any suitable manner. For example, the electrodes and associated signal apparatus may be configured in differential mode or referential mode.

In differential mode, the system comprises an active electrode, a reference electrode, and a ground. The signal difference between an active electrode and a reference electrode may be amplified. The reference electrode may be a common reference for more than one active electrode. The reference electrode is preferably positioned a substantial distance from an active electrode and from the ground. In differential mode, the system may be configured to detect small differences between electrode pairs and may be less likely to be affected by large artifacts originating near the ground electrode. However, the system may not be particularly effective at detecting larger common signals.

Preferably, the system is configured to detect larger common signals. Larger common signals may be associated with an overall brain state or with a seizure.

To detect larger common signals, the system may be configured in referential mode, which may also be referred to as single-ended mode. Referential mode may use a single active electrode per amplifier. There may be more than one active electrode. In referential mode, the output of the active electrode is amplified relative to the ground electrode, as opposed to the reference electrode in differential mode. The ground is preferably placed a substantial distance from the active electrode, which may result in amplification of signals that affect larger parts of the brain. While being effective at detecting larger common signals, referential mode may be sensitive to artifacts. Proper placement of the ground electrode may mitigate some issues associated with artifacts.

The signal apparatus may comprise a power source, such as a battery, which may be rechargeable, or may be wirelessly powered. If the signal apparatus is wirelessly powered, the signal apparatus preferably includes an inductive coil, solenoid, or other suitable components to be wirelessly powered by an external apparatus and to transmit data regarding the signals recorded by the electrodes to the external apparatus.

In embodiments, the signal apparatus is implanted at a location where it may inductively couple with a device external to the subject. For example, the signal apparatus may be positioned under the scalp of the subject near an ear of the subject. Such positioning may allow the external device to be comfortably worn on or around the ear of the subject to provide suitable inductive coupling to power the signal apparatus and to wirelessly transmit data regarding the signals recorded by the electrodes from the signal apparatus to the external device. The external device may then transfer the data directly to the cloud or via another device, such as a smart phone, a personal computer, or the like, which may then transfer the data to a server in the cloud, or the like.

The signal apparatus may be configured to continuously transmit EEG data derived from an intracranial electrode. The signal apparatus may be configured to continuously transmit the EEG data for a long duration of time. The signal apparatus may be configured to transmit relatively unfiltered data containing a broad amount of relevant brain signal. That is, the signal apparatus may transmit data regarding a majority of the captured EEG data. For example, the EEG data corresponding to the transmitted data may not have been bandpass filtered. As another example, the subsets of the EEG data are not extracted for transmission. Rather, the majority of the EEG data is transmitted by the signal apparatus. The signal apparatus may be configured to continuously transmit data for 1 day or more, 1 week or more, 1 month or more, or 1 year or more.

The external device may be configured to continuously receive EEG data derived from an intracranial electrode. The external device may be configured to continuously receive the EEG data for a long duration of time. The external device may be configured to continuously receive data for 1 day or more, 1 week or more, 1 month or more, or 1 year or more.

The EEG data may be used for any suitable purpose. The EEG data may be used to treat, monitor, or treat and monitor a disease for which the catheter may be employed. The EEG data may be used to identify, classify, or predict a brain state associated with the disease being treated or that has been treated. The EEG data may be used to identify, classify, or predict a brain state that is not associated with the disease being treated or that has been treated. The EEG data may be used to identify, classify, or predict a brain state associated with the disease being treated or that has been treated and a brain state that is not associated with the disease being treated or that has been treated. The EEG data may be used to identify, classify, or predict a psychological brain state associated with the disease being treated or that has been treated and a brain state that is not associated with the disease being treated or that has been treated.

The EEG data may be used to develop or train an AI model that may identify, classify, or predict a brain state. The EEG data may be input into an AI model that may identify, classify, or predict a brain state. The brain state may or may not be associated with the disease being treated or that has been treated. The brain state may be a psychological brain state.

Development, training, refining, and utilizing AI models based on EEG data to identify, classify, or predict a brain state, such as a psychological brain state are discussed in U.S. patent application Ser. No. 17/380,694, entitled MONITORING BASED ON CONTINUOUS INTRACRANIAL EEG ACTIVITY, filed on Jul. 20, 2021, and naming Cerebral Therapeutics, Inc. as an Applicant, and U.S. Provisional Patent Application No. 63/280,367, entitled DEVELOPMENT AND IMPLEMENTATION OF PSYCHOLOGICAL STATE MODEL, filed on Nov. 17, 2021, and naming Cerebral Therapeutics, Inc. as an Applicant, which provisional applications are hereby incorporated herein by reference in their entireties to the extent that they do not conflict with the disclosure presented herein.

While the present disclosure is not so limited, an appreciation of various aspects of the disclosure will be gained through a discussion of the specific examples and illustrative embodiments provided below. Various modifications of the examples and illustrative embodiments, as well as additional embodiments of the disclosure, will become apparent herein.

Example 1: A burr hole device comprising a body having a top surface and a bottom surface and defining a lumen extending from the top surface to the bottom surface, wherein the lumen is configured to receive a catheter configured to allow fluid to flow to or from a brain of a subject, wherein at least a portion of the bottom surface is configured to be disposed on a surface of a skull adjacent to a burr hole in the skull of the subject, wherein the body further defines a top groove along the top surface, wherein the top groove extends from the lumen towards a lateral edge of the top surface of the body, wherein the top groove is configured to receive the catheter, wherein the body further defines a bottom groove along the bottom surface, wherein the bottom groove extends from a lateral edge of the bottom surface towards the lumen, wherein the bottom groove is configured to receive a cable.

Example 2: The burr hole device of Example 1, wherein the body defines an upper flange portion and a lower portion, wherein the lower portion is configured to be placed within the burr hole and the upper flange portion is configured to be disposed on the surface of the skull.

Example 3: The burr hole device of Example 2, wherein the bottom groove is disposed on a bottom surface of the upper flange portion.

Example 4: The burr hole device of Example 3, wherein the lower portion of the body defines a side groove along a side of the lower portion, wherein the side groove meets with the bottom groove.

Example 5: The burr hole device of any one of Examples 2 to 5, wherein the lower portion of the body is configured to have a clearance of 1 millimeter or less when disposed in the burr hole.

Example 6: The burr hole device of any one of Examples 2 to 5, wherein the lower portion of the body has an outer diametric dimension from 10 millimeters to 20 millimeters.

Example 7: The burr hole device of any one of Examples 2 to 6, wherein the upper flange portion of the body has an outer diametric dimension from 15 millimeters to 30 millimeters.

Example 8: A burr hole device comprising a body having a top surface and a bottom surface and defining a lumen extending from the top surface to the bottom surface, wherein the lumen is configured to receive a catheter configured to infuse fluid to, or withdraw fluid from, a brain of a subject, wherein at least a portion of the bottom surface is configured to be disposed on a surface of a skull adjacent to a burr hole in the skull of the subject, wherein the body further defines a first top groove along the top surface, wherein the first top groove extends from the lumen towards a lateral edge of the top surface of the body, wherein the first top groove is configured to receive the catheter, wherein the body further defines a second top groove along the top surface, wherein the second top groove extends from the lumen towards a lateral edge of the top surface of the body, wherein the second top groove is configured to receive a cable Example 9: The burr hole device of Example 8, wherein the body defines an upper flange portion and a lower portion, wherein the lower portion is configured to be placed within the burr hole and the upper flange portion is configured to be disposed on the surface of the skull.

Example 10. The burr hole device of Example 9, wherein the lower portion of the body is configured to have a clearance of 1 millimeter or less when disposed in the burr hole.

Example 11: The burr hole device of Example 9, wherein the lower portion of the body has an outer diametric dimension from 10 millimeters to 20 millimeters.

Example 12: The burr hole device of any one of Examples 9 to 11, wherein the upper flange portion of the body has an outer diametric dimension from 15 millimeters to 30 millimeters.

Example 13: A burr hole device comprising a body having a top surface and a bottom surface and defining a lumen extending from the top surface to the bottom surface, wherein the lumen is configured to receive a catheter configured to infuse fluid to, or withdraw fluid from, a brain of a subject, wherein at least a portion of the bottom surface is configured to be disposed on a surface of a skull adjacent to a burr hole in the skull of the subject, wherein the body further defines a top groove along the top surface, wherein the top groove extends from the lumen towards a lateral edge of the top surface of the body, wherein the top groove comprises a lower groove portion and an upper groove portion, the lower groove portion having a smaller diametric dimension than the upper groove portion, wherein the lower groove portion is configured to receive a cable, and wherein the upper groove portion is configured to receive the catheter such that the catheter is positioned over the cable when the both the cable and the catheter are received in the top groove Example 14: The burr hole device of Example 13, wherein the body defines an upper flange portion and a lower portion, wherein the lower portion is configured to be placed within the burr hole and the upper flange portion is configured to be disposed on the surface of the skull.

Example 15: The burr hole device of Example 14, wherein the lower portion of the body is configured to have a clearance of 1 millimeter or less when disposed in the burr hole.

Example 16: The burr hole device of Example 14, wherein the lower portion of the body has an outer diametric dimension from 10 millimeters to 20 millimeters.

Example 17: The burr hole device of any one of Examples 13 to 16, wherein the upper flange portion of the body has an outer diametric dimension from 15 millimeters to 30 millimeters.

Example 18: An assembly comprising: (i) the burr hole device of any one of Examples 1 to 17; the catheter; and a sheath comprising (i) a sheath body defining a sleeve lumen configured to receive the catheter, (ii) a recording electrode disposed on the sheath body, (iii) the cable, and (iv) a conductor electrically coupled to the recording electrode and extending in the cable.

Example 19: A method comprising: providing the assembly of Example 18; disposing the burr hole device in or about a burr hole of a subject; inserting the catheter through the lumen of the burr hole device; inserting the catheter through the sheath lumen; implanting a distal end of the catheter in a brain of the subject; implanting the recording electrode of the sheath beneath the skull of the subject; inserting the cable of the sheath in the bottom groove, the second top groove, or the bottom portion of the top groove; and inserting the catheter in the top groove, the first top groove, or the top portion of the top groove.

Example 20: The method of Example 19, wherein implanting the recording electrode of the sheath beneath the skull of the subject comprises implanting the electrode in the brain of the subject.

Example 21: The method of Example 19 or 20, wherein implanting a distal end of the catheter in the brain of the subject comprises implanting the distal end of the catheter in a cerebral ventricle.

Example 22: A burr hole device comprising (i) a body having a top surface and a bottom surface and defining a lumen extending from the top surface to the bottom surface, wherein the body defines an upper flange portion and a lower portion, wherein the lower portion is configured to be placed within the burr hole and the upper flange portion is configured to be disposed on the surface of the skull, wherein the lumen is configured to receive a catheter configured to infuse fluid to, or withdraw fluid from, a brain of a subject; and (ii) an electrode disposed on the bottom surface of the lower portion Example 23: The burr hole device of Example 22, wherein the bottom surface of the lower portion is configured to be placed on a surface of a brain or above the surface of the brain when the burr hole device is implanted.

Example 24: The burr hole device of Example 22, wherein the bottom surface of the lower portion extends from 3 millimeters to 7 millimeters from the bottom surface of the upper flange portion Example 25: The burr hole device of any one of Examples 22 to 24, wherein the lower portion of the body is configured to have a clearance of 1 millimeter or less when disposed in the burr hole.

Example 26: The burr hole device of Example 25, wherein the lower portion of the body has an outer diametric dimension from 10 millimeters to 20 millimeters.

Example 27: The burr hole device of any one of Examples 22 to 26, wherein the upper flange portion of the body has an outer diametric dimension from 15 millimeters to 30 millimeters.

Example 28: The burr hole device of any one of Examples 22 to 27, further comprising an electrical interconnect electrically coupled to the electrode.

Example 29: The burr hole device of Example 28, wherein the electrical interconnect is configured to electrically couple an implantable medical lead.

Example 30: The burr hole device of any one of Examples 22 to 29, wherein the body further defines a top groove along the top surface, wherein the top groove extends from the lumen towards a lateral edge of the top surface of the body, wherein the top groove is configured to receive the catheter.

Example 31: The burr hole device of any one of Examples 22 to 30, wherein the top grove is configured to grippingly engage the catheter.

Example 32: The burr hole device of Example 31, wherein the top groove comprises a lower groove portion and an upper groove portion, the lower groove portion having a smaller diametric dimension than the upper groove portion, wherein the lower groove portion is configured to receive a cable, and wherein the upper groove portion is configured to receive the catheter such that the catheter is positioned over the cable when the both the cable and the catheter are received in the top groove.

Example 33: The burr hole device of Example 31 or 32, wherein the body further defines a second top groove along the top surface, wherein the second top groove extends from the lumen towards a lateral edge of the top surface of the body, wherein the second top groove is configured to receive a cable.

Example 34: The burr hole device of any one of Examples 22 to 33, wherein the body further defines a bottom groove along the bottom surface, wherein the bottom groove extends from a lateral edge of the bottom surface towards the lumen, wherein the bottom groove is configured to receive a cable.

Example 35: An assembly comprising: the burr hole device of any one of Examples 22 to 34; and the catheter.

Example 36: The assembly of Example 35, further comprising a sheath comprising (i) a sheath body defining a sleeve lumen configured to receive the catheter, (ii) a recording electrode disposed on the sheath body, (iii) the cable, and (iv) a conductor electrically coupled to the recording electrode and extending in the cable.

Example 37: A method comprising operatively coupling to signal apparatus the electrode disposed on the bottom surface of the lower portion of the body of the burr hole device according to any one of Examples 22 to 34.

Example 38: The method of Example 37, wherein the signal apparatus is implantable signal apparatus.

Example 39: A method of Example 37 or 38, further comprising: providing the assembly of Examples 35 or 36; disposing the burr hole device in or about a burr hole of a subject; inserting the catheter through the lumen of the burr hole device; and implanting a distal end of the catheter in a brain of the subject.

Example 40: The method of Example 39, further comprising inserting the catheter in the top groove, the first top groove, or the top portion of the top groove.

Example 41: The method of Example 39 or 40 comprising: providing the assembly of Example 36; inserting the catheter through the sheath lumen; implanting the recording electrode of the sheath beneath the skull of the subject; and inserting the cable of the sheath in the bottom groove, the second top groove, or the bottom portion of the top groove.

Example 42: The method of Example 41, wherein implanting the recording electrode of the sheath beneath the skull of the subject comprises implanting the electrode in the brain of the subject.

Example 43: The method of any one of Examples 39 to 42, wherein implanting a distal end of the catheter in the brain of the subject comprises implanting the distal end of the catheter in a cerebral ventricle.

Example 44: A method comprising: providing the assembly of Example 35 or 36; disposing the burr hole device in or about a burr hole of a subject; inserting the catheter through the lumen of the burr hole device; and implanting a distal end of the catheter in a brain of the subject.

Example 45: The method of Example 44, further comprising inserting the catheter in the top groove, the first top groove, or the top portion of the top groove.

Example 46: The method of Example 44 or 45 comprising: providing the assembly of Example 36; inserting the catheter through the sheath lumen; implanting the recording electrode of the sheath beneath the skull of the subject; and inserting the cable of the sheath in the bottom groove, the second top groove, or the bottom portion of the top groove.

Example 47: The method of Example 46, wherein implanting the recording electrode of the sheath beneath the skull of the subject comprises implanting the electrode in the brain of the subject.

Example 48: The method of any one of Examples 44 to 47, wherein implanting a distal end of the catheter in the brain of the subject comprises implanting the distal end of the catheter in a cerebral ventricle.

Example 49: A burr hole device comprising: (i) a body defining an upper flange portion and a lower portion, wherein the lower portion is configured to be placed within the burr hole and the upper flange portion is configured to be disposed on the surface of the skull, wherein the body defines a cavity for receiving a cranial port device, wherein the lower portion defines an opening in communication with the cavity, wherein the opening is configured such that a catheter or a catheter connector of the port may be inserted therethrough; and an electrode disposed on the bottom surface of the lower portion.

Example 50: The burr hole device of Example 49, wherein a bottom surface of the lower portion is configured to be placed on a surface of a brain or above the surface of the brain when the burr hole device is implanted.

Example 51: The burr hole device of Example 49, wherein a bottom surface of the lower portion extends from 3 millimeters to 7 millimeters from a bottom surface of the upper flange portion.

Example 52: The burr hole device of any one of Examples 49 to 51, wherein the lower portion of the body is configured to have a clearance of 1 millimeter or less when disposed in the burr hole.

Example 53: The burr hole device of Example 52, wherein the lower portion of the body has an outer diametric dimension from 10 millimeters to 20 millimeters.

Example 54: The burr hole device of any one of Examples 49 to 53, wherein the upper flange portion of the body has an outer diametric dimension from 15 millimeters to 30 millimeters.

Example 55: The burr hole device of any one of Examples 49 to 54, further comprising an electrical interconnect electrically coupled to the electrode.

Example 56: The burr hole device of Example 55, wherein the electrical interconnect is configured to electrically couple an implantable medical lead.

Example 57: The burr hole device of any one of Examples 49 to 56, wherein the upper flange portion further defines a top groove, wherein the top groove extends from the cavity towards a lateral edge of the top surface, wherein the top groove is configured to receive the catheter.

Example 58. The burr hole device of Example 57, wherein the top groove comprises a lower groove portion and an upper groove portion, the lower groove portion having a smaller diametric dimension than the upper groove portion, wherein the lower groove portion is configured to receive a cable, and wherein the upper groove portion is configured to receive the catheter such that the catheter is positioned over the cable when the both the cable and the catheter are received in the top groove.

Example 60: The burr hole device of Example 58 or 59, wherein the upper flange portion further defines a second top groove along the top surface, wherein the second top groove extends from the cavity towards a lateral edge of the top surface of the body, wherein the second top groove is configured to receive a cable.

Example 61: The burr hole device of any one of Examples 49 to 60 and Examples 99 to 100, wherein the upper flange portion further defines a bottom groove along a bottom surface of the upper flange portion, wherein the bottom groove extends from a lateral edge of the bottom surface towards the cavity, wherein the bottom groove is configured to receive a cable.

Example 62: An assembly comprising: the burr hole device of any one of Examples 49 to 61 and Examples 99 to 100; and the cranial port device.

Example 63: The assembly of Example 62, wherein the cranial port device comprises an upper flange portion configured to rest on the upper flange portion of the burr hole device, and wherein the cranial port device comprises a lower portion configured to be received in the cavity of the burr hole device.

Example 64. The assembly of Example 63, wherein the cranial port device further comprises: a first fluid path; and a second fluid path, wherein the first fluid flow path extends from a first opening in the upper flange portion of the cranial port device to a first opening in the lower portion of the cranial port device, and wherein the second fluid flow path extends from a second opening in the upper flange portion of the cranial port device to a second opening in the lower portion of the cranial port device.

Example 65: The assembly of Example 62 to 64, further comprising a catheter operatively couplable or coupled to the cranial port device.

Example 66: The assembly of Example 65, wherein the catheter comprises a first lumen and a second lumen.

Example 67: The assembly of Example 66, wherein the first lumen of the catheter is in communication with the first fluid path of the cranial port device when the catheter is connected to the cranial port device, and wherein the second lumen of the catheter is in communication with the second fluid path of the cranial port device when the catheter is connected to the cranial port device.

Example 68: The assembly of any one of Examples 65 to 67, further comprising a sheath comprising (i) a sheath body defining a sleeve lumen configured to receive the catheter, (ii) a recording electrode disposed on the sheath body, (iii) the cable, and (iv) a conductor electrically coupled to the recording electrode and extending in the cable.

Example 69: A method comprising: providing the assembly of any one of Examples 62 to 68; disposing the lower portion of the body of the burr hole device in a burr hole of a subject such that the upper flange portion rests on a skull of the subject; inserting the cranial port device in the cavity of the burr hole device; and inserting the catheter or a catheter connector of the cranial port device through the opening of the lower portion of the body of the burr hole device.

Example 70: The method of Example 69, further comprising coupling the catheter to the catheter connector.

Example 71: The method of Example 69 or 70, further comprising: inserting the catheter through the sheath lumen; implanting a distal end of the catheter in a brain of the subject; and implanting the recording electrode of the sheath beneath the skull of the subject.

Example 72. The method of Example 71, further comprising: inserting the cable of the sheath in the bottom groove, the second top groove, or the bottom portion of the top groove; and inserting the catheter in the top groove, the first top groove, or the top portion of the top groove.

Example 73: A method comprising operatively coupling to signal apparatus the electrode disposed on the bottom surface of the lower portion of the body of the burr hole device according to any one of Examples 49 to 61 and Examples 99 to 100.

Example 74: The method of Example 69, wherein the signal apparatus is implantable signal apparatus.

Example 75: An implantable sheath comprising: a body having a proximal end and a distal end and defining a lumen from the proximal end to the distal end, wherein the lumen is configured to receive a catheter; an electrode disposed on the body; a cable extending from the body in proximity to the proximal end; and a conductor electrically coupled to the electrode and extending in the cable, wherein the cable comprises an electrical interconnect comprising a contact electrically coupled the conductor, wherein the sheath is configured to be completely implanted in a subject.

Example 76: An assembly comprising: the implantable sheath of Example 75; and the catheter, the catheter having a proximal end and a distal end, wherein the distal end of the catheter is configured to be implanted in a brain of a subject.

Example 77: An assembly comprising: a catheter configured to deliver fluid to or from a brain of a subject; a sheath comprising a lumen configured receive the catheter; and an electrode disposed on the sheath, wherein the catheter and sheath are configured such that when the catheter is received in the lumen of the sheath and a distal portion of the catheter is implanted in a brain of a subject, the electrode is positioned intracranially.

Example 78: The assembly of Example 77, wherein the sheath comprises a cable comprising a conductor electrically coupled to the electrode.

Example 79: The assembly of Example 78, further comprising a burr hole device, the burr hole device comprising: a body having a top surface and a bottom surface and defining a lumen extending from the top surface to the bottom surface, wherein the lumen is configured to receive the catheter, wherein at least a portion of the bottom surface is configured to be disposed on a surface of a skull adjacent to a burr hole in the skull of the subject, and wherein the body further defines a groove configured to receive the cable.

Example 80: A method comprising: creating a first burr hole having a first diameter in a skull of a subject wherein the skull defines an edge of the first burr hole; creating a second burr hole having a second diameter in the skull, wherein the second diameter is smaller than the first diameter, and wherein the first and second burr holes partially overlap.

Example 81: The method of Example 80, further creating a trench in the top surface of the skull, wherein the trench has a first end and a second end, wherein the first end of the trench intersects the second burr, and wherein the trench extends away from the second burr hole towards the second end.

Example 82: The method of Example 81, wherein the trench has a first depth at the first end and has a second depth at the second end, wherein the first depth is greater than the second depth.

Example 83: The method of any one of Examples 80 to 82, further comprising: inserting a catheter and sheath through the first burr hole, wherein the sheath is configured to receive the catheter and comprises an electrode and a cable comprising a conductor electrically coupled to the electrode; and inserting the cable through the second burr hole.

Example 84: The method of Example 83, as it depends from Example 81 or 82, further comprising inserting the cable in the trench.

Example 85: A burr hole device comprising a body having a top surface and a bottom surface and defining a lumen extending from the top surface to the bottom surface, wherein the lumen is configured to receive a catheter configured to allow fluid to flow to or from a brain of a subject. At least a portion of the body is configured to be inserted into a burr hole. The burr hole device further comprises an expansion member that may be deployed when the body is in the burr hole. The expansion member is configured to expand against a side of the burr hole to anchor the body within the burr hole.

Example 86: The burr hole device of Example 85, wherein the entire device is configured to be received in the burr hole.

Example 87: The burr hole device of Example 85 or 86, wherein the expansion member is deployable from a retracted state to an expanded state.

Example 88: The burr hole device of Example 87, further comprising a user actuatable member operatively couple to the expansion member, wherein actuation of the user actuatable member causes the expansion member to adapt the expanded state.

Example 89: The burr hole device of any one of Examples 85 to 88, wherein the body further defines a top groove along the top surface, wherein the top groove extends from the lumen towards a lateral edge of the top surface of the body, wherein the top groove is configured to receive the catheter, wherein the body further defines a bottom groove along the bottom surface, wherein the bottom groove extends from a lateral edge of the bottom surface towards the lumen, wherein the bottom groove is configured to receive a cable.

Example 90: The burr hole device of Example 89, wherein the body defines an upper flange portion and a lower portion, wherein the lower portion is configured to be placed within the burr hole and the upper flange portion is configured to be disposed on the surface of the skull.

Example 92: The burr hole device of Example 90, wherein the bottom groove is disposed on a bottom surface of the upper flange portion.

Example 93: The burr hole device of Example 91, wherein the lower portion of the body defines a side groove along a side of the lower portion, wherein the side groove meets with the bottom groove.

Example 94: The burr hole device of any one of Examples 90 to 93, wherein the lower portion of the body is configured to have a clearance of 1 millimeter or less when disposed in the burr hole.

Example 95: An assembly comprising: (i) the burr hole device of any one of Examples 85 to 94; the catheter; and a sheath comprising (i) a sheath body defining a sleeve lumen configured to receive the catheter, (ii) a recording electrode disposed on the sheath body, (iii) the cable, and (iv) a conductor electrically coupled to the recording electrode and extending in the cable.

Example 96: A method comprising: providing the assembly of Example 95; disposing the burr hole device in or about a burr hole of a subject; inserting the catheter through the lumen of the burr hole device; inserting the catheter through the sheath lumen; implanting a distal end of the catheter in a brain of the subject; implanting the recording electrode of the sheath beneath the skull of the subject; inserting the cable of the sheath in the bottom groove, the second top groove, or the bottom portion of the top groove; and inserting the catheter in the top groove, the first top groove, or the top portion of the top groove.

Example 97: The method of Example 96, wherein implanting the recording electrode of the sheath beneath the skull of the subject comprises implanting the electrode in the brain of the subject.

Example 98: The method of Example 96 or 97, wherein implanting a distal end of the catheter in the brain of the subject comprises implanting the distal end of the catheter in a cerebral ventricle.

Example 99: The burr hole device according to any one of Examples 49-61, further comprising one or more electrical component operatively coupled to the electrode.

Example 100: The burr hole device according to Example 99, wherein the one or more electrical component is configured to one or more of: store, transmit, and process data received from the electrode.

It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

What is claimed is:

1. A burr hole device comprising:

a body comprising a flange portion adapted to be disposed on a surface of a skull adjacent to a burr hole in the skull of a subject, the flange portion having a first surface and a second surface opposite the first surface;

a lower portion configured to be placed within the burr hole, the lower portion having a tubular portion and a third surface disposed along a bottom surface of the tubular portion, the lower portion configured to be placed within the burr hole; and a lumen extending from the first surface to the third surface, wherein the lumen is configured to receive a catheter configured to allow fluid to flow to or from a brain of the subject, wherein the flange portion defines a top groove along the first surface, the top groove extending from the lumen towards a lateral edge of the flange portion to receive the catheter, wherein the body further defines a cable groove comprising a first groove portion extending from a lateral edge of the second surface towards the lumen, a second groove portion along an outer surface of the tubular portion and a third groove portion extending from a lateral edge of the third surface towards the lumen, and wherein the cable groove is configured to receive a cable.

2. The burr hole device of claim 1, wherein the lower portion of the body is configured to have a clearance of 1 millimeter or less when adapted to be disposed in the burr hole.

3. The burr hole device of claim 1, wherein the lower portion of the body has an outer diametric dimension from 10 millimeters to 20 millimeters.

4. The burr hole device of claim 1, wherein the upper flange portion of the body has an outer diametric dimension from 15 millimeters to 30 millimeters.

5. An assembly comprising:

the burr hole device of claim 1; and a sheath disposed adjacent to the burr hole device comprising (i) a sheath body defining a sheath lumen configured to receive the catheter, (ii) a recording electrode disposed on the sheath body, (iii) the cable, and (iv) a conductor electrically coupled to the recording electrode and extending in the cable.

6. A method comprising:

providing the assembly of claim 5;

disposing the burr hole device in the burr hole of the subject;

inserting the catheter through the top groove of the flange portion;

inserting the catheter through the lumen of the burr hole device;

inserting the catheter through the sheath lumen;

implanting a distal end of the catheter in the brain of the subject;

implanting the recording electrode of the sheath beneath the skull of the subject;

inserting the cable of the sheath in the first, second and third groove portions of the cable groove.

7. The method of claim 6, wherein implanting the recording electrode of the sheath beneath the skull of the subject further comprises implanting the recording electrode in the brain of the subject.

8. The method of claim 6, wherein implanting a distal end of the catheter in the brain of the subject comprises implanting the distal end of the catheter in a cerebral ventricle.

* * * * *